(12) United States Patent
Garza et al.

(10) Patent No.: US 11,969,402 B2
(45) Date of Patent: Apr. 30, 2024

(54) COMPOSITIONS AND METHODS FOR SKIN REJUVENATION

(71) Applicant: THE JOHNS HOPKINS UNIVERSITY, Baltimore, MD (US)

(72) Inventors: Luis Garza, Baltimore, MD (US); Dongwon Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 176 days.

(21) Appl. No.: 17/611,752

(22) PCT Filed: May 14, 2020

(86) PCT No.: PCT/US2020/032841
§ 371 (c)(1),
(2) Date: Nov. 16, 2021

(87) PCT Pub. No.: WO2020/232226
PCT Pub. Date: Nov. 19, 2020

(65) Prior Publication Data
US 2022/0233490 A1 Jul. 28, 2022

Related U.S. Application Data

(60) Provisional application No. 62/848,645, filed on May 16, 2019.

(51) Int. Cl.
| | | |
|---|---|---|
| A61K 31/203 | (2006.01) | |
| A61K 8/36 | (2006.01) | |
| A61K 8/60 | (2006.01) | |
| A61K 31/5585 | (2006.01) | |
| A61K 31/713 | (2006.01) | |
| A61K 38/17 | (2006.01) | |
| A61P 17/02 | (2006.01) | |
| A61P 17/14 | (2006.01) | |
| A61Q 19/08 | (2006.01) | |

(52) U.S. Cl.
CPC ............ *A61K 31/203* (2013.01); *A61K 8/361* (2013.01); *A61K 8/606* (2013.01); *A61K 31/5585* (2013.01); *A61K 31/713* (2013.01); *A61K 38/1729* (2013.01); *A61P 17/02* (2018.01); *A61P 17/14* (2018.01); *A61Q 19/08* (2013.01); *A61K 2800/91* (2013.01)

(58) Field of Classification Search
CPC .......... A61P 35/00; A61P 37/04; A61P 43/00; A61P 37/02; A61P 17/00; A61P 17/12; A61P 29/00; A61P 31/04; A61P 31/12; A61P 3/10; A61P 31/10; A61P 33/02; A61P 35/02; A61P 37/06; A61P 1/02; A61P 17/02; A61P 19/02; A61P 25/00; A61P 33/10; A61P 35/04; A61P 37/08; A61P 1/04; A61P 17/14; A61P 19/00; A61P 25/28; A61P 33/00; A61P 41/00; A61P 5/48; A61P 9/00
See application file for complete search history.

(56) References Cited

U.S. PATENT DOCUMENTS

| | | | |
|---|---|---|---|
| 4,024,222 | A | 5/1977 | Ts'o |
| 4,130,641 | A | 12/1978 | Ts'o |
| 4,349,538 | A | 9/1982 | Levy |
| 5,258,369 | A | 11/1993 | Carter |
| 6,362,171 | B1 | 3/2002 | Suhadolnik |
| 10,105,305 | B2 | 10/2018 | Garza et al. |
| 2006/0211752 | A1 | 9/2006 | Kohn et al. |
| 2007/0031356 | A1 | 2/2007 | Buchwald Hunziker et al. |
| 2009/0253622 | A1 | 10/2009 | Van Noort et al. |
| 2009/0285779 | A1 | 11/2009 | Lebecque |
| 2010/0004304 | A1 | 1/2010 | Kohn et al. |
| 2010/0319074 | A1 | 12/2010 | Lu et al. |
| 2011/0082218 | A1 | 4/2011 | Wertz et al. |
| 2012/0009206 | A1 | 1/2012 | Carter |
| 2012/0115923 | A1 | 5/2012 | He et al. |
| 2012/0238610 | A1 | 9/2012 | Kohn et al. |
| 2012/0308581 | A1 | 12/2012 | Chemin et al. |
| 2013/0266588 | A1 | 10/2013 | Ji et al. |
| 2015/0202258 | A1 | 7/2015 | Berger |
| 2015/0274785 | A1 | 10/2015 | Li et al. |

(Continued)

FOREIGN PATENT DOCUMENTS

| | | |
|---|---|---|
| CN | 101780279 A | 7/2010 |
| WO | 2006054129 A1 | 5/2006 |

(Continued)

OTHER PUBLICATIONS

Chromek et al. The antimicrobial peptide cathelicidin protects the urinary tract against invasive bacterial infection. Nature Medicine., (2006), 12 (6), pp. 636-641.

(Continued)

*Primary Examiner* — Audrea B Coniglio
(74) *Attorney, Agent, or Firm* — Johns Hopkins Technology Ventures

(57) ABSTRACT

The present invention relates to the field of skin rejuvenation. Specifically, the present invention provides compositions and methods for promoting skin rejuvenation using a toll-like receptor 3 (TLR3) agonist and retinoic acid or derivatives thereof. In a specific embodiment, a method for treating wrinkles in a subject comprises the steps of (a) administering to the area of the subject comprising a wrinkle a composition comprising an effective amount of retinoic acid or a derivative thereof; and administering to the area of the subject comprising a wrinkle a composition comprising an effective amount of a TLR3 agonist.

18 Claims, 38 Drawing Sheets
Specification includes a Sequence Listing.

(56) References Cited

U.S. PATENT DOCUMENTS

| | | | |
|---|---|---|---|
| 2015/0297572 | A1 | 10/2015 | Niazi et al. |
| 2015/0374598 | A1 | 12/2015 | Wertz et al. |
| 2016/0220536 | A1 | 8/2016 | Kohn et al. |
| 2016/0256461 | A1 | 9/2016 | Christiano |

FOREIGN PATENT DOCUMENTS

| | | | |
|---|---|---|---|
| WO | 2006054177 | A1 | 5/2006 |
| WO | 2007079224 | A2 | 7/2007 |
| WO | 2007089151 | A1 | 8/2007 |
| WO | 2008-109083 | A2 | 9/2008 |
| WO | 2009130301 | A1 | 10/2009 |
| WO | 2009130616 | A2 | 10/2009 |
| WO | 2009136282 | A1 | 11/2009 |

OTHER PUBLICATIONS

Zanetti. Cathelicidins, multifunctional peptides of the innate immunity. J Leukoc. Biol., (2004), 75 (1), pp. 39-48.
Ganz. Defensins: antimicrobial peptides of innate immunity. Nat. Rev. Immunol., (2003), 3 (9), pp. 710-720.
Gudmundsson et al. The human gene FALL39 and processing of the cathelin precursor to the antibacterial peptide LL-37 in granulocytes. Eur J. Biochem., (1996), 38 (2), pp. 325-332.
Sorensen et al. Human cathelicidin, hCAP-18, is processed to the antimicrobial peptide LL-37 by extracellular cleavage with proteinase 3. Blood., (2001), 97 (12), pp. 3951-3959.
Zanetti et al. Cathelicidins: a novel protein family with a common proregion and a variable C-terminal antimicrobial domain. FEBS Lett., (1995), 374 (1), pp. 1-5.
Neville et al. Lipid headgroup discrimination by antimicrobial peptide LL-37: insight into mechanism of action. Biophys. J., (2006), 90 (4), pp. 1275-1287.
Oren et al. Structure and organization of the human antimicrobial peptide LL-37 in phospholipid membranes: relevance to the molecular basis for its non-cell-selective activity. Biochem. J., (1999), 341 (Pt 3), pp. 501-513.
Niyonsaba et al. Epithelial cell-derived antibacterial peptides human beta-defensins and cathelicidin: multifunctional activities on mast cells. Curr Drug Targets Inflamm Allergy., (2003), 2 (3), pp. 224-231.
Mukherjee et al. Retinoids in the treatment of skin aging: an overview of clinical efficacy and safety. Clin Interv Aging, 2006, 1(4), pp. 327-348.
Kwon et al. Promotive effect of minoxidil combined with all-trans retinoic acid (tretinoin) on human hair growth in vitro. J Korean Med Sci, 2007, 22(2), pp. 283-289.
Lin et al. Toll-Like Receptor 3 Ligand Polyinosinic: Polycytidylic Acid Promotes Wound Healing in Human and Murine Skin. J Invest Dermatol, 2012, 132(8), pp. 2085-2092.
Borkowski et al. Toll-like receptor 3 activation is required for normal skin barrier repair following UV damage. J Invest Dermatol, 2015, 135(2), pp. 569-578 (1-22).
Bazzano et al. Effect of Retinoids on Follicular Cells. J Invest Dermatol, 1993, 101(1 Suppl), pp. 138S-142S.
Kong et al. A comparative study of the effects of retinal and retinoic acid on histological, molecular, and clinical properties of human skin. J Cosmet Dermatol, 2016, 15(1), pp. 49-57.
Ito et al. Wnt-dependent de novo hair follicle regeneration in adult mouse skin after wounding. Nature., (2007), 447 (7142), pp. 316-320.
Breedis. Regeneration of hair follicles and sebaceous glands from the epithelium of scars in the rabbit. Cancer Res., (1954), 14 (8), pp. 575-579.
Wang et al. Principles and mechanisms of regeneration in the mouse model for wound-induced hair follicle neogenesis. Regeneration (Oxf)., (2015), 2 (4), pp. 169-181.
Takeo et al. Wound Healing and Skin Regeneration. Cold Spring Harb Perspect Med., (2015), 5 (1), pp. a023267.

Lim et al. Hedgehog stimulates hair follicle neogenesis by creating inductive dermis during murine skin wound healing. Nat Commun., (2018), 9 (1), p. 4903.
Gay et al. Fgf9 from dermal gammadelta T cells induces hair follicle neogenesis after wounding. Nat Med., (2013), 19 (7), pp. 916-923.
Plikus et al. Regeneration of fat cells from myofibroblasts during wound healing. Science., (2017), 355 (6326), pp. 748-752.
Wu et al. Intrinsic Immunity Shapes Viral Resistance of Stem Cells. Cell. (2018), 172 (3), pp. 423-438.e25.
Nelson et al. dsRNA Released by Tissue Damage Activates TLR3 to Drive Skin Regeneration. Cell Stem Cell., (2015), 17 (2), pp. 139-151.
Duester. Retinoic acid synthesis and signaling during early organogenesis. Cell., (2008), 134 (6), pp. 921-931.
Stocum. Mechanisms of urodele limb regeneration. Regeneration (Oxf)., (2017), 4 (4), pp. 159-200.
Li et al. RXR-alpha ablation in skin keratinocytes results in alopecia and epidermal alterations. Development., (2001), 128 (5), pp. 675-688.
Okano et al. Cutaneous retinoic acid levels determine hair follicle development and downgrowth. J Biol Chem., (2012), 287 (47), pp. 39304-39315.
Fisher et al. Molecular basis of sun-induced premature skin ageing and retinoid antagonism. Nature., (1996), 379 (6563), pp. 335-339.
Canino et al. A STAT3-NFkB/DDIT3/CEBPbeta axis modulates ALDH1A3 expression in chemoresistant cell subpopulations. Oncotarget., (2015), 6 (14), pp. 12637-12653.
Cabezas-Wallscheid et al. Vitamin A—Retinoic Acid Signaling Regulates Hematopoietic Stem Cell Dormancy. Cell., (2017), 169 (5), pp. 807-823.e19.
Lai et al. Commensal bacteria regulate Toll-like receptor 3-dependent inflammation after skin injury. Nat Med., (2009), 15 (12), pp. 1377-1382.
Bernard et al. Ultraviolet radiation damages self noncoding RNA and is detected by TLR3. Nat Med., (2012), 18 (8), pp. 1286-1290.
Ito et al. Stem cells in the hair follicle bulge contribute to wound repair but not to homeostasis of the epidermis. Nat Med., (2005), 11 (12), pp. 1351-1354.
Rhinn et al. Retinoic acid signalling during development. Development., (2012), 139 (5), pp. 843-858.
Cunningham et al. Mechanisms of retinoic acid signalling and its roles in organ and limb development. Nat Rev Mol Cell Biol., (2015), 16 (2), pp. 110-123.
Elder et al. Retinoic acid receptor gene expression in human skin. J Invest Dermatol., (1991), 96 (4), pp. 425-433.
Viallet et al. Retinoic acid and mouse skin morphogenesis. I. Expression pattern of retinoic acid receptor genes during hair vibrissa follicle, plantar, and nasal gland development. J Invest Dermatol., (1994), 103 (1), pp. 116-121.
Cabezas-Wallscheid, N. et al. Cabezas-Wallscheid, N. et al. Vitamin A-Retinoic Acid Signaling Regulates Hematopoietic Stem Cell Dormancy. Cell., (2017), 169 (5), pp. 807-823.e19.
Paulsen et al., Antimicrobial peptides are expressed and produced in healthy and inflamed human synovial membranes. J Pathol., (2002), 198 (3), pp. 369-377.
Zhang et al. Antimicrobial Peptide LL37 and MAVS Signaling Drive Interferon-beta Production by Epidermal Keratinocytes during Skin Injury. Immunity., (2016), 45 (1), pp. 119-130.
Mandy. Tretinoin in the preoperative and postoperative management of dermabrasion. J Am Acad Dermatol., (1986), 15 (4 Pt 2), pp. 878-879, 888-9.
Kato et al. Length-dependent recognition of double-stranded ribonucleic acids by retinoic acid-inducible gene-I and melanoma differentiation-associagene 5. J Exp Med., (2008), 205 (7), pp. 1601-1610.
Normand et al. A method for the isolation and serial propagation of keratinocytes, endothelial cells, and fibroblasts from a single punch biopsy of human skin. In Vitro Cell Dev Biol Anim. (1995), 31 (6), pp. 447-455.
Garza et al. Bald scalp in men with androgenetic alopecia retains hair follicle stem cells but lacks CD200-rich and CD34-positive hair follicle progenitor cells. J Clin Invest., (2011), 121 (2), pp. 613-622.

(56) References Cited

OTHER PUBLICATIONS

Aasen et al. Isolation and cultivation of human keratinocytes from skin or plucked hair for the generation of induced pluripotent stem cells. Nat Protoc., (2010), 5 (2), pp. 371-382.

Chapman et al. Human keratinocytes are efficiently immortalized by a Rho kinase inhibitor. J Clin Invest., (2010), 120 (7), pp. 2619-2626.

Myung et al. Epithelial Wnt ligand secretion is required for adult hair follicle growth and regeneration. J Invest Dermatol., (2013), 133 (1), pp. 31-41.

Zhu et al. After Skin Wounding, Noncoding dsRNA Coordinates Prostaglandins and Wnts to Promote Regeneration. J Invest Dermatol., (2017), 137 (7), pp. 1562-1568.

Wisniewski et al. Universal sample preparation method for proteome analysis. Nat Methods., (2009), 6 (5), pp. 359-362.

Erde et al. Enhanced FASP (eFASP) to Increase Proteome Coverage and Sample Recovery for Quantitative Proteomic Experiments. J Proteome Res., (2014), 13 (4), pp. 1885-1895.

Williamson et al. High-performance hybrid Orbitrap mass spectrometers for quantitative proteome analysis: Observations and implications. Proteomics., (2016), 16 (6), pp. 907-914.

Dorfer et al. MS Amanda, a universal identification algorithm optimized for high accuracy tandem mass spectra. J Proteome Res. (2014), 13 (1), pp. 3679-3684.

Kall et al. Semi-supervised learning for peptide identification from shotgun proteomics datasets. Nature Methods., (2007), 4 (11), pp. 923-925.

Kramer et al. Causal analysis approaches in Ingenuity Pathway Analysis. Bioinformatics (Oxford)., (2014), 30 (4), pp. 523-530.

Mi et al. PANTHER version 11: expanded annotation data from Gene Ontology and Reactome pathways, and data analysis tool enhancements. Nucleic acids research., (2017), 45 (D1), pp. D183-D189.

Huang et al. Systematic and integrative analysis of large gene lists using DAVID bioinformatics resources. Nature Protocols., (2009), 4 (1), pp. 44-57.

Jones et al. Use of fast HPLC multiple reaction monitoring cubed for endogenous retinoic acid quantification in complex matrices. Anal Chem., (2015), 87 (6), pp. 3222-3230.

Kane et al. Quantification of endogenous retinoic acid in limited biological samples by LC/MS/MS. Biochem J., (2005), 388 (Pt 1), pp. 363-369.

Kane et al. Quantitative profiling of endogenous retinoic acid in vivo and in vitro by tandem mass spectrometry. Anal Chem., (2008), 80 (5), pp. 1702-1708.

Kane et al. Quantification of endogenous retinoids. Methods Mol Biol., (2010), 652, pp. 1-54.

Kane et al. HPLC/UV quantitation of retinal, retinol, and retinyl esters in serum and tissues. Anal Biochem., (2008), 378 (1), pp. 71-79.

Livak et al. Analysis of relative gene expression data using real-time quantitative PCR and the 2(-Delta Delta C(T)) Method. Methods., (2001), 25 (4), pp. 402-408.

Zanetti et al. The cDNA of the neutrophil antibiotic Bac5 predicts a pro-sequence homologous to a cysteine proteinase inhibitor that is common to other neutrophil antibiotics. J. Biol. Chem., (1993), 268 (1), pp. 522-526.

Lehrer et al. Antimicrobial peptides in mammalian and insect host defence. Curr. Opin. Immunol., (1999), 11 (1), pp. 123-127.

Anderson K. V., et al. (1985). Establishment of dorsal-ventral polarity in the Drosophila embryo: the induction of polarity by the Toll gene product. Cell 42, 791-798.

Barker N. (2008). The canonical Wnt/betacatenin signalling pathway. Methods Mol Biol 468, 5-15.

Schmidt, K., et al., "APC-independent activation of NK cells by the toll-like receptor 3 agonist double-stranded RNA" The Journal of Immunology (2004) vol. 172, No. 1, pp. 138-143.

Zhang, J., et al., "Toll-like receptor 3 agonist induces impairment of uterine vascular remodeling and fetal losses in CBA x DBA/2 mice" Journal of Reproductive Immunology (2007) vol. 74, No. 1, pp. 61-67.

Brockes J. P., et al. (2001). Regeneration as an evolutionary variable. Journal of anatomy 199, 3-11.

Carpenter A. E., et al. (2006). CellProfiler: image analysis software for identifying and quantifying cell phenotypes. Genome biology 7, RIOO.

Fan C., et al. (2011). Characterization and quantification of wound-induced hair follicle neogenesis using in vivo confocal scanning laser microscopy. Skin Res Technol 17, 387-397.

Fuchs E., et al. (2002). Getting under the skin of epidermal morphogenesis. Nat Rev Genet 3, 199-209.

Galun E., et al. (2013). The regenerative activity of interleukin-6. Methods Mol Biol 982, 59-77.

Pan, L., et al., "Toll-like receptor 3 agonist poly I:C protects against simulated cerebral ischemia in vitro and in vivo" Acta Pharmacologica Sinica (2012) vol. 33, No. 10, pp. 1246-1253.

Heinrich, P. C., et al. (2003). Principles of interleukin (IL)-6-type cytokine signalling and its regulation. Biochem J 374, 1-20.

Imokawa Y., et al. (2003). Selective activation of thrombin is a critical determinant for vertebrate lens regeneration. Current biology: C B 13, 877-881.

Irizarry R. A., et al. (2003). Summaries of Affymetrix GeneChip probe level data. Nucleic Acids Res 31, e15.

Kumar, A., et al., "Toll-like receptor 3 agonist poly(I:C)-induced antiviral response in human corneal epithelial cells" Immunology (2006) vol. 117, No. 1, pp. 11-21.

Yamashita, M., et al. A TRIF-Independent Branch of TLR3 Signaling. Journal of Immunology, 188: 000-000(2012).

Kariko K., et al. (2004). mRNA is an endogenous ligand for Toll-like receptor 3. J Biol Chem 279, 12542-12550.

Karim, R., et al. (2011). Human papillomavirus deregulates the response of a cellular network comprising of chemotactic and proinflammatory genes. PLoS One 6, el 7848.

Kligman A. M., and Strauss J. S. (1956). The formation of vellus hair follicles from human adult epidermis. J Invest Dermatol 27, 19-23.

Koster, M. I., et al. (2004). p63 is the molecular switch for initiation of an epithelial stratification program. Genes Dev 18, 126-131.

Koster< M. I., and Roop, D.R. (2004). The role of p63 in development and differentiation of the epidermis. Journal of dermatological science 34, 3-9.

Dasu M. R., et al. Toll-Like Receptors in Wound Healing: Location, Accessibility, and Timing. Journal of Investigative Dermatology 132, 1955-1958 (2012).

Lamouille S., et al. (2014). Molecular mechanisms of epithelial-mesenchymal transition. Nature reviews Molecular cell biology 15, 178-196.

Lebre M. C., et al. (2007). Human keratinocytes express functional Toll-like receptor 3, 4, 5, and 9. J Invest Dermatol 127, 331-341.

Lee J., et al. (2012). Activation of innate immunity is required for efficient nuclear reprogramming. Cell 151, 547-558.

Occleston, N. L., et al. Prevention and reduction of scarring in the skin by Transforming Growth Factor beta 3 (TGFB3): from laboratory discovery to clinical pharmaceutical. J. Biomater. Sci. Polymer Edn, 19(8); 1047-1063 (2008).

Liu Y., et al. (2003). Keratin 15 Promoter Targets Putative Epithelial Stem Cells in the Hair Follicle Bulge. 121, 963-968.

Luis N.M.. et al. (2012a). Polycomb in Stem Cells:PRCI Branches Out. Cell Stem Cell 11, 16-21.

Luis N. M., et al. (2012b). Regulation of human epidermal stem cell proliferation and senescence requires polycomb-dependent and -independent functions of Cbx4. Cell Stem Cell 9, 233-246.

Lundberg A. M., et al. (2007). Key differences in TLR3/poly I:C signaling and cytokine induction by human primary cells: a phenomenon absent from murine cell systems. Blood 110, 3245-3252.

Melkamu T., et al. (2013). TLR3 activation evokes IL-6 secretion, autocrine regulation of Stat3 signaling and TLR2 expression in human bronchial epithelial cells. J Cell Commun Signal 7, 109-118.

(56) References Cited

OTHER PUBLICATIONS

Mescher A. L. (1996). The cellular basis of limb regeneration in urodeles. The International journal of developmental biology 40, 785-795.

Millar S. E. (2002). Molecular mechanisms regulating hair follicle development. J Invest Dermatol 118, 216-225.

Rhett J. M., et al. Novel therapies for scar reduction and regenerative healing of skin wounds. Trends in Biotechnology, 26(4); 173-180 (2008).

Nelson A. M., et al. (2013). Prostaglandin D(2) Inhibits Wound-Induced Hair Follicle Neogenesis through the Receptor, Gpr44. The Journal of investigative dermatology 133, 881-889.

Sanchez Alvarado A. (2006). Planarian regeneration: its end is its beginning Cell 124, 241-245.

St-Jaques B., et al. (1998). Sonic hedgehog signaling is essential for hair development. Current biology: CB 8, 1058-1068.

Torok M. A., et al. (1999). Sonic hedgehog (shh) expression in developing and regenerating axolotl limbs. The Journal of experimental zoology 284, 197-206.

Uematsu S., and Akira S. (2007). Toll-like receptors and Type I interferons. J Biol Chem 282, 15319-15323.

Yan C., Grimm et al. (2010). Epithelial to mesenchymal transition in human skin wound healing is induced by tumor necrosis factor-alpha through bonemorphogenic protein-2. The American journal of pathology 176, 2247-2258.

Bhartiya et al., Enhanced Wound Helaing in Animal Models by Interferon and an Interferon Inducer. J Cell Physiol. 1992; 150 (2): 312-9.

Sato T., et al. Accelerated wound healing mediated by activation of Toll-like receptor 9. Wound Rep Reg 18; 586-593 (2010).

Lin, Q., et al. Impaired Wound Healing with Defective Expression of Chemokines and Recruitment of Myeloid Cells in TLR3-Deficient Mice. The Journal of Immunology, 186: 3710-3717 (2011).

U.S. Appl. No. 15/120,189 Office Action dated Aug. 23, 2017.

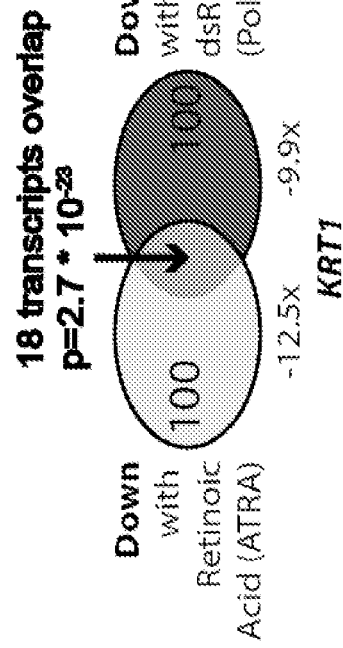
FIG. 1C
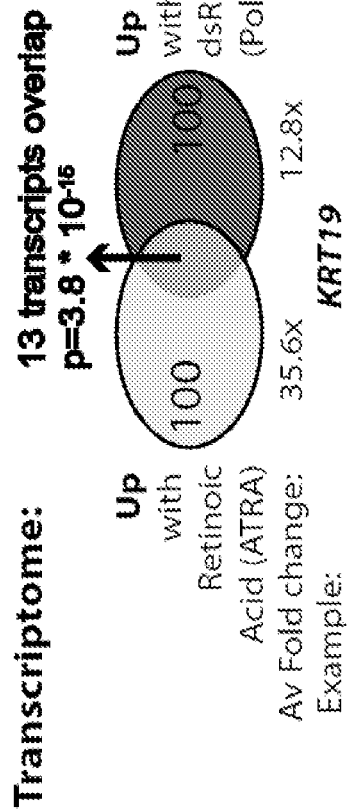
FIG. 1D
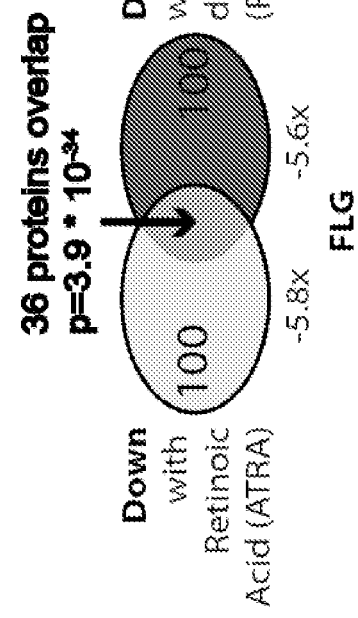
FIG. 1E
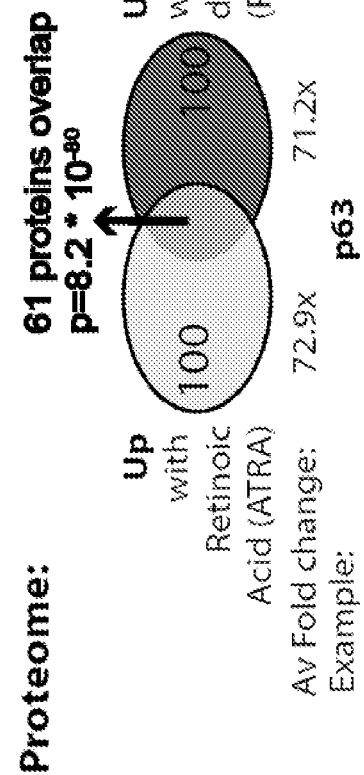

| Induced | |
|---|---|
| Gene Ontology Term | P-value |
| Cell development | 0.0025 |
| Cell division | 0.0044 |
| Positive regulation of cell proliferation | 0.0048 |
| Response to interferon-gamma | 0.0061 |
| Cell differentiation | 0.0083 |
| Cellular developmental process | 0.014 |
| Epithelial cell development | 0.015 |

| Inhibited | |
|---|---|
| Gene Ontology Term | P-value |
| Skin development | 1.4E-08 |
| Epidermis development | 0.000023 |
| Epidermal cell differentiation | 0.000039 |
| Establishment of skin barrier | 0.000056 |
| Regulation of water loss via skin | 0.0007 |
| Tissue development | 0.00015 |
| Keratinocytes differentiation | 0.0016 |

FIG. 1F

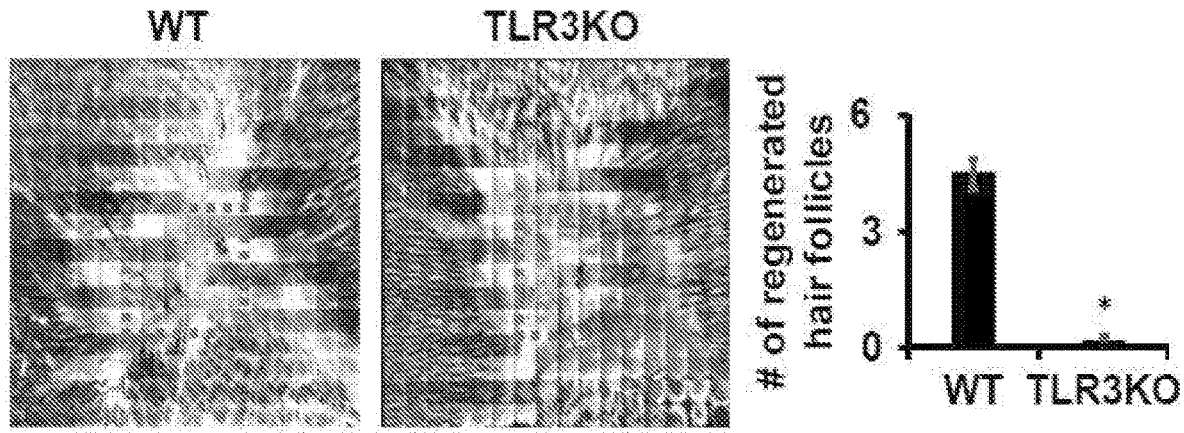
FIG. 2G
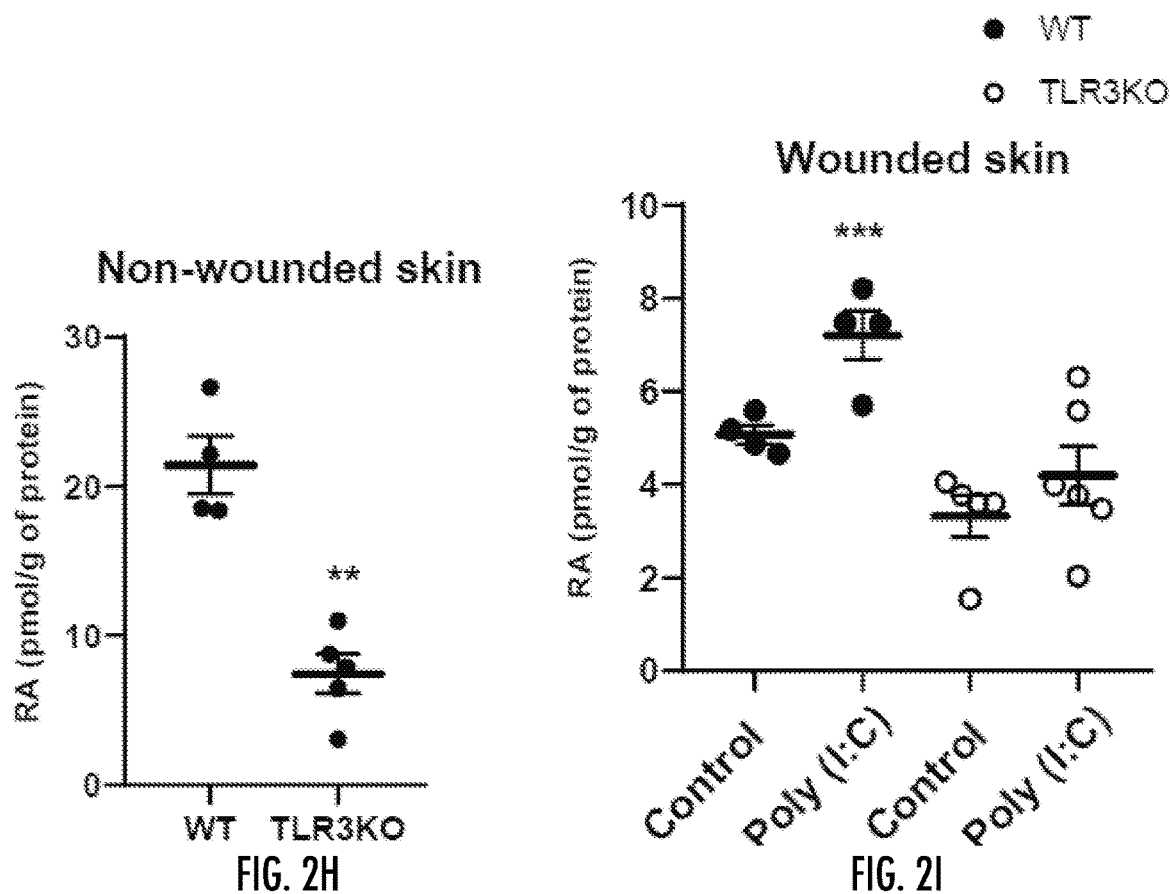
FIG. 2H
FIG. 2I

| Top 100 genes induced by RA | Gene Ontology Term | Count | P-value |
|---|---|---|---|
| | Epidermis development | 13 | 2.4E-8 |
| | Skin development | 12 | 6.4E-8 |
| | Detoxification | 5 | 9.6E-6 |
| | Proteolysis | 19 | 2.5E-4 |

| Bottom 100 genes induced by RA | Gene Ontology Term | Count | P-value |
|---|---|---|---|
| | Positive regulation on inflammatory response | 5 | 1.6E-4 |
| | Hair follicle morphogenesis | 4 | 4.6E-4 |
| | Collagen fibril organization | 4 | 6.3E-4 |
| | Intermediate filament organization | 3 | 3.7E-3 |

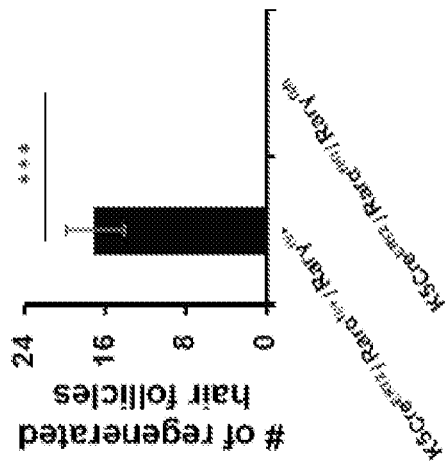
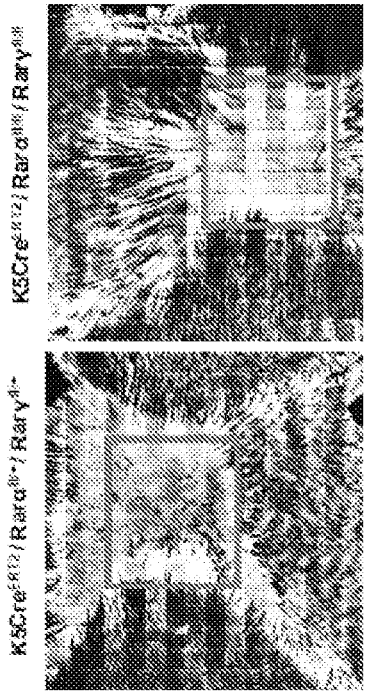
FIG. 9A
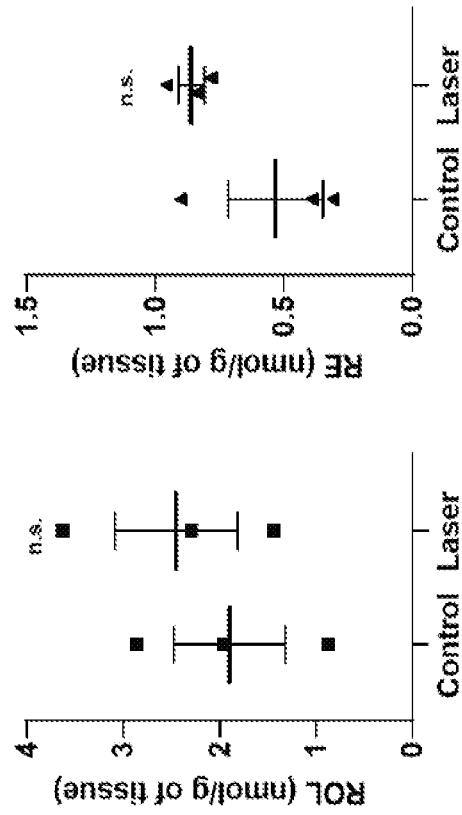
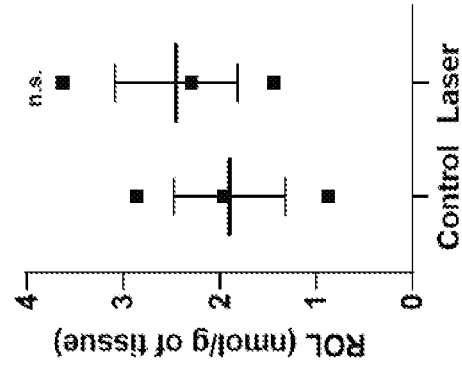
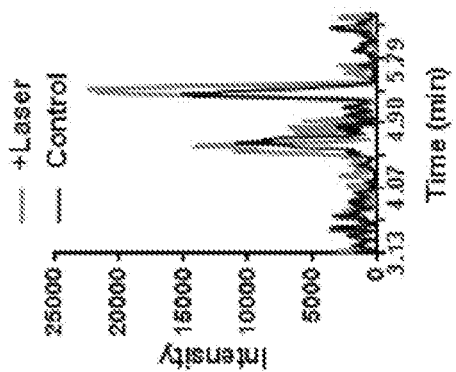
FIG. 9B
FIG. 9C
FIG. 9D

C57BL/6J

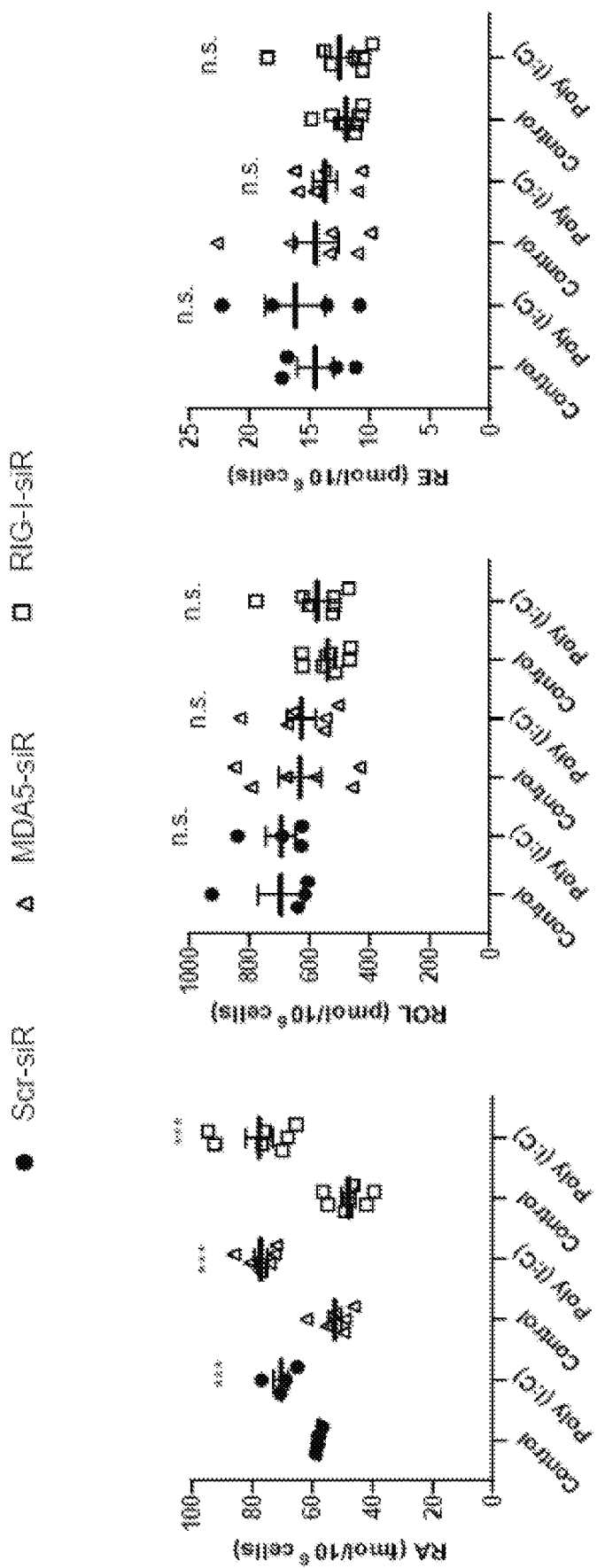

COMPOSITIONS AND METHODS FOR SKIN REJUVENATION

CROSS-REFERENCE TO RELATED APPLICATIONS

This application is a 35 U.S.C. § 371 U.S. national entry of International Application PCT/US2020/032481, having an international filing date of May 14, 2020, which claims the benefit of U.S. Provisional Application No. 62/848,645, filed May 16, 2019, which is incorporated herein by reference in its entirety.

STATEMENT OF GOVERNMENTAL INTEREST

This invention was made with government support under grant nos. AR064297 and AR068280, awarded by the National Institutes of Health. The government has certain rights in the invention.

FIELD OF THE INVENTION

The present invention relates to the field of skin rejuvenation. Specifically, the present invention provides compositions and methods for promoting skin rejuvenation using a TLR3 agonist and retinoic acid or derivatives thereof.

INCORPORATION-BY-REFERENCE OF MATERIAL SUBMITTED ELECTRONICALLY

This application contains a sequence listing. It has been submitted electronically via EFS-Web as an ASCII text file entitled "P15778-02_ST25.txt." The sequence listing is 3,019 bytes in size, and was created on May 12, 2020. It is hereby incorporated by reference in its entirety.

BACKGROUND OF THE INVENTION

Tissue morphogenesis occurs with high fidelity during development, but reactivation of morphogenesis to promote regeneration after injury in adults is rare but a major goal. Inducing regeneration in adults could counter post-injury fibrosis that contributes largely to human morbidity. Large wounds in mice and rabbits result in de novo hair follicle morphogenesis[1,2]. In regeneration, damaged tissues employ endogenous signaling to mobilize the proliferation and differentiation of resident stem cells for repair. Here, the present inventors use the model of Wound Induced Hair Neogenesis (WIHN) to identify mechanisms of reactivating developmental pathways in adult regeneration. In WIHN after full-thickness cutaneous wounds to the depth of skeletal muscle, epidermal stem cells drive not just re-epithelialization but also hair follicle morphogenesis as during embryogenesis[3,4]. While important advancements have been made on the role of Wnt[1]/Shh[5] signaling, γ-δ T cells[6], and myofibroblasts[7] the mechanisms by which epidermal stem cells induce skin regeneration are still unclear[3]. Recent evidence has shown that anti-viral pathways are hallmarks of diverse stem cells[8]. Additionally, the present inventors reported that damaged skin activates Toll Like Receptor 3 (TLR3) signaling to induce hair follicle regeneration[9]. Together, these findings suggest that in addition to other pathways, TLR3 signaling as a damage sensor might connect stem cell activity to regeneration.

In separate studies of developmental biology, Retinoic Acid (RA) is known to control appendage development and regeneration[10], for example in the patterning of the blastema that coordinates salamander limb regrowth after amputation[11]. Underscoring a similarity between limb appendage and hair follicle (termed a skin appendage) development, abnormal RA signaling and accumulation also cause progressive hair loss[12] and inappropriate hair follicle morphogenesis[13] Separately, among other uses, RA is commonly used clinically for facial aesthetic rejuvenation[14], as are also a variety of other skin damaging treatments such as dermabrasion or laser resurfacing. These data indicate that RA biologically acts as an essential morphogen in development and regeneration, but interestingly its clinical use overlaps that with damage inducing therapies. This suggest the hypothesis that tissue damage responses—such as from TLR3—and RA might act in overlapping contexts.

In support of a connection between TLR3 and RA pathways is an overlap in known signaling proteins. For example, Signal transducer and activator of transcription 3 (STAT3) and nuclear factor kappa-light-chain-enhancer of activated B cells (NF-kB) stimulate aldehyde dehydrogenase1a3 (ALDH1A3) expression[15], which convert retinaldehyde to RA. Given that STAT3 and NF-kB are essential downstream targets in TLR3 signaling, this implies that TLR3 activation may stimulate RA synthesis. Therefore, the present inventors hypothesized that damage might induce the release of double stranded RNA (dsRNA) that activates TLR3 and its downstream pathways to induce RA synthesis and signaling to promote regeneration in its capacity as a known morphogen. The present objective was to test whether this occurs during WIHN. Here, the present inventors demonstrate that indeed TLR3 is necessary and sufficient for RA synthesis, and that RA signaling is necessary for WIHN. The present inventors provide evidence in both humans and mice that a dsRNA-RA axis is a conserved pathway for promoting rejuvenation or regeneration.

SUMMARY OF THE INVENTION

The present invention is based, at least in part, on the discovery that retinoic acid works synergistically with a TLR3 agonist (e.g., dsRNA) to promote skin rejuvenation. In particular embodiments, the compositions of the present invention are administered in sequential order of retinoic acid or derivatives thereof first and then a TLR3 agonist (e.g., dsRNA).

In one aspect, the compositions and methods of the present invention can be used for cosmetic purposes, particularly, skin rejuvenation. In one embodiment, the compositions and methods of the present invention are used to remove or reduce blotches/pigment. In another embodiment, the compositions and methods of the present invention are used to remove or reduce scars.

In a specific embodiment, a method for treating wrinkles in a subject comprises the steps of (a) administering to the area of the subject comprising a wrinkle a composition comprising an effective amount of retinoic acid or a derivative thereof; and administering to the area of the subject comprising a wrinkle a composition comprising an effective amount of a toll-like receptor 3 (TLR3) agonist. In certain embodiments, the retinoic acid or derivative thereof comprises all-trans retinoic acid. In particular embodiments, the TLR3 agonist comprises double-stranded ribonucleic acid (dsRNA). In a specific embodiment, the dsRNA comprises polyinosinic:polycytidylic acid (Poly I:C). In certain embodiments, the compositions are administered topically. In other embodiments, the compositions are administered by injection.

In another specific embodiment, the present invention provides a method for stimulating hair follicle neogenesis in a subject comprising the steps of (a) administering to the subject a composition comprising an effective amount of retinoic acid or a derivative thereof; and administering to the subject a composition comprising an effective amount of a TLR3 agonist. In further embodiments, the method further comprises administering a composition comprising an effective amount of LL-37. In one embodiment, the subject has alopecia. In another embodiment, the subject is bald. In a further embodiment, the subject has a wound. In certain embodiments, the retinoic acid or derivative thereof comprises all-trans retinoic acid. In particular embodiments, the TLR3 agonist comprises double-stranded ribonucleic acid (dsRNA). In a specific embodiment, the dsRNA comprises polyinosinic:polycytidylic acid (Poly I:C). In certain embodiments, the compositions are administered directly to a site on the subject that requires hair follicle neogenesis. In some embodiments, the compositions are administered topically. In other embodiments, the compositions are administered by injection.

In certain embodiments, the compositions comprising dsRNA further comprise cell-based nucleotides (e.g., dsRNA within a nuclear preparation).

In certain embodiments, the TLR3 agonist comprises HILTONOL®, AMPLIGEN® or RIBOXXOL®. In another embodiment, the TLR3 agonist comprises IPH3102. In particular embodiments, the retinoic acid or derivative thereof comprises ATRAGEN®, AVITA®, RENOVA®, RETIN-A®, VESANOID®, VITINOIN®, Lipo ATRA, Tretinoin Liposomal, AR-623, or TRETINOIN®. Other examples of TLR3 agonists and retinoic acid or derivatives thereof are described herein.

BRIEF DESCRIPTION OF THE FIGURES

FIG. 1A-1G. dsRNA and RA cellular response signatures overlap. FIG. 1A, 1550 nm non-ablative fractional laser treatment improves photoaging. FIG. 1B-1C: 7 days after laser treatment, among the most induced transcripts are the OAS family (OAS1, 2, 3, & L) and enzymes in RA pathway (RDH16, RAET1E, DHRS9) (FIG. 1B); unsupervised upstream regulator analysis confirms strong signatures for dsRNA and Retinoic Acid (RA) induced signaling (FIG. 1C). FIG. 1D-1E: Venn diagrams show high overlap in comparisons of top ranked 100 upregulated and downregulated transcripts (FIG. 1D; from 49,395) or proteins (FIG. 1E; from 3814) between RA- and dsRNA (Poly (I:C))-treated keratinocytes. FIG. 1F: Gene ontology analysis of overlap proteins in FIG. 1E. FIG. 1G: Keratinocyte genes upregulated with dsRNA depend on the dsRNA receptor TLR3, but also RARG. Depicted are mRNAs, and western protein analysis of KRT19. (n=3-4 independent experiments, ***P<0.001, *P<0.05, one-way ANOVA). Data are means±SEM.

FIG. 2A-2I. dsRNA and TLR3 are sufficient and necessary to stimulate RA accumulation. FIG. 2A: A single injection of Poly (I:C) induces Wound Induced Hair Neogenesis (WIHN) as seen by Confocal scanning laser microscopy (CLSM) images and quantified averages. Red dashed lines indicate area of WIHN (n=5 independent animals, P<0.01, unpaired student t-test). FIG. 2B-2C: In LC-MS/MS analysis, Poly (I:C) increases RA levels in cell pellet lysates of human scalp keratinocytes) compared to an RA standard (FIG. 2B), and is substantial across replicates (FIG. 2C, n=3 independent experiments, *P<0.001, paired student t-test). FIG. 2D: Poly (I:C)-mediated RA synthesis is dependent on TLR3 (n=3 independent experiments, P<0.01, one-way ANOVA). FIG. 2E: Poly (I:C) induced RA accumulation requires TLR3 receptor downstream signaling (n=4-7 independent experiments, *P<0.001, one-way ANOVA). FIG. 2F: Recombinant human IL6 induces RA accumulation in human scalp keratinocytes (n=3 independent experiments, *P<0.001, one-way ANOVA). FIG. 2G: Lack of WIHN in Tlr3$^{-/-}$ mice. Red dashed lines indicate area of WIHN (n=6, *P<0.001, unpaired student t-test). FIG. 2H-2I. Tlr3$^{-/-}$ mice have less RA in unwounded (FIG. 2H) (n=4, P<0.01, unpaired student t-test) or wounded skin (FIG. 2I) (n=4 independent animals, *P<0.001, one-way ANOVA), and are resistant to Poly (I:C) induced RA accumulation. Data are means±SEM.

FIG. 3A: RA induces active β-catenin (ABC) expression in keratinocytes of Tlr3$^{-/-}$ mice, while the pan-RAR antagonist BMS493 inhibits induction. Representative western blot (top) and quantitation (bottom), normalized to total β-catenin. (n=3 independent experiments, *P<0.05, paired student t-test). FIG. 3B: RA induces Krt15 and Krt19 expression in keratinocytes of Tlr3$^{-/-}$ mice, while BMS493 substantially inhibits expression. Representative western blot (top) and quantitation of Krt15 (bottom left) and Krt19 (bottom right), normalized to β-Actin. (n=3 independent experiments, *P<0.05, paired student t-test). FIG. 3C: RA induces prominent Krt15 (green) in Tlr3$^{-/-}$ wounds as detected by immunostaining (left) and quantitated (right; n=3 independent animals, ***P<0.001, paired student t-test). White dashed lines indicate basement membrane. Nuclei stained with DAPI (blue). White scale bar=100 μm. FIG. 3D: RA induces WIHN in Tlr3$^{-/-}$ mice as detected by CLSM (top), H&E staining (middle) and quantification (right; n=6-11 independent animals, *P<0.05, unpaired student t-test). Black arrows and dashed lines signify the boundary between unwounded and wounded area. Red dashed lines indicate area of WIHN. Black scale bar=100 N; normal unwounded skin. FIG. 3E: Exogenous RA treatment increases RA levels in Tlr3$^{-/-}$ mice (n=9 independent animals, **P<0.01, paired student t-test). FIG. 3F: Gene Ontology analysis of the top and bottom 100 transcripts after RA treatment to Tlr3$^{-/-}$ mice. Data are means±SEM.

FIG. 4A: RA and Poly (I:C) synergistically induce ALDH1A2 and A3 transcription, but not A1 as detected by qRT-PCR in human scalp keratinocytes. (n=3 independent experiments, *P<0.05, paired student t-test). Western blot staining shows ALDH1A3 induced by RA and Poly (I:C) (n=2). FIG. 4B: Genetic (left; siRNA) or chemical (right; DEAB compound) inhibition of ALDH1A2/A3 decrease the ability of Poly (I:C) to induce KRT15 and KRT19 in human keratinocytes as detected by western blotting (n=2 independent experiments). FIG. 4C: Genetic inhibition of ALDH1A2/A3 in human keratinocytes reduces RA synthesis in presence of Poly (I:C) (n=3 independent experiments, *P<0.05, one-way ANOVA). FIG. 4D: TLR3 and its downstream mediators are required for stimulation of ALDH1A3 in human scalp keratinocytes (n=3 independent experiments). FIG. 4E: Expression of Aldh1a2 and Aldh1a3 in WT mice during wound healing (n=3-4 independent animals, *P<0.05, unpaired student t-test). FIG. 4F: Aldh1a3 but not Aldh1a2 is induced in wild type mice by Poly (I:C) in early wounds; neither is induced in the Tlr3$^{-/-}$ mice as detected by qRT-PCR (n=3 independent animals, *P<0.05, paired student t-test). FIG. 4G: Schematic of sampling procedure (top). Before morphogenesis, the center (C; high future regeneration) of the wound has more RA than the edge (E; lower future regeneration) and accumulates more RA in response to Poly (I:C) in wild type (left) but not Tlr3$^{-/-}$ mice (right) as measured by LC-MS/MS (right; n=4 independent animals, *P<0.05, paired student t-test). White solid box indicates wounded area and red dashed lines signify center region of wound-healed skin. FIG. 4H: Before morphogenesis, the center of the wound expresses more Aldh1a3, Krt15, and Krt19 than the edge in WT mice (n=3 independent animals). FIG. 4I: Increased RA pathway proteins in proteomic analysis of the C vs. E of the wounded skin prior to morphogenesis (n=3 independent animals). *Indicates factors for RA pathway. Data are means±SEM.

FIG. 5A-5B: Chemical inhibition of RARs (BMS493) decreases RA (left)- and Poly (I:C) (right)-induced KRT15 and KRT19 expression in human scalp keratinocytes as detected by western blot with quantitation (n=3 independent experiments, *P<0.05, paired student t-test). FIG. 5C: Immunostaining of KRT15 (green), KRT19 (red) and nuclei (DAPI; blue). *Represents co-stained cells of KRT15 and KRT19. White scale bar=100 μm. FIG. 5D: BMS493 inhibited Krt15 and Wnt7b expression in healing wounds as detected by immunostaining. White dashed lines and arrows separate normal and wounded areas. White arrow heads indicate hair follicles (HF) in normal skin. White scale bar=100 μm. FIG. 5E: BMS493 treatment inhibited WIHN, in untreated or Poly (I:C)-treated WT mice. Red dashed lines indicate area of WIHN. (n=5 independent animals, *P<0.05, paired student t-test). FIG. 5F-5H: Conditional epithelial specific deletion of Rarα (FIG. 5G; n=4-9 independent animals, *P<0.05, paired student t-test) and global deletion of Rarα (FIG. 5H; n=4-11 independent animals, *P<0.05, paired student t-test) both inhibit baseline and Poly (I:C) augmented WIHN, while epithelial deletion of Rarg has minimal effects (FIG. 5F). Red dashed lines indicate area of WIHN. FIG. 5I: Rejuvenating fractional ablative $CO_2$ laser induces RA synthesis in human scalp (n=3 independent human samples, *P<0.05, paired student t-test; bottom). Clinical photos (top) and H&E histology (middle) of human subjects before and after $CO_2$ laser treatment. Black scale bar=1 mm. Data are means±SEM.

FIG. 6A: Analysis of RA in cultured media in human keratinocytes treated with PBS (control) and Poly (I:C) (n=3 independent experiments, *P<0.001, paired student t-test). FIG. 6B: Analysis of retinol (ROL) in cultured media and cell lysates in human keratinocytes treated with PBS (control) and Poly (I:C) (n=2-3 independent experiments). n.s.; not significant. FIG. 6C: Analysis of retinyl ester (RE) in cultured media and cell lysates in human keratinocytes treated with PBS (control) and Poly (I:C) (n=3 independent experiments). n.s.; not significant. FIG. 6D-6E: Analysis of ROL (FIG. 6D) and RE (FIG. 6E) in human keratinocytes transfected with TLR3 downstream targets in presence of PBS (control) and Poly (I:C) (n=4-6 independent experiments). n.s.; not significant. FIG. 6F-6G: Analysis of ROL (FIG. 6F) and RE (FIG. 6G) in human keratinocytes treated with recombinant human IL6 (n=3 independent experiments, P<0.01, on-way ANOVA). FIG. 6H-6I: Analysis of ROL (FIG. 6H) and RE (FIG. 6I) in unwounded skin of WT and Tlr3-/- mice (n=4 independent animals). n.s.; not significant. FIG. 6J-6K: Analysis of ROL (FIG. 6J) and RE (FIG. 6K) in wounded skin of WT and Tlr3-/- mice treated with PBS (control) and Poly (I:C) (n=4-5 independent animals). n.s.; not significant. Data are means±SEM.

FIG. 8A: Relative mRNA expression of TLR3, WNT7b, SOX9, LHX2, KRT15, EDAR, LGR5, and KRT19 in human scalp keratinocytes with RA and/or Poly (I:C). (n=5 independent experiments, *P<0.05 and **P<0.01, one-way ANOVA). FIG. 8B: Immunostaining results of TLR3 (green), KRT15 (green), and KRT19 (red) in human scalp keratinocytes with RA and/or Poly (I:C). Nucleus was stained by DAPI (blue). FIG. 8C: Human whole skin explants treated as above and stained for KRT15 (green), TLR3 (red) and WNT7b (green). White Scale bar: 100 μm. Note suprabasal staining of KRT15/TLR3 and confluent basal layer staining of WNT7b in combination treatment. FIG. 8D: Immunostaining results of Krt15 (green) in wounded skin of WT mice at Day 11 after wounding. Nucleus was stained by DAPI (blue). White arrow indicates the edge between wounded and unwounded skin. White dashed line indicates areas with new hair follicles. White Scale bar: 100 μm. Data are means±SEM.

FIG. 9A-9D. WIHN in Rar-alpha and gamma double knockout mice and analysis of vitamin A metabolites in human subjects. FIG. 9A: Skin specific Rarα and Rarg double knockout mice fail to regenerate hair follicles (n=4 independent animals, ***P<0.001, paired student t-test). Red square indicates areas with new hair follicles. FIG. 9B: Intensity of RA in human subjects with CO2 laser treatment. FIG. 9C-9D: Analysis of ROL (FIG. 9C) and RE (FIG. 9D) in human subjects with CO2 laser treatment. (n=3 independent human samples), n.s.; not significant. Data are means±SEM.

FIG. 11A: Confocal image of WT wounded skin with ethanol (EtOH) and RA treatment. FIG. 11B: Quantified WIHN results (EtOH; n=5, RA; n=9 independent animals). Red square indicates areas with new hair follicles. n.s.; not significant. Data are means±SEM.

FIG. 12A-12E. Hair follicle regeneration, Vitamin A, and its metabolites in MDA5-/- and RIG-I-/- mice. FIG. 12A: WIHN results of strain-matched WT (n=9 independent animals) and RIG-I-/- (n=17 independent animals) mice (*P<0.05, unpaired student t-test). Red square indicates areas with new hair follicles. FIG. 12B: WIHN results of WT and MDA5-/- mice treated with PBS (control) and Poly (I:C) (n=4-5 independent animals, *P<0.05, unpaired student t-test). Note that Poly (I:C) induces hair follicle regeneration in MDA5-/- mice similar to WT. FIG. 12C-12E: Analysis of RA (FIG. 12C), ROL (FIG. 12D), and RE (FIG. 12E) in human keratinocytes transfected with scrambled-, MDA5-, and RIG-I-siRNA in presence of PBS (Control) and Poly (I:C) (n=4-7 independent experiments, ***P<0.001, one-way ANOVA), n.s.; not significant. Data are means±SEM.

FIG. 13A: Rnase1$^{-/-}$ mice exhibit increased wound induced hair neogenesis (WIHN) with or without the presence of poly (I:C) (confocal scanning laser microscopy, CSLM, images; n=10 each, p<0.0001). In each image, the dash red box indicates the area of hair follicle regeneration. FIG. 13B: Grossly, Rnase1$^{-/-}$ mice display improved wound closure speed. FIG. 13C: Quantification of FIG. 2B according to wound area (n=3, p<0.05).

FIG. 14A: Quantitation and analysis of retinoic acid (RA) levels demonstrate more RA is present in Rnase1-/- compared to wild-type mice in unwounded skin (n=4, p<0.05). Measurements were acquired via LC-MS. FIG. 14B: Quantitation and analysis of retinol (ROL) levels in unwounded skin of wild-type and Rnase1-/- mice does not show a similar change (n=4, p=n.s.). FIG. 14C: Quantitation and analysis of retinyl ester (RE) levels in unwounded skin of wild-type and Rnase1-/- mice is not significant (n=4, p<n.s.).

DETAILED DESCRIPTION OF THE INVENTION

Figure 1A:
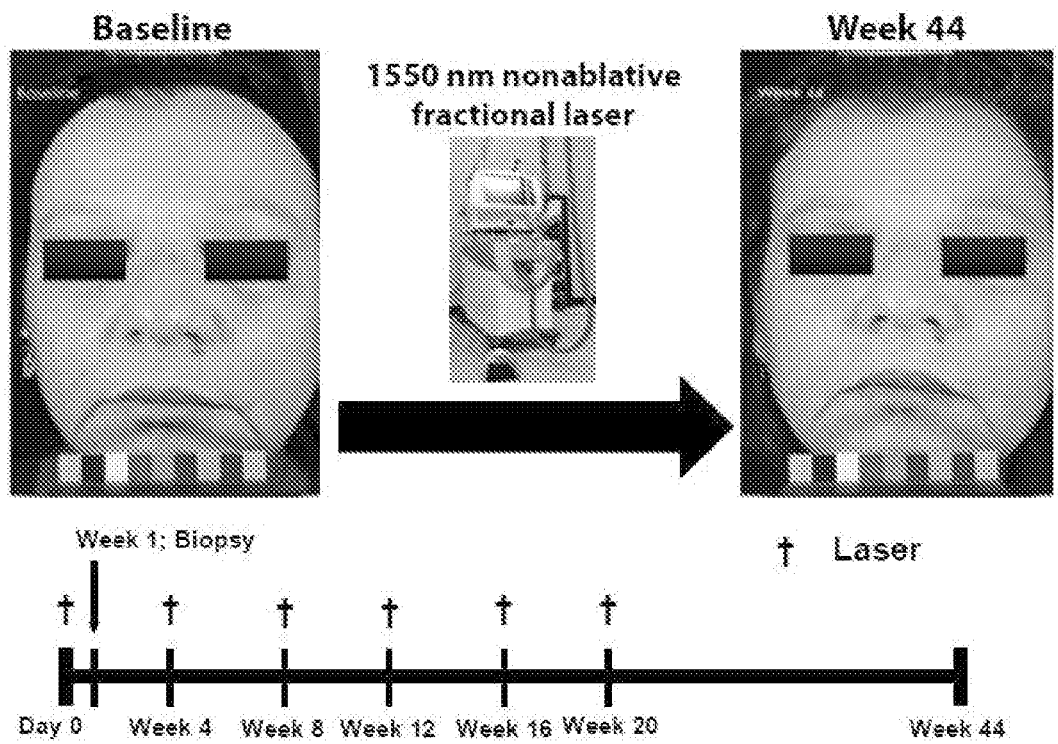

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Where "about" is used in connection with a number, this can mean the number+/−15%, the number plus 5%, or the number itself without "about." For example, "about 100" would stand for "from and including 85 to and including 115". Where "about" is used in connection with numeric ranges, for example "about 1 to about 3", or "between about one and about three", preferably the definition of "about" given for a number in the last sentence is applied to each number defining the start and the end of a range separately. In certain embodiments, where "about" is used in connection with any numerical values, the "about" can be deleted.

As used herein, the terms "patient", "subject" and "subjects" refer to an animal, preferably a mammal including, but not limited to, a non-primate (e.g., a cow, pig, horse, cat, dog, rat, and mouse) and a non-human primates (e.g., a monkey such as a cynomolgous monkey), and more preferably a human. In a specific embodiment, the subject is a human.

As used herein, the term "effective amount" refers to the amount of an agent (e.g., a prophylactic or therapeutic agent) which is sufficient to cause the desired effect in the particular context, such as stimulate and/or enhance skin rejevunation, induce/enhance TLR3/RA expression/activity in a cell, induce TLR3/RA-mediated signaling in a cell, prevent, reduce or ameliorate the severity, duration and/or progression of a disease or condition or one or more symptoms thereof, ameliorate one or more symptoms of a disease or condition, prevent the advancement of a disease or condition, cause regression of a disease or condition, prevent the recurrence, development, or onset of a disease or condition or one or more symptoms thereof, or enhance or improve the prophylactic or therapeutic effect (s) of another therapy (e.g., prophylactic or therapeutic agent).

In certain embodiments, the compositions and methods described herein can be used for cosmetic purposes, particularly "skin rejuvenation." Generally, skin rejuvenation refers to the removal or reduction of blotches/pigment, scars, wrinkles, large pore size or lines in the skin, particularly the face. In particular embodiments, the present invention relates to rejuvenation of facial superficial and dermal layer rejuvenation of facial skin to reverse, alleviate or delay normal aging processing and, in particular, to a non-surgical method for rejuvenation of facial skin. Rejevunation can also refer to regrowth of hair including, but not limited to, in areas of alopecia.

The term "specifically binds to" or "selectively binds to" means that a compound (e.g., dsRNA) can bind preferably in a competitive binding assay to the binding partner, e.g., TLR3. Competitive binding assays and other methods for determining specific or selective binding known in the art.

The term "TLR3 agonist" refers to an affinity agent (e.g., a molecule that binds a target molecule) capable of activating a TLR3 polypeptide to induce a full or partial receptor-mediated response. An agonist of TLR3 may induce any TLR3 activity, for example TLR3-mediated signalling, either directly or indirectly. A TLR3 agonist, as used herein, may but is not required to bind a TLR3 polypeptide, and may or may not interact directly with the TLR3 polypeptide. A TLR agonist can also be a small molecule. Examples of TLR3 agonists/enhancers include, but are not limited to, dequalinium dicholoride, ivermectin, entandrophragmin, GW9662, P1,P4-Di(adenosine-5)tetraphosphate triammonium, and astaxanthin.

As employed herein, the phrases "selective TLR3 agonist" and "TLR3 agonist which selectively induces TLR3 activity" refer to compositions which induce TLR3-mediated signalling to a significantly greater extent than signalling by one or more other dsRNA receptors. When the TLR3 agonist is a dsRNA composition, a "TLR3 agonist which selectively induces TLR3 activity" refers to compositions which induce TLR3-mediated signalling to a significantly greater extent than signalling by one or more other dsRNA receptors (e.g., TLR7, RIGI, MDA-5, PKR and/or other dsRNA receptors). In one embodiment, "significantly greater extent," as applied to interaction between TLR3 agonist and a receptor, refers to agonists which have a significantly higher therapeutic index (i.e., the ratio of efficacy to toxicity) for treatment of the target disease state or condition than for activation of pathways mediated by other receptors. The toxicity of therapeutic compounds frequently arises from the non-selective interaction of the therapeutic compound with other receptors. Thus, the present invention provides a means to reduce the incidence of side-reactions commonly associated dsRNA therapy. Preferably, a composition which induces TLR3-mediated signalling to a significantly greater extent than signalling by other another receptor(s) will have an EC50 for induction of TLR3 signalling that is less than the EC50 for signalling by the other receptor(s).

"PolyI", "polyC", "polyA", "polyU", mean polyinosinic acid, polycytidylic acid, polyadenylic acid, and polyuridylic acid, respectively, each optionally substituted with other monomers.

"PolyAU", used interchangeably with "pApU", "polyA:U", poly(A):poly(U), means an at least partially double stranded molecule made of polyadenylic acid(s) and polyuridylic acid(s), each optionally substituted with other monomers so long as the biological function (e.g., immunomodulatory activity, TLR3 agonism or binding) is preserved.

A "homopolymer" is a polymer made of substantially only a single monomer; for example a polyA homopolymer is substantially all A (adenosine) monomers. A homopolymer can be a single longer polymer or can consist of a plurality of shorter polymers concatenated (e.g., using a linker) to form a longer polymer, etc.

A "copolymer" is a polymer made of two or more monomers; for example a poly A copolymer comprises A (adenosine) monomers and one or more monomers other than adenosine.

The term "poly AxU" mean copolymer of adenylic acid and uridylic acid where one uridylic acid is substituted for about every x adenylic acids, respectively. For example "poly C12U" is a copolymer of cytidylic acid and uridylic acid where one uridylic acid is substituted for about every 12 cytidylic acids, respectively.

"dsRNA" and "double-stranded RNA" refer to complexes of polyribonucleotides which are at least partly double stranded. dsRNA need not be double stranded over the length of the molecule, nor over the length of one or more of the single-strand nucleic acid polymers that form the dsRNA. According to the invention, "dsRNA" means double-stranded RNA and is RNA with two partially or completely complementary strands. The size of the strands may vary from 6 nucleotides to 10000, preferably 10 to 8000, in particular 200 to 5000, 200 to 2000 or 200 to 1000 nucleotides. In certain embodiments, the dsRNA is polyinosinic-polycytidylic acid (poly(I:C)), a synthetic analog of dsRNA. Poly(I:C) is composed of a strand of poly(I) annealed to a strand of poly(C). In particular embodiments, the TLR3 agonist dsRNA comprises RIBOXXOL® (Riboxx GmbH (Dresden, Germany)). The dsRNA can be a fully or partially (interrupted) pair of RNA hybridized together. It can be made for example by mixing polyinosinic and polycytidylic acid RNA molecules. It also can be made by mixing defined fully or partially pairing non-homopolymeric RNA strands.

There is no specific ribonucleotide sequence requirement for the dsRNA molecules to be suitable for preparing a composition of the present invention.

The term "base pair" (abbreviated as "bp") frequently used to indicate the molecular size of nucleic acid is used to indicate the molecular size by the numbers of bases in the nucleic acid (i.e., 10 bp means the double strand polymer having ten bases) in each complementary strand.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "human-suitable" when referring to an agent or composition refers to any agent or composition that can be safely used in humans for, e.g., the therapeutic methods described herein. For example human suitable agents do not cause effects such as severe cytokine induction at a level that would preclude their use in humans, or contain levels of substances (e.g., endotoxins) that are incompatible with use in humans, in the particular context (e.g., mode of administration) in which the agent is used.

An "isolated" or "purified" preparation (e.g., dsRNA preparation) is substantially free of material or other contaminating compounds from the source from which the preparation (e.g., dsRNA) is derived, or substantially free from chemical precursors or other chemicals when chemically synthesized. "Substantially free" means that a preparation of dsRNA is at least 50% pure (wt/wt). In a preferred embodiment, the preparation of dsRNA has less than about 20%, 10%, 5% and more preferably 2% (by dry weight), of free ribonucleotide monomers, proteins or chemical precursors and/or other chemicals, endotoxins, and/or free ssRNA (in the case of a dsRNA preparation), e.g., from manufacture. These also referred to herein as "contaminants". Examples of contaminants that can be present in a dsRNA preparation provided herein include, but are not limited to, calcium, sodium, ribonucleotide monomers, free ssRNA (in the case of a dsRNA preparation), endotoxin, polynucleotide phosphoylase enzyme (or other enzyme having similar substrate specificity), methanol, ethanol, chloride, sulfate, dermatan sulfate, and chondrotin sulfate. Purity and homogeneity are typically determined using analytical chemistry techniques such as polyacrylamide gel electrophoresis or high performance liquid chromatography.

The term "cathelicidins" refers to cationic peptides that have broad-range antimicrobial activity. Zanetti, M. et al. *J. Biol. Chem.* 268, 522 (1993). These peptides belong to the family of anti-microbial peptides which form part of the host's important innate immunity mechanism. Lehrer, R. and T. Ganz. *Curr. Opin. Immunol.* 11, 23 (1999). In humans, cathelicidins and defensins are expressed in immune cells and at epithelial surfaces. See Chromek, M. et al. *Nature Medicine* 12, 636 (2006); Zanetti, M. *J. Leukoc. Biol.* 75, 39 (2004); and Ganz, T. *Nat. Rev. Immunol.* 3, 710 (2003). hCAP18, human cationic antimicrobial protein, with a MW of 18 kD, is the only cathelicidin gene found in humans. Lehrer, R. and T. Ganz. *Curr. Opin. Immunol.* 11, 23 (1999). The N-terminus of this protein consists of a cathelin-like region (similar to the other members of the cathelicidin family) and a C-terminal termed LL-37. See Sorensen, O E. et al. *Blood* 97, 3951 (2001); and Zanetti, M. et al. *FEBS Lett* 374, 1 (1995). An amphipathic alpha-helical peptide, LL-37 plays an important role in the first line of defense against local infection and systemic invasion of pathogens at sites of inflammation and wounds. Cytotoxic to both bacterial and normal eukaryotic cells, LL-37 is significantly resistant to proteolytic degradation in solution. See Neville, F. et al. *Biophys. J.* 90, 1275 (2006); and Oren, Z., et al. *Biochem. J.* 341, 501 (1999).

Examples of cathelicidins include LL-37/hCAP18 (LL-37) in humans (Curr Drug Targets Inflamm Allergy. 2003 September; 2(3):224-31; Eur J. Biochem. 1996 Jun. 1; 238(2):325-32; Paulsen F et al., J. Pathol. 2002 November; 198(3):369-77). LL-37 is a 37 amino acid residue peptide corresponding to amino acid residue coordinates 134-170 of its precursor hCAP18/human cathelicidin antimicrobial peptide protein (GenBank: Accession NP004336; version NP004336.2 GI:39753970; REFSEQ: accession NM004345.3). LL-37 comprises the amino acid sequence LLGDFFRKSKEKIGKEFKRIVQRIKDFLRN LVPRTES (SEQ ID NO:1). The term LL-37 also includes sequences having at least 90% identity with SEQ ID NO:1. In particular, the term includes sequences having one or more conservative amino acid substitutions of SEQ ID NO:1. Cathelcidins including LL-37 can be used in the methods and composition described herein alone or in combination with dsRNA or other TLR3 agonists to enhance rejuvantion.

II. DS-RNA TLR3 Agonist

Double-stranded (ds) RNA (ribonucleic acid) is chemically very similar to DNA (deoxyribonucleic acid). It is also a long molecule containing nucleotides linked together by 3'-5' phoshodiester bonds. Two differences in its chemical groups distinguish dsRNA from DNA. The first is a minor modification of sugar component. The sugar of DNA is deoxyribose, whereas RNA contains ribose, which is identical to deoxyribose except for the presences of an additional hydroxyl group. The second difference is that RNA contains no thymine, but instead contains the closely related pyrimidine, uracil. DsRNA forms from the hybridization of two complementary polyribonucleotides forming a double helix similar to that of DNA. The two strands of the double helix are held together by hydrogen-bonded base pairs.

TLR3 is a receptor for a form of immunity called "innate immunity" which recognizes double-stranded RNAs with a minimum size of at least 50 base pairs. The size requirement or discrimination of dsRNA by TLR3 prevents responses to non-microbial sources of dsRNA micro (mi) RNA or transfer (t) RNA. TLR3 exists as a horseshoe shaped monomer with an N-terminal, ligand-binding extra-cytoplasmic domain (ECD), a transmembrane domain (TMD), and a C-terminal cytoplasmic signaling domain (CSD). X-ray crystallographic studies have provided structural data for the TLR-3 ligand complex which consists of a TLR3 homodimer complexed to dsRNA of at least about 50 consecutive base pairs. The formation of the complex is believed to transmit a conformational change in the CSD via the TMD connector that allows cytoplasmic signaling. Above 50 base pairs, binding affinity is a function of size with a progressive increase in binding affinity with increased length in linear non-branched dsRNA. The minimum size for dsRNA is about 40 nucleotides.

The double-stranded ribonucleic acid (dsRNA) may be fully hybridized strands of poly(riboinosinic acid) and poly(ribocytidilic acid) (i.e., polyIC) or poly(riboadenylic acid) and poly(ribouracilic acid) (i.e., polyAU). If mismatched, the dsRNA may be of the general formula $rI_n \cdot r(C_{4-29}U)_n$, which is preferably $rI_n \cdot r(C_{12}U)_n$, in which r indicates ribonucleotides. It is preferred that n is an integer from about 40 to about 40,000. For example, a strand of poly(riboinosinic acid) may be partially hybridized to a strand of poly(ribocytosinic$_{4-29}$uracilic acid). Other mismatched dsRNA that may be used are based on copolynucleotides such as poly$(C_mU)$ and poly$(C_mG)$ in which m is an integer from about 4 to about 29 or analogs of a complex of poly(riboinosinic acid) and poly(ribocytidilic acid) formed by modifying the $rI_n \cdot rC_n$ to incorporate unpaired bases (uracil or guanine) in the polyribocytidylate $(rC_m)$ strand. Alternatively, mismatched dsRNA may be derived from r(I)r(C) dsRNA by modifying the ribosyl backbone of poly(riboinosinic acid) $(rI_n)$, e.g., by including 2'-O-methyl ribosyl residues. Of these mismatched dsRNA analogs of $rI_n rC_n$, the preferred ones are of the general formula $rI_n \cdot r(C_{11-14}U)_n$ or $rI_n \cdot r(C_{29},G)_n$ (see U.S. Pat. Nos. 4,024,222 and 4,130,641; which are incorporated by reference). The dsRNA described therein generally are suitable for use according to the present invention. See also U.S. Pat. No. 5,258,369.

The dsRNA may be complexed with an RNA-stabilizing polymer such as polylysine, polylysine plus carboxy-methylcellulose, polyarginine, polyarginine plus carboxymethylcellulose, or any combination thereof. Other examples of mismatched dsRNA for use in the invention include, but are not limited to, $r(I) \cdot r(C_4,U)$; $r(I) \cdot r(C_7,U)$; $r(I) \cdot r(C_{13},U)$; $r(I) \cdot r(C_{22},U)$; $r(I) \cdot r(C_{20},G)$; and $r(I) \cdot r(C_{29},G)$. Mismatched dsRNA may also be modified at the molecule's ends to add a hinge(s) to prevent slippage of the base pairs, thereby conferring a specific bioactivity in specific solvents or aqueous environments which exist in human biological fluids.

Poly-ICLC (interchangeably known as Hiltonol® or poly-IC:LC, among others) is a high molecular weight derivative of poly-IC stabilized with poly L-lysine and carboxymethylcellulose (CMC) that have been added to improve the pharmacokinetic properties of poly-IC. Poly-ICLC therefore has a formula of ln.Cn-poly-1-lysine-5 carboxymethylcellulose. See U.S. Pat. No. 4,349,538. Carboxymethylcellulose is a negatively charged (at neutral pH), hydrophilic material used to maintain the solubility of the complex. PolyICLC is more resistant to nucleases than poly-IC with a 27,000 KDa or larger complex of poly-ICLC being particularly resistant to nucleases.

In specific embodiments, the dsRNA TLR3 agonist is Ampligen®. Ampligen® is a particular dsRNA denoted Poly I:Poly $C_{12}U$, wherein one of the two polyribonucleotides is polyriboinosinic acid and the other is polyribocytidylic$_{12}$, uridylic acid. Thus, the pyrimidine building blocks of Ampligen® are present in a ratio of 12 cytosines of each uracil, while the complementary purine strand contains 13 inosine residues. Within the double-stranded helical structure of Ampligen® the pyrimidine, cytosine, hydrogen bonds with the purine, inosine, while the pyrimidine, uracil, does not form any hydrogen bonds. Therefore, a "mismatch" is created once for every 12 base pairs (bps) formed between the inosine and cytosine residues. In contrast to Ampligen®, Poly I:Poly C contains only complementary inosine:cytosine base pairs. No uracil is present in Poly I:Poly C and there are no mismatches.

Other agonists of TLR3 that may be useful in embodiments of the invention include Poly-ICR (Poly IC (Polyriboinosinic-polycytidylic acid)-Poly arginine (Nventa Biopharmaceuticals Corporation); high MW synthetic dsRNA IPH31XX compounds, for example IPH3102, which in humans are specific for TLR3 (Innate Pharma S.A; Schering-Plough Corporation); Oragens™, for example Oragen™ 0004, Oragen™ 0033 and Oragen™ 0044 (Temple University); and NS9, a complex of polyinosinic-polycytidylic acid (Nippon Shinyaku Co., Ltd). The Oragen™ compounds are synthetic analogues of naturally occurring 2',5'-oligoadenylate analogues, wherein the analogues are typically conjugated to a carrier molecule to enhance cellular uptake (see U.S. Pat. No. 6,362,171). In particular embodiments, the TLR3 agonist dsRNA comprises RIBOXXOL® (Riboxx GmbH (Dresden, Germany)).

PCT Publication No. WO 2009/130616 (Innate Pharma) describes high MW polyAU dsRNA molecules that are TLR3 agonists. PCT Publication Nos. WO 2006/054177, WO 2006/054129, WO 2009/130301 and WO 2009/136282 (Institut Gustave Roussy) describe the use of dsRNA TLR3 agonists for treating cancer.

Further embodiments are also disclosed in WO 2007/089151, which describes stathmin and stathmin-like compounds that are TLR3 agonists. In a specific embodiment, a nucleic acid-based agonist is coupled to one of these stathmin or stathmin-like agonists.

In another embodiment, the dsRNA TLR4 agonist is rugged dsRNA. Rugged dsRNA is a novel form of dsRNA with a unique composition and physical characteristics. Unlike the previously known antiviral, Ampligen® (Poly I:Poly C$_{12}$U), the new and improved form of Rugged dsRNA (e.g., Poly I:Poly C$_{30-35}$U (preferably, Poly I:Poly C$_{30}$U), wherein PolyC$_{30-35}$U, indicates a ratio, that is, that for every U there are 30-35 C's), has an increased Ruggedness characterized by an increase resistance to thermal denaturation and ribonuclease digestion. This improved form of dsRNA also has a reduced tendency to form branched dsRNA molecules which results in increased bioactivity due to an increased ability to bind TLR3 receptor. The minimal length of Rugged dsRNA (termed the monomer unit) is about 50 base pairs requiring about 4 to 5 (e.g., 4.7) helical turns (10.7 base pairs are required for each complete turn of the helix) within its dsRNA structure and represents the smallest or monomeric unit of Poly I:Poly C$_{30}$U, approximately 24,000 to 30,000 Daltons (a Dalton is a unit of weight equal to the weight of a single hydrogen atom). The maximal length of Rugged dsRNA is about 500 base pairs composed of about 10 monomer units, requiring about 50 (e.g., 46.7) helical turns and having a molecular weight of approximately 300,000 Daltons (e.g., about 225,000 Daltons). See U.S. Patent Application Publication No. 20120009206.

The present invention also provides compositions and methods for promoting dsRNA formation. In particular embodiments, yeast RNA is used. Yeast RNA (e.g., Baker's yeast (Sigma Catalog No. R6750-1G) and Torula Yeast (Sigma Catalog No. R6625-25G) can be heated and cooled to promote dsRNA formation.

In further embodiments, dsRNA can be chemically modified to provide more stability. Chemical modifications of RNA to enhance permanence include, but are not limited to, phosphorothionate (PS) (backbone modification); 2'-O-methyl (2'-OMe), 2'-fluoro (2'-F), 2'-O-methoxyethyl (2'-MOE) (sugar modifications); 2'-O,4'-C-methylene linked bicyclic riboncleotides (locked nucleic acid (LNA)); and L-RNA (enantiomer of natural RNA) oligonucleotides known as spiegelmers

III Retinoic Acid and Derivatives Thereof

In some embodiments, the "retinoic acid or its derivatives" includes a metabolite of vitamin A (retinol) including, but not limited to, any naturally occurring or synthetic derivatives, selected from tretinoin, isotretinoin, acitretin, tazarotene, tazarotenic acid, adapalene, and pharmaceutically acceptable salts, esters, isomers, enantiomers, active metabolites, and/or prodrugs thereof. For example, in one embodiment, the retinoic acid or its derivatives includes isotretinoin or a pharmaceutically acceptable salt thereof. In another embodiment, the retinoic acid or its derivatives includes acitretin or a pharmaceutically acceptable salt thereof.

"Isotretinoin" refers to isotretinoin in the form of a free acid or its pharmaceutically acceptable salts, such as alkali metal salts. Isotretinoin is 13-cis-retinoic acid. Tretinoin (all-trans retinoic acid) and isotretinoin are geometric isomers and show reversible interconversion in vivo. The administration of one isomer can give rise to another. Other major metabolites of isotretinoin such as 4-oxo-isotretinoin and its geometrical isomer 4-oxo-tretinoin are also contemplated in the term "isotretinoin."

In certain embodiments, the retinoic acid or its derivatives comprises all-trans retinoic acid ("ATRA"). ATRA is one of the active metabolites of Vitamin A (VA). ATRA and associated retinoids are lipophilic molecules that can pass through plasma membranes and enter the nucleus where they bind retinoic acid receptors (RARs). These receptors are members of the nuclear receptor family and can be divided into 2 subgroups, Retinoid Acid Receptor (RAR) and Retinoid X Receptor (RXR). ATRA can bind both but has higher affinity to RAR. Ligation of ATRA to its receptors induces allosteric changes that allow RARs to bind specific DNA recognition sites and regulate gene transcription. The term "ATRA" as used herein refers to all trans retinoic acid or salts of all trans retinoic acid, C1-C10 alkyl esters of all trans retinoic acid, salts of C1-C10 alkyl esters of all trans retinoic acid, C1-C10 alkyl amides of all trans retinoic acid, or salts of C1-C10 alkyl amides of all trans retinoic acid. ATRA is, amongst others, available as ATRAGEN®, AVITA®, RENOVA®, RETIN-A®, VESANOID®, VITINOIN®, Lipo ATRA, Tretinoin Liposomal, AR-623, or TRETINOIN®.

IV. Formulations and Pharmaceutical Compositions

In certain embodiments, the present invention provides a composition comprising a TLR3 agonist. In other embodiments, the present invention provides a composition comprising retinoic acid or derivatives thereof. In further embodiments, the present invention provides a composition comprising a TLR3 agonist and retinoic acid or derivatives thereof In further embodiments, the present invention provides a kit comprising a composition comprising a TLR3 agonist and a composition comprising retinoic acid or derivatives thereof. In certain embodiments, the TLR3 agonist is dsRNA. In particular embodiments, the present invention provides a kit comprising a composition comprising a TLR3 agonist and retinoic acid or derivatives thereof.

In a preferred embodiment, the compositions are administered topically. It is preferable to present the active ingredient, i.e. TLR3 agonist, retinoic acid or derivatives thereof or a combination thereof, as a pharmaceutical formulation. Exemplary compositions are described in detail in the examples which follow. The active ingredient may comprise, for topical administration, from 0.001% to about 20% w/w, by weight of the formulation in the final product, although it may comprise as much as 30% w/w, from about 1% to about 20% w/w of the formulation. The topical formulations of the present invention, comprise an active ingredient together with one or more acceptable carrier(s) therefor and optionally any other therapeutic ingredients(s). The carriers must be "acceptable" in the sense of being compatible with the other ingredients of the formulation and not deleterious to the recipient thereof.

The compositions of the present invention can be administered to a subject either by itself or in pharmaceutical compositions where it is mixed with suitable carriers or excipient(s). In treating a subject exhibiting a disorder of interest, a therapeutically effective amount of an agent or agents such as these is administered. A therapeutically effective dose refers to that amount of the compound that results in amelioration of symptoms or a prolongation of survival in a subject.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, capsules, or solutions. The pharmaceutical compositions of the present invention may be manufactured in a manner that is itself known, e.g., by means of conventional mixing, dissolving, granulating, emulsifying, encapsulating, entrapping or lyophilizing processes.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment with topical formulations, in other aspects of the invention, the composition might be delivered by other methods. For example, a composition might be formulated for parenteral delivery, e.g., for subcutaneous, intravenous, or intramuscular injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. In other embodiments, a composition comprising a TLR3 agonist may be formulated for one type of administration and a composition comprising retinoic acid and derivatives thereof may be formulated for a different type of administration.

Formulations suitable for topical administration include liquid or semi-liquid preparations suitable for penetration through the skin to the site of where treatment is required, such as liniments, lotions, creams, ointments or pastes. Lotions according to the present invention include those suitable for application to the skin. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

For preferred topical delivery vehicles the remaining component of the composition can be water, which is necessarily purified, e.g., deionized water. Such delivery vehicle compositions can contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components.

Other known transdermal skin penetration enhancers can also be used to facilitate delivery of a composition described herein. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle. Indeed, one skilled in the art can easily determine the appropriate dose, schedule, and method of administration for the exact formulation of the composition being used, in order to achieve the desired effective amount or effective concentration of the agent in the individual subject.

The dose of a presently disclosed composition, administered to an animal, particularly a human, in the context of the presently disclosed subject matter should be sufficient to produce at least a detectable amount of a therapeutic response in the individual (e.g., stimulate hair follicle neogenesis) over a reasonable time frame. The dose used to achieve a desired effect will be determined by a variety of factors, including the potency of the particular agent being administered (e.g., a TLR3 agonist), the pharmacodynamics associated with the agent in the host, the severity of the condition in the subject, other medications being administered to the subject, the degree of susceptibility of the individual, the age, sex, and weight of the individual, idiosyncratic responses of the individual, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Accordingly, in certain embodiments, the compositions can be administered/applied at a dose of about 1-100 μg/cm$^2$ including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μg/cm$^2$ area per application.

In a more specific embodiment, the compositions can be administered/applied in a range of about 1-20 μg/cm$^2$ area per application including, but not limited to, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, and 19-20 μg/cm$^2$ area per application.

The pharmaceutical compositions can be administered on a daily basis. In one embodiment, the compositions are administered once a day for 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks or more including 1, 2, 3, 4, 5, 6, 7, 8, 9, 10, 11, or 12 months.

The compositions can be administered once every few days including once every 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The compositions can be administered once a week for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more. Alternatively, the compositions can be administered once every few weeks for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more.

In other embodiments, the compositions can be administered several times in a month including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 times per month.

In particular embodiments, the dose of a composition described herein comprises a range of about 2-10 µg/cm$^2$ area per application, with 1-10 applications separated within one month. In other embodiments, the dosage is about 2-10 µg/cm$^2$ area per application, with 1-3 applications separated within one month.

In certain embodiments, the presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising the presently disclosed compounds. Alternatively, these agents may be part of a single dosage form, mixed together with one or more presently disclosed compounds in a single composition.

By "in combination with" is meant the administration of one or more presently disclosed TLR3 agonists with one or more therapeutic agents (e.g., retinoic acid and derivatives thereof) either simultaneously, sequentially, or a combination thereof. Therefore, a cell or a subject can receive one or more TLR3 agonists and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the one or more TLR3 agonists and one or more therapeutic agents (e.g., retinoic acid and derivatives thereof) are administered simultaneously, they can be administered to the cell or administered to the subject as separate pharmaceutical compositions, each comprising either one or more presently disclosed compounds or one or more therapeutic agents, or they can contact the cell/subject as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Noncoding dsRNA Induces Retinoic Acid Synthesis to Stimulate Hair Follicle Neogenesis Via TLR3

How developmental programs reactivate in regeneration is a fundamental question in biology_ENREF_1. The present inventors addressed this question through the study of Wound Induced Hair follicle Neogenesis (WIHN), an adult organogenesis model where stem cells regenerate de novo hair follicles following deep wounding. The exact mechanism is uncertain. Here the present inventors show that self-noncoding dsRNA activates the anti-viral receptor toll-like receptor 3 (TLR3) to induce intrinsic retinoic acid (RA) synthesis in a concentration differential that predicts new hair follicle formation after wounding in mice. Additionally, in humans, rejuvenation lasers induce gene expression signatures for dsRNA and RA, with measurable increases in intrinsic RA synthesis. These results demonstrate a potent stimulus for RA synthesis by non-coding dsRNA, relevant to their broad functions in development and immunity.

Materials and Methods

Human samples. Hopkins IRBs (NA_0033375, NA_00075350, IRB00028768) and Helsinki principles were followed. Skin was processed as described[29,30] Human biopsies were donated under written informed consent and Hopkins IRB approved protocol (NA_00033375) following Declaration of Helsinki principles. Discarded skin from Mohs surgery or foreskin excisions was used for ex vivo explant experiments and keratinocytes isolation. Skin tissues were prepared for generating paraffin embedded or frozen tissue sections.

Figure 1B:
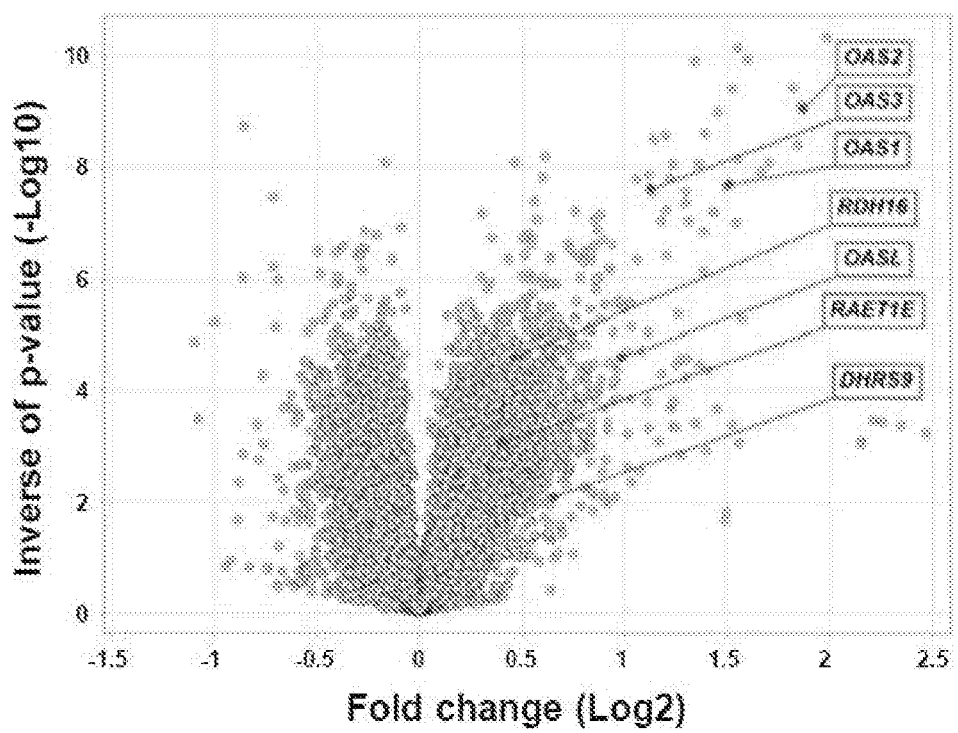

Human Photoaging study. Under Hopkins IRB (IRB00028768) with all relevant ethical regulations for work with human participants, 17 Caucasian women Fitzpatrick types I-III with average age of 55 and moderate to severe baseline photoaging were enrolled after informed consent including permission to publish skin photography in FIG. 1. Laser treatments and biopsy schedule were as listed, with treatments occurring both to the face and arm, and arm biopsies used for gene expression data listed. The authors affirm that human research participants provided informed consent for publication of the images in FIG. 1A.

Human RA measurement study. Under Hopkins IRB (NA_00075350), 3 human subjects with Central Centrifugal Cicatricial Alopecia with large areas of scarring hair loss were enrolled. Two analogous areas of alopecia were identified. Both were injected with 1% lidocaine with epinephrine, tattooed and photographed. The first was biopsied using a 4 mm punch tool and used as the pre-treatment sample. The second was treated with a single pass of the Lutronic $eCO_2$ laser (120 hand piece; 30 W; 240 mJ; 100 density, 12×12 mm, Static mode). After 1 week, the subject returned for a repeat photography and biopsy as above. The samples were processed for mass spectrometry as described below. Histology is from before and 30 days after laser treatment.

Adult keratinocytes isolation and cultures. For human keratinocytes, 3-mm skin biopsies were taken from areas of the occipital scalp through above IRB protocols using enzyme digestion method as described in the literature[30,31]. For mouse keratinocytes, tails of adult mice were used and followed by the same protocol of human keratinocytes. Briefly, the skin fragments were incubated in 0.4% dispase II solution overnight at 4° C., allowing separation of epidermis from dermis. Then epidermis was incubated with 0.25% trypsin-EDTA (Lonza, Walkersville, MD) to isolate keratinocytes for 5 min at 37° C. Adult keratinocytes were maintained in KGM including defined growth factors (KGM-GOLD Bullet kit, #192060) (Lonza) and supplemented with 10 μM of ROCK inhibitor (Y-27632) (Cayman Chemical, #10005583) until use[32]. For all in vitro experiments, primary keratinocytes were passaged at least once to eliminate contaminating other cells isolated from epidermis and used at passage 2-4 for human and passage 1-2 for mouse keratinocytes.

Mouse strains. All mouse experiments were approved by JHU IACUC (MO17M298). Mouse strain, genotype and treatment regiments can be found in Table 3. C57BL/6NJ (JAX stock #005304) and C57BL/6J (JAX stock #00664) were used as the wild type strains for all in vivo experiments. Tlr3 (B6N.129S1-Tlr3$^{tm1Flv}$/J; stock #009675), Mda5 null (B6.Cg-Ifih1$^{tm1.1Cln}$/J; stock #015812), and Rarα null mice (Rarα$^{tm1Rev}$/HsvJ; stock #023845) were obtained from the Jackson Laboratory. RIG-I null and wild type mice in 129Sv/C57BL/6 background were provided by the Adolfo Garcia-Sastre laboratory (New York, NY). Krt5-CreERT2, Rarα-flox and Rarγ-flox mice were kindly provided by Pierre Chambon and Krt5-CreERT2 mice were crossed with mice including Cre-dependent floxed Rarα$^{fl/fl}$ and Rarγ$^{fl/fl}$. DNA was extracted from tail tips of all Cre-LoxP transgenic mice and genotyped by PCR using the Red-Xtract Kit (Millipore Sigma, XNAT-100) and appropriate primer sets (Table 1). For Cre-ERT2 transgenic mice, tamoxifen (Millipore Sigma, T5648) was dissolved in corn oil at 10 mg per ml and 75 mg of tamoxifen per kg of body weight was injected intraperitoneal (i.p.) every day for 9 days from day 15-24[33]. Mice were maintained by animal facilities at Hopkins and all experiments were performed by animal protocols (#MO17M298) approved by the Johns Hopkins University Animal Care and use Committee.

Wound Induced Hair Neogenesis (WIHN). All experiments were followed with the present inventors' WIHN protocol[1,9]. Briefly, hair was shaved and a 1.2 $cm^2$ full-thickness skin on the backs of 21-day old (telogen) male and female mice was removed by sterile scissors. A single treatment of RA (30 μl) (0.1 μg per mouse) (Millipore Sigma, R2625) and BMS493 (30 μl) (0.1 μg per mouse) (Cayman Chemical, #17418) was applied topically onto open wound on WD1 of Tlr3$^{-/-}$ and WT mice, respectively. Poly (I:C) (50 μl) (5 μg per mouse) (Invivogen, tlrl-pic) was injected under the healed scab on WD3 of WT mice as described before[9,34]. On WD20-24, numbers of regenerated hair follicles were visualized and quantified in the re-epithelialized skin by non-invasive confocal scanning laser microscopy (CSLM) (Caliber I.D., VIVASCOPE 1500) as published[1,9]. As a vehicle (Control), ethanol (EtOH), dimethylsulfoxide (DMSO), or PBS was treated for RA, BMS493, and Poly (I:C), respectively.

Microarray analysis. RNA isolated from keratinocytes with or without Poly (I:C) (GSE92646) and mouse wound tissues from wild type (C57BL/6NJ) and Tlr3$^{-/-}$ with BMS493 and RA were submitted to the JHMI Deep Sequencing & Microarray core for Affymetrix® Human Exon 1.0ST and mouse microarray chip according to manufacturer's protocols. Raw gene expression signals in the form of Affymetrix CEL files were extracted and normalized with Partek® Genomics Suite™ software using the Robust Multichip Analysis (RMA) algorithm. Genes were ranked according to fold change of the intervention, and referred to as top or bottom induced if they are at the highest fold change (top) or lowest fold change (bottom). The significance of gene expression was measured by student's t-test analysis. These datasets generated during the current study are available in the NCBI GEO repository as listed above.

Small interference RNA (siRNA) transfection. Human ALDH1A2 (Santa Cruz Biotechnology, sc41443), ALDH1A3 (Santa Cruz Biotechnology, sc43611), TLR3 (Dharmacon, M-007745-00), TRIF (Santa Cruz Biotechnology, sc106845), IRF3 (Santa Cruz Biotechnology, sc35710), NF-κB (Santa Cruz Biotechnology, sc29410) and non-targeting control (scramble) siRNAs (Santa Cruz Biotechnology, sc37007 & Dharmacon, D-001210) were commercially provided. Human scalp keratinocytes ($3×10^5$ cells per well) in 12-well plates were transfected with 20 nM of siRNAs using Lipofectamine® RNAiMAX (Thermo Fisher Scientific, #13778150) following the manufacturer's directions. Poly (I:C) (0.1 μg per ml) was applied to transfected cells and incubated for 48 hrs. At the end of transfection period, cells were harvested to isolate protein to perform qRT-PCR, western blot, and RA mass spectrometry.

BMS493 treatment. BMS493 pan-RARs antagonist (1 μM) was pre-treated into keratinocytes for an hour and cells were incubated with RA (0.1 μM and 0.5 μM for human and mouse keratinocytes, respectively) or Poly (I:C) (0.1 μg per ml for both human and mouse keratinocytes) for 48 hrs. At the end of the experiment, cells were harvested for RNA and protein extraction to do further analysis including qRT-PCR and western blot.

IL6 treatment. Recombinant human interleukin 6 (rhIL6) (R&D system; 206-IL-010) was treated into human scalp keratinocytes with dose-dependent manners (0, 10, 50, and 100 ng per ml) for 2 days. Cells were harvested and lysates were used for RA measurement.

Tissue preparation from wounded mice. Wild type (C57BL/6J and 6NJ) and Tlr3$^{-/-}$ mice were wounded as did in WIHN experiments. On PWD11 when wounds are closed, the center and edge of the wound was separated by scissors. Skin samples were immediately frozen and saved in liquid nitrogen for further analysis.

Proteomic analysis. For in vivo samples, wild-type and Tlr3$^{-/-}$ unwounded and wounded skin where wound regions (center and edge area) were prepared for analysis. For in vitro samples, human primary scalp keratinocytes treated with 0.1 μM retinoic acid (RA) or 0.5 μg per ml Poly (I:C) and control were used. In vivo and in vitro samples were lysed in 5% sodium deoxycholate after washing in phosphate-buffered saline. Lysates were washed, reduced, alkylated and trypsinolyzed on filter as described by Wisniewski et al.[35] and Erde et al.[36]. Tryptic peptides were separated on a nanoACQUITY UPLC analytical column (BEH130 $C_{18}$, 1.7 μm, 75 μm×200 mm, Waters) over a 165 min linear acetonitrile gradient (3-40%) with 0.1% formic acid on a Waters nano-ACQUITY UPLC system, and analyzed on a coupled Thermo Scientific Orbitrap Fusion Tribrid mass spectrometer as described by Williamson et al.[37]. Full scans were acquired at a resolution of 120,000, and precursors were selected for fragmentation by higher-energy collisional dissociation (normalized collision energy at 30%) for a maximum 3-second cycle. Tandem mass spectra were searched against a UniProt human reference proteome using MS Amanda algorithm described by Dorfer et al.[38] with a maximum precursor mass error tolerance of 10 ppm. Carbamidomethylation of cysteine and deamidation of asparagine and glutamine were treated as static and dynamic modifications, respectively. Resulting hits were validated at a maximum false discovery rate of 0.01 using a semi-supervised machine learning algorithm Percolator developed by Käll et al.[39]. Protein abundance ratios were measured by comparing the MS1 peak volumes of peptide ions, whose identities were confirmed by MS2 sequencing as described above. The Label-free quantifications were performed using an aligned AMRT (Accurate Mass and Retention Time) cluster quantification algorithm Minora (Thermo Fisher Scientific, 2017). Pathway and gene ontology analysis were performed with Qiagen Ingenuity, Panther GO and DAVID databases, as described by Kramer et al.[40], Mi et al.[41], and Huang et al.[42], respectively.

Determination of Retinoid Levels. For in vitro samples, human scalp keratinocytes were incubated with 0.5 μg per ml of Poly (I:C) for 48 hrs or siRNAs-transfected cells were incubated with 0.1 μg per ml of Poly (I:C) for 48 hrs. For in vivo samples, skin was analyzed from wild-type and Tlr3$^{-/-}$ unwounded and wounded skin where wound regions (center and edge area) were cut by scalpel. Human skin was analyzed for retinoids with and without $CO_2$ laser treatment as described. All samples were frozen at collection and stored at −80° C. until extraction. For in vitro experiments, media and cell pellets were analyzed separately. For in vivo experiments, tissues were homogenized in saline. Extraction of retinoids was performed under yellow lights using a two-step liquid-liquid extraction that has been described in detail previously using 4,4-dimethyl-RA as an internal standard for RA and retinyl acetate as an internal standard for retinol and total retinyl ester[43-46]. For the extraction of retinoids, 1 to 3 ml of 0.025 M KOH in ethanol was added to tissue homogenates (in vivo) or cell culture (in vitro) samples. Then 10 ml hexane (for in vivo tissue sample) or 5 ml hexane (for in vitro cell culture sample) was added to the aqueous ethanol phase. The samples were vortexed and centrifuged for 1 to 3 min at 1000 rpm in a Dynac centrifuge (Becton Dickinson) to facilitate phase separation and pellet precipitated protein. The hexane (top) phase containing nonpolar retinoids (ROL and RE) was removed. 4 M HCl (60-180 μl) was added to the remaining aqueous ethanol phase, samples were vortexed, and then polar retinoids (RA) were removed by extraction with a second 5-10 ml aliquot of hexane as described above. Organic hexane phases were evaporated under nitrogen while heating at approximately 25 to 30° C. in a water bath (model N-EVAP 112, Organomation Associates, Berlin, MA, USA). All samples were resuspended in 60 μl acetonitrile. Only glass containers, pipettes, and syringes were used to handle retinoids.

Levels of RA were determined by liquid chromatography-multistage tandem mass spectrometry (LC-MRM$^3$) which is an LC-MS/MS method utilizing two distinct fragmentation events for enhanced selectivity[43]. RA was measured using a Shimadzu Prominence UFLC XR liquid chromatography system (Shimadzu, Columbia, MD) coupled to an AB Sciex 5500 or 6500+ QTRAP hybrid triple quadrupole mass spectrometer (AB Sciex, Framingham, MA) using atmospheric pressure chemical ionization (APCI) operated in positive ion mode as previously described[43]. For the LC separation, the column temperature was controlled at 25° C., the auto-sampler was maintained at 4° C., and the injection volume was typically 10 to 20 μl. All separations were performed using an Ascentis Express RP-Amide guard cartridge column (Supelco, 50×2.1 mm, 2.7 μm) coupled to an Ascentis Express RP-Amide analytical column (Supelco, 100×2.1 mm, 2.7 μm). Mobile phase A consisted of 0.1% formic acid in water, and mobile phase B consisted of 0.1% formic acid in acetonitrile. Endogenously occurring retinoid isomers including all-trans-retinoic acid (RA), 9-cis retinoic acid, 13-cis retinoic acid, and 9,13-di-cis retinoic acid are resolved using a gradient separation at a flow rate of 0.4 mL/min with the following gradient: 0-1 min, 60% B; 1-7 min, ramp to 95% B; 7-9 min, hold at 95% B; 9-9.5 min, ramp to 10% B; 9.5-10.5 min, hold at 10% B; 10.5-11 min, ramp to 95% B; 11-12.5 min, hold at 95% B; 12.5-13 min, ramp to 60% B; 13-15 min, re-equilibrate at 60% B. The APCI source conditions and MRM$^3$ detection parameters were as follows: curtain gas, 15; collision gas, low; nebulizer current, 3; temperature, 325; ion source gas, 55; declustering potential, 56; entrance potential, 12; collision energy, 17; excitation energy, 0.1; excitation time, 25; ion trap fill time, 125. The MRM$^3$ transition for RA was m/z 301.1→m/z 205.1→m/z 159.1 and for 4,4-dimethyl RA was m/z 329.2→m/z 151.2→m/z 100.0.

Retinol and RE were quantified via HPLC-UV according to previously published methodology[46,47]. Retinol and RE were resolved by reverse-phase chromatography (Zorbax SB-C18, 4.6×100 mm, 3.5 μm) on a Waters Acquity UPLC H-class system and were quantified by UV absorbance at 325 nm. Analytes were separated at 1 ml per min with 11% water/89% acetonitrile/0.1% formic acid for 9 min, followed by a linear gradient over 2 min to 100% acetonitrile. Then 100% acetonitrile was maintained for 2 min, followed by a linear gradient over 2 min to 5% acetonitrile/1,2-dichloroethane. Final conditions were held for 2 min before returning to initial conditions. Injection volume was 30 μl for all samples. Retinol eluted at 4.0 min, retinyl acetate (internal standard) eluted at 7.9 min, and RE eluted at 16.5 min.

The amount of RA, ROL and total RE was normalized per million cells for cellular assays and per g tissue for skin analyses.

RNA isolation and quantitative real-time PCR (qRT-PCR). For cells, total RNA was isolated from cultured keratinocytes using RNeasy Mini Kit (Qiagen, Valencia, CA, #74106) and treated with DNase I (Qiagen, #79254) to eliminate genomic DNA. For tissue, total RNA was isolated by following the manual of Direct-zol™ RNA MiniPrep Plus kit (Zymo Research, R2073). The purity and concentration of RNAs were analyzed using a NanoDrop2000c (Thermo Fisher Scientific, ND-2000c). Following reverse transcriptase reactions using high-capacity RNA to cDNA kit (Life Technologies), qRT-PCR was performed to measure target genes using TaqMan probes and Fast reaction master mix reagents (Life Technologies). Relative expression of mRNAs was analyzed by the cycle of threshold (Ct) value of target genes and quantified by normalizing to ribosomal protein large P0 (RPLP0) for human keratinocytes and to β-Actin for mouse keratinocytes or tissues as housekeeping genes using the $\Delta\Delta C_t$ method[48].

Western blot analysis. Human and mouse keratinocytes were disrupted in M-PER lysis buffer (Thermo Fisher Scientific, #78501) containing protease inhibitors (Thermo Fisher Scientific, #87786) using ultrasonic homogenizer (20% power with 5 times every 2 seconds) to extract proteins. Then, protein concentrations were determined by BCA method (Thermo Fisher Scientific, #23225). Western blot procedures were followed by the protocol of NuPAGE system (Thermo Fisher Scientific). Briefly, 20 μg of protein samples were loaded for electrophoresis and transferred to polyvinylidene di-fluoride (PVDF) membrane (Bio-Rad, Hercules, CA). After blocking for at least an hour in 5% non-fat dry milk, the membrane was incubated with primary antibodies with appropriate dilutions (Table 2) at 4° C. overnight and followed by incubation with secondary antibodies for 1 hour at room temperature. Protein amounts were normalized to rabbit polyclonal anti-human β-actin antibody (1:1,000 dilution) (Cell Signaling Technology). Finally, proteins were visualized using SuperSignal West Pico PLUS chemiluminescent substrate kit (Thermo Fisher Scientific, #34577) and saved as image files using ChemiDoc XRS+ (Bio-Rad). The signal intensity of protein was quantified using Image Lab software (Bio-Rad). Original images of representative blots were provided in the Source data file.

Immunofluorescence. For tissues, frozen-sections of mouse skin samples were stained with primary antibodies with appropriate dilution at 4° C. overnight, followed by incubation with goat anti-rabbit IgG labeled with Alexa Flour® 488 (Life Technologies) and 594 (Life Technologies) for 1 hour at room temperature. For cells, keratinocytes ($3\times10^5$ cells) plated on cover-slip were fixed with 4% Paraformaldehyde (PFA) for 10 min, permeabilized in PBS including 0.5% Triton X-100 for 15 min at room temperature. After washing with PBS 3 times, cells were stained with primary antibodies overnight at 4° C., followed by incubation with goat anti-rabbit or mouse IgG labeled with Alexa Flour® 488 for 1 hour at room temperature. Cell nuclei were visualized by mounting medium including DAPI (Vector Laboratories, Burlingame, CA, H-1200). Fluorescence images were observed by fluorescence microscopy (Leica microsystems), taken pictures with ×100 (low magnification) and ×200 (high magnification), and saved as image files.

Statistics. All data were created by at least three individual experiments to achieve statistical significances. For two groups, results were analyzed by student t-test (unpaired or paired) to evaluate substantial differences using Microsoft Excel program. For more than three groups, the means of results were analyzed by one-way ANOVA using GraphPad Prism8 software. Data are represented as mean±s.e.m. Statistical significance was obtained at P-value less than 0.05.

Data availability. All data for microarray analyses are deposited in the Gene Expression Omnibus (GEO); GSE128868 [https://www.ncbi.nlm.nih.gov/geo/query/acc.cgi?acc=GSE128868]. All proteomic datasets are available to download from the data repository of University of Maryland metallotherapeutics research center, Baltimore [https://bit.ly/2U9qwqO].

Results

Cellular responses to dsRNA or RA highly overlap. To identify pathways associated with human skin rejuvenation, the present inventors treated 17 subjects with a conventional laser treatment known to improve skin photoaging (FIG. 1A) and then biopsied the treated skin to determine gene expression changes one week after the first treatment. The present inventors noted parallel increases in signatures for the TLR3 ligand dsRNA and RA (FIG. 1A-1C), though other immune signatures were upregulated as well (IFNG, TNF, IRF7, IRFNA2). RA is a potent morphogen important in development, regulates stem cell function[16], and itself a therapy for photoaging, however the mechanism by which its endogenous synthesis is regulated not fully understood. Therefore, the present inventors hypothesized that dsRNA-mediated signaling induces RA synthesis to regulate regeneration thereby identifying an unexplored functional link between these two pathways in stem cell function and more broadly in their diverse physiologic roles.

Figure 1G:
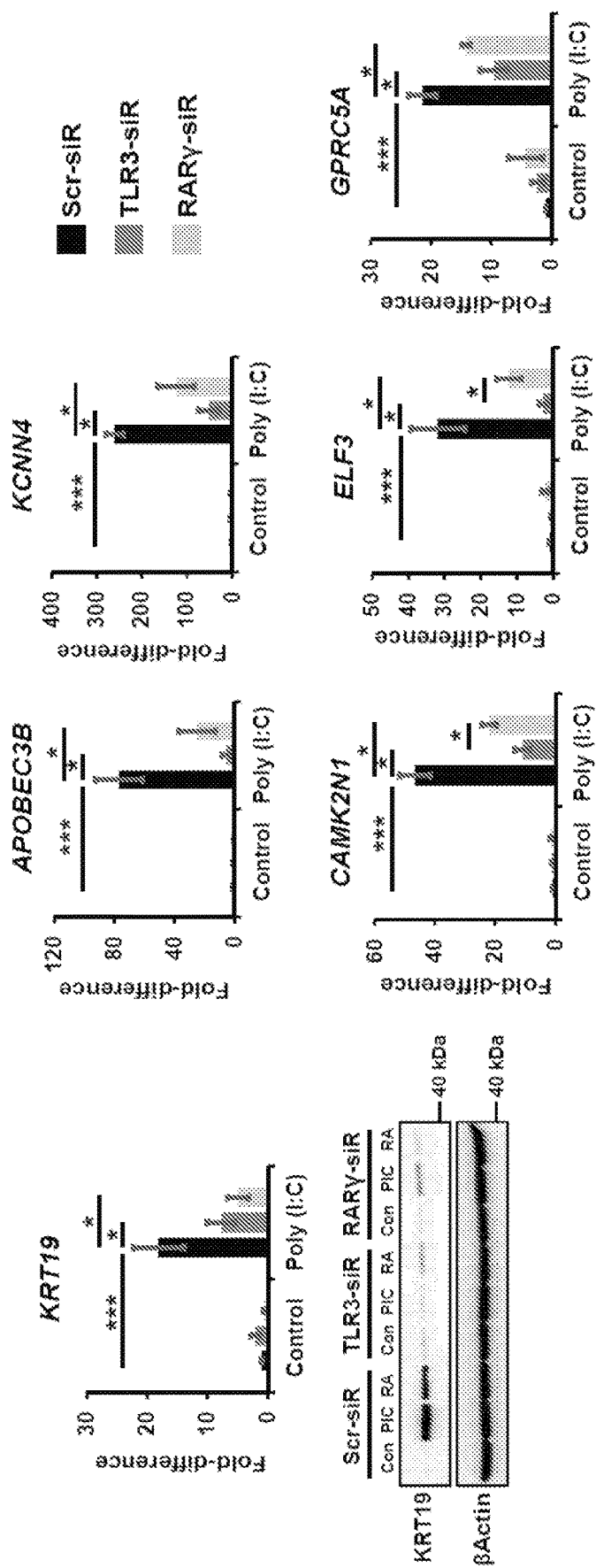
Figure 2A:
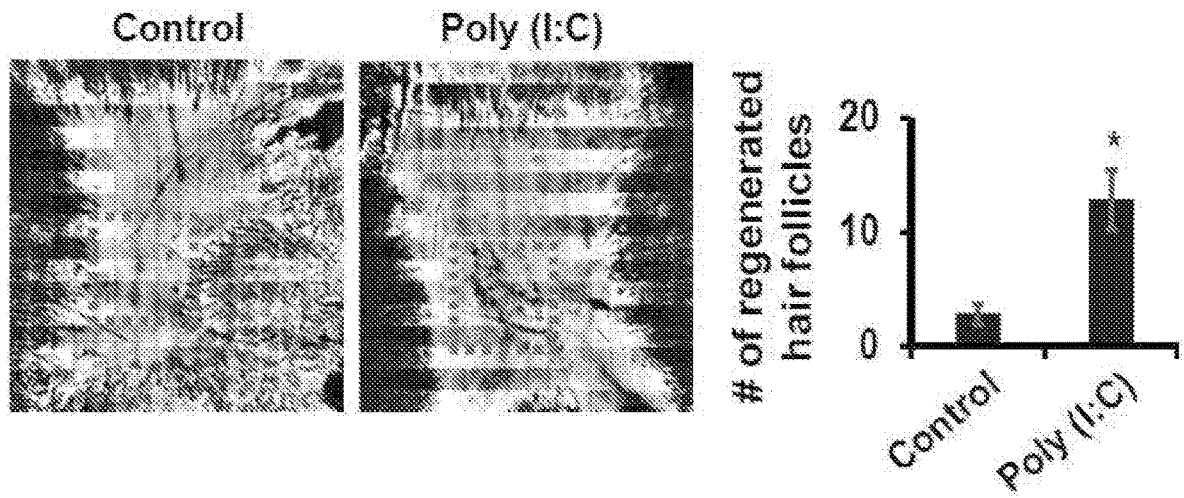
Figure 2B:
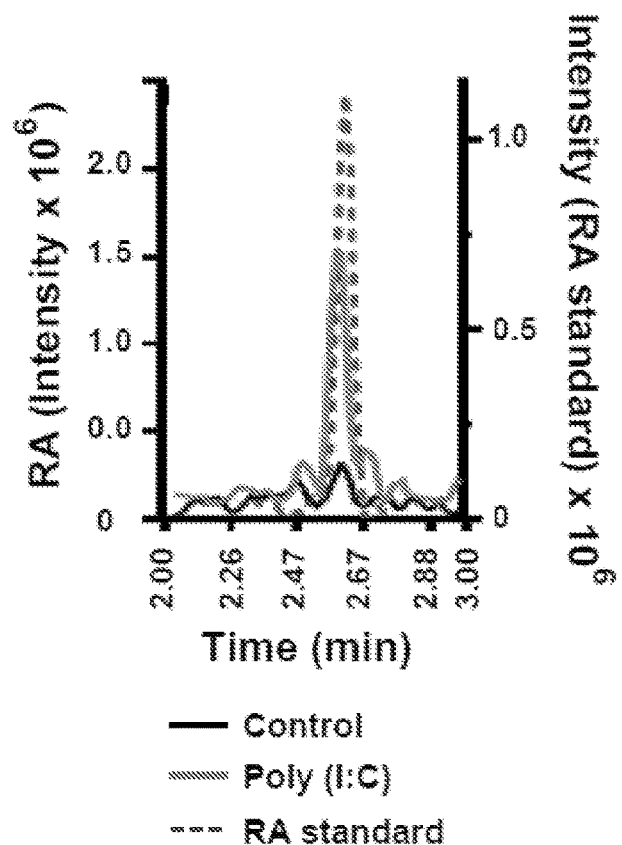
Figure 2C:
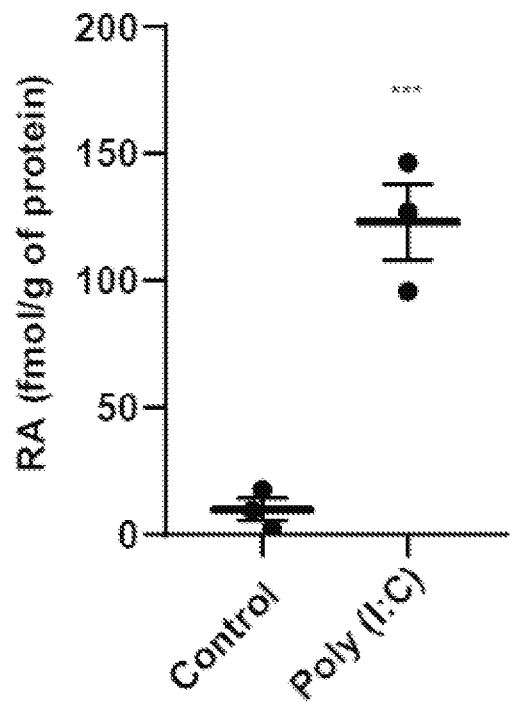
Figure 2D:
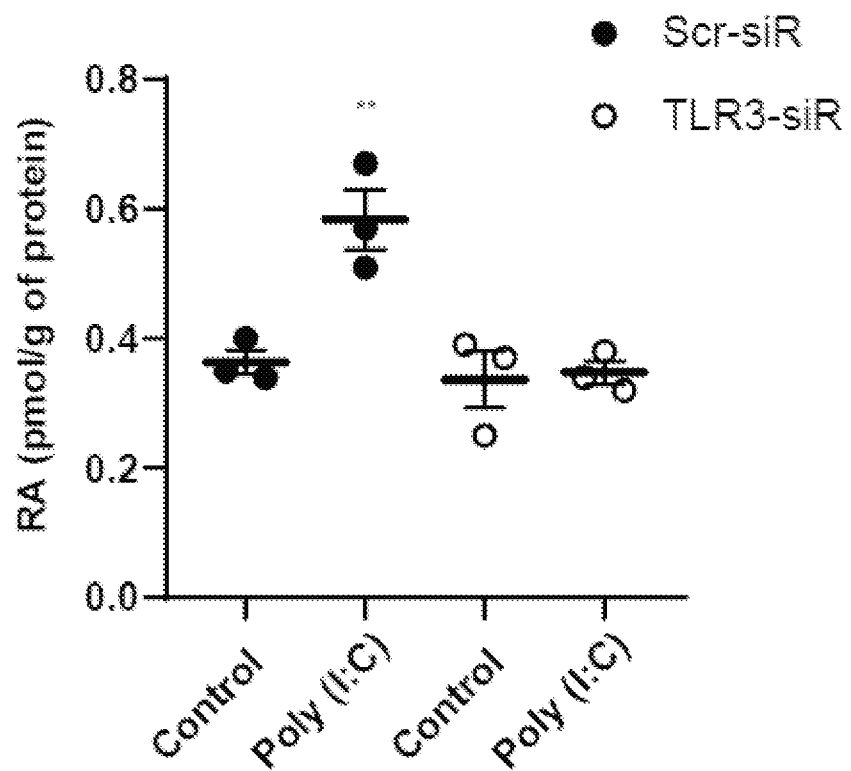
Figure 2E:
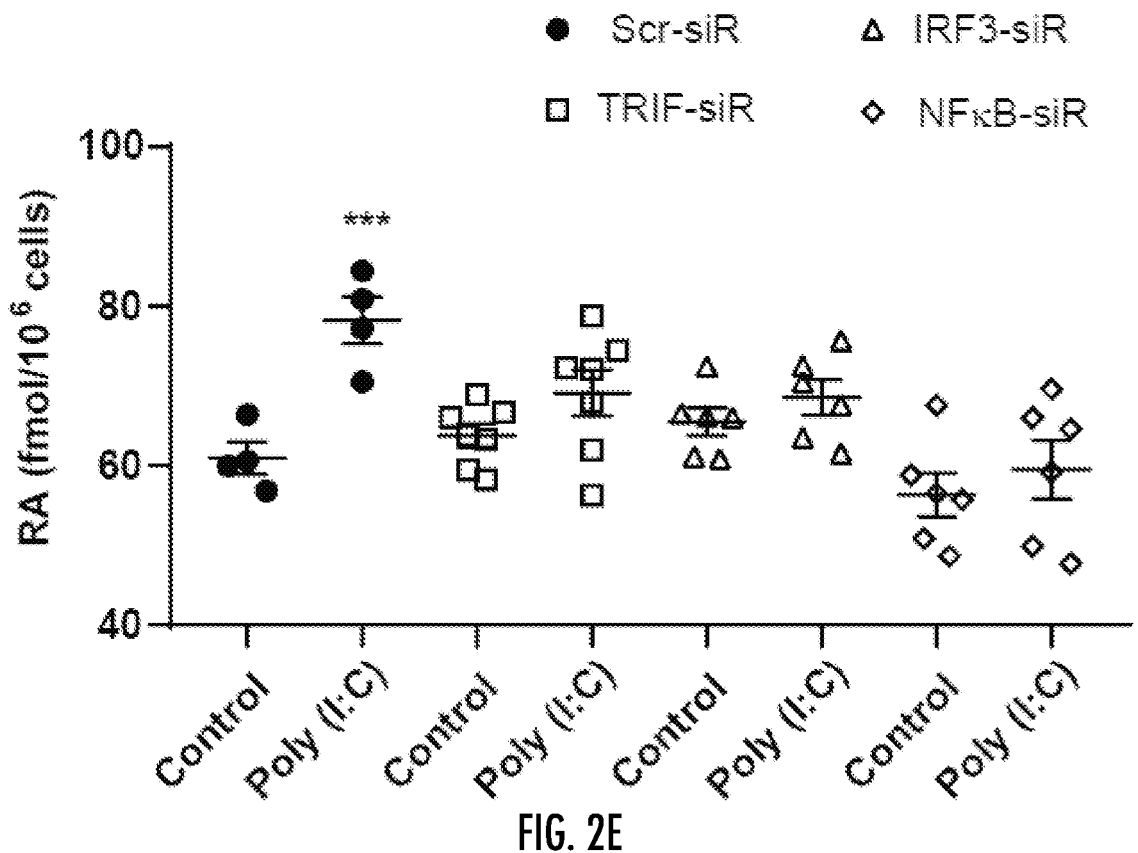
Figure 2F:
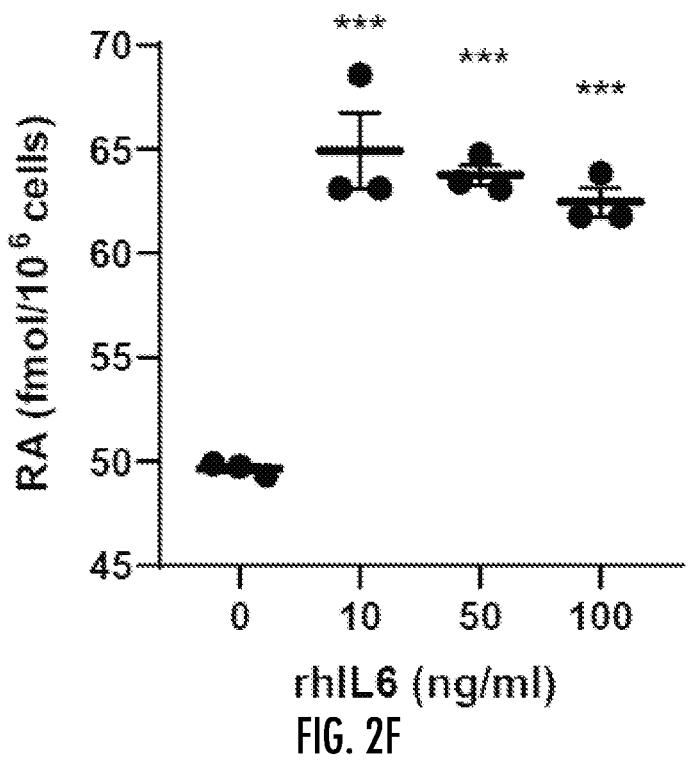
Figure 6A:
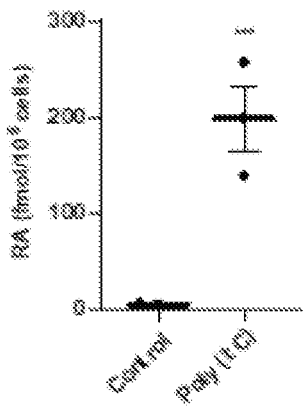
FIG. 6A-K. In vitro and in vivo analysis of vitamin A metabolites using LC-MS.
Figure 6B:
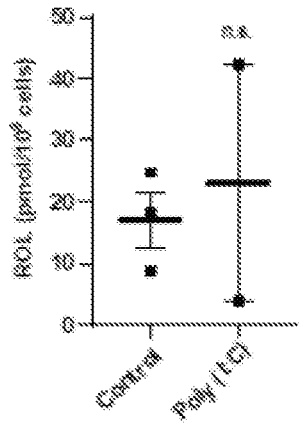
Figure 6B:
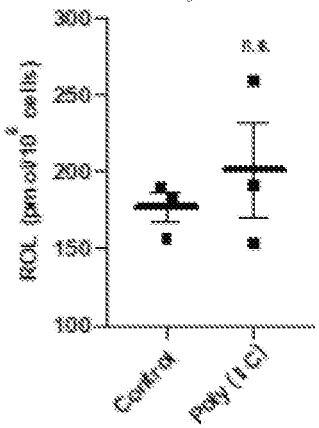
Figure 6C:
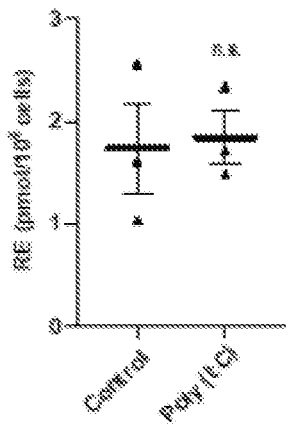
Figure 6C:
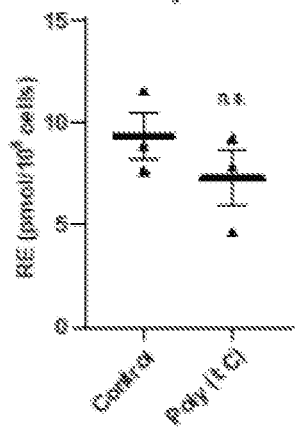
Figure 6D:
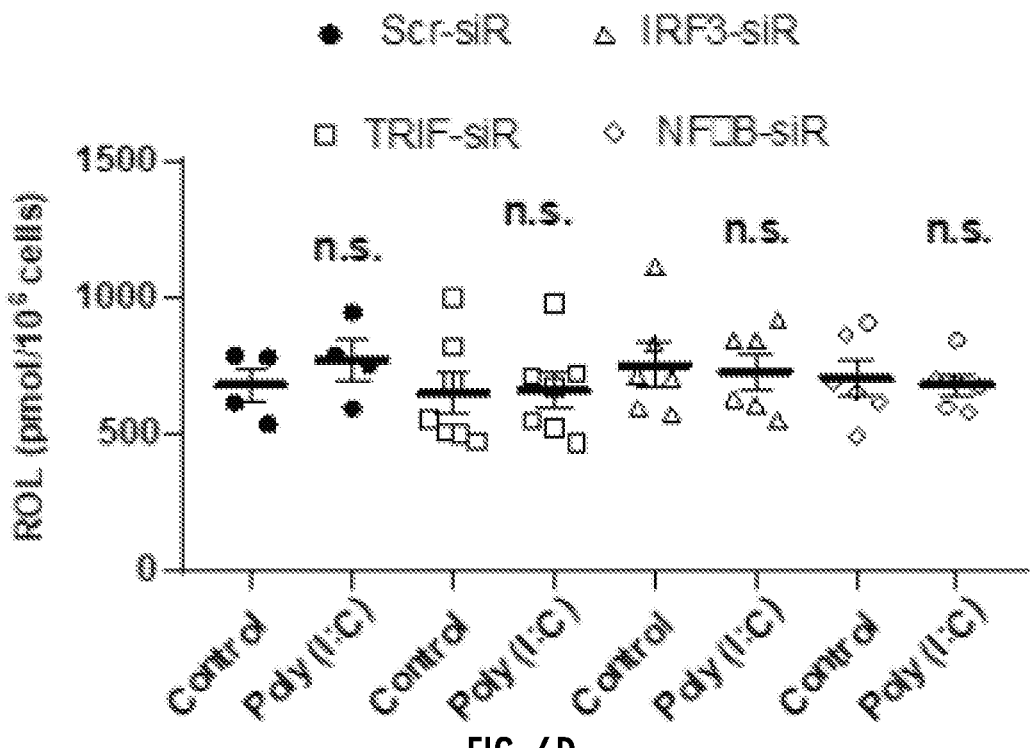
Figure 6E:
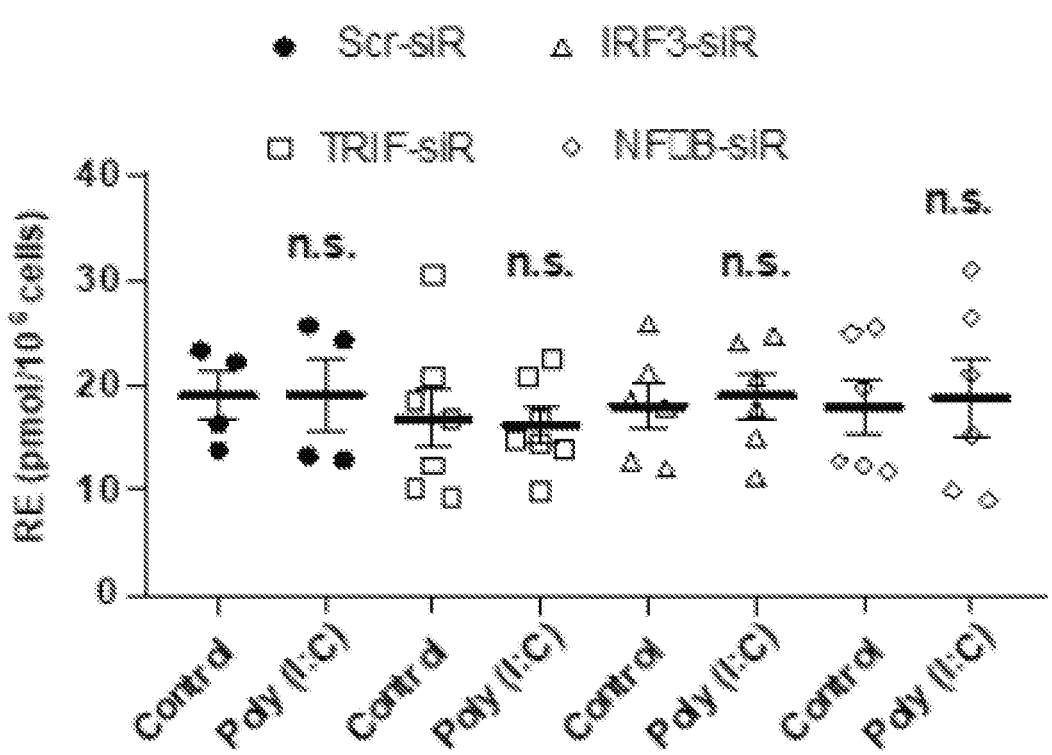
Figure 6F:
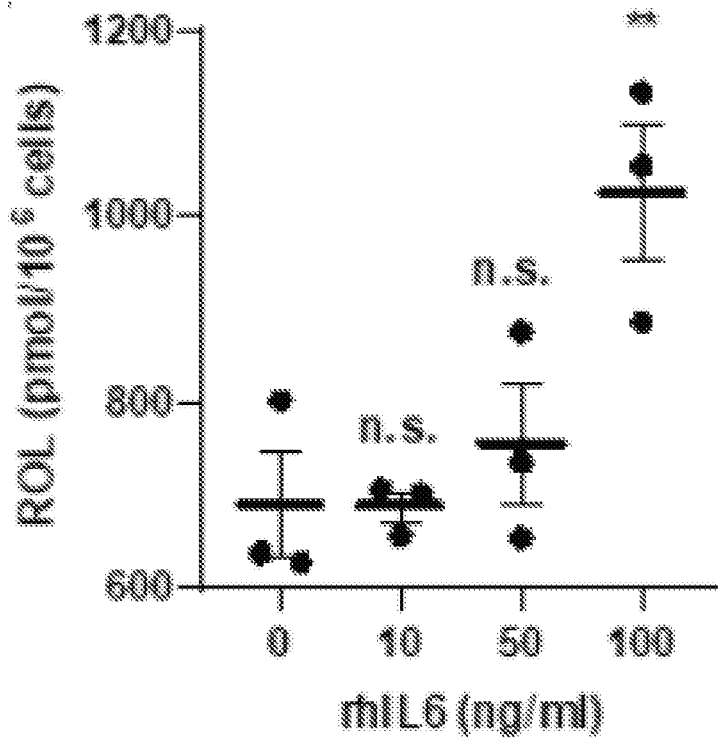
Figure 6G:
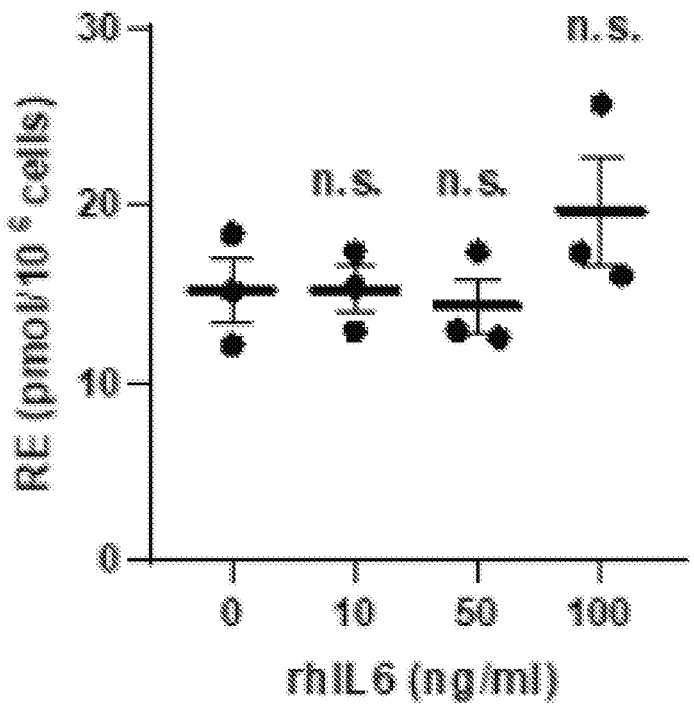
Figure 6K:
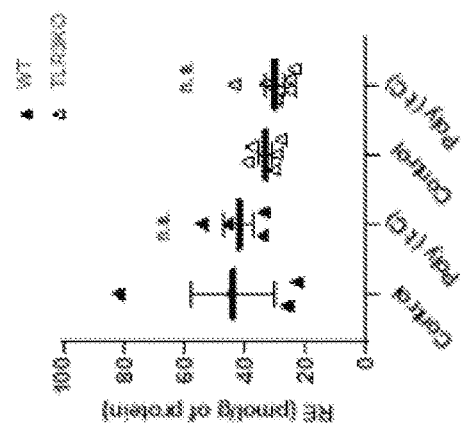
Figure 6J:
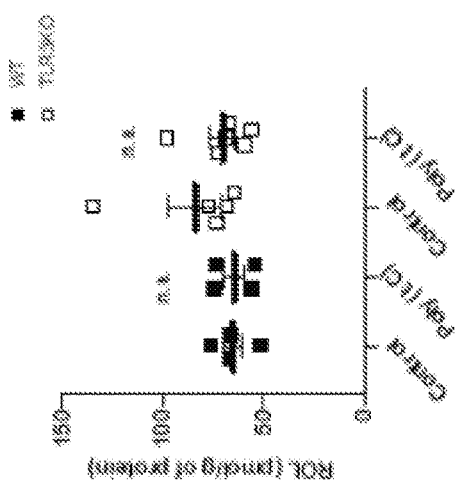
Figure 6I:
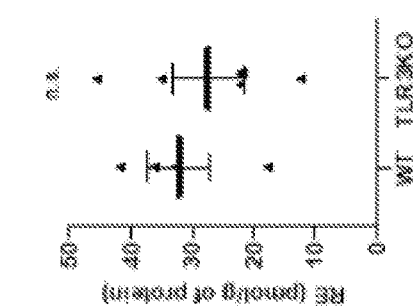
Figure 6H:
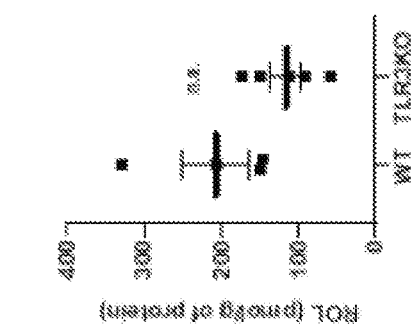
Figure 7A:
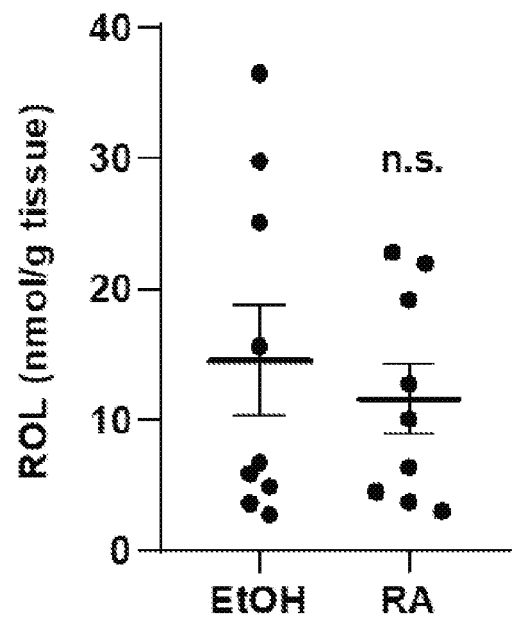
FIG. 7A-7B. In vivo analysis of vitamin A metabolites in Tlr3-/- mice with exogenous RA treatment using LC-MS. Analysis of ROL (FIG. 7A) and RE (FIG. 7B) in wounded skin of WT and Tlr3-/- mice with treatment of Ethanol (EtOH) and RA. (n=9 independent animals). n.s.; not significant. Data are means±SEM.
Figure 7B:
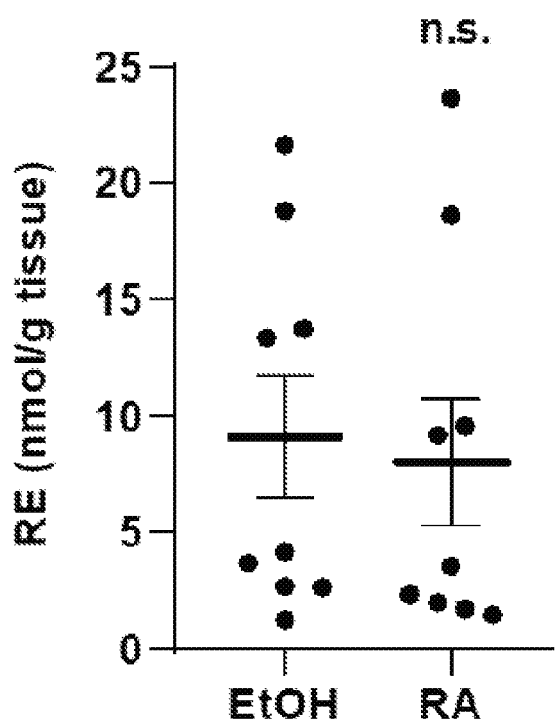

The present inventors first compared the transcriptomes and proteomes of normal human keratinocytes after treatment with dsRNA (Polyinosinic-polycytidylic acid; Poly (I:C)) or RA in vitro. The present inventors ranked the top 100 unregulated and downregulated transcripts (FIG. 1D) and proteins (FIG. 1E) according to their fold change after stimulation and defined the overlapping genes between these two different stimuli. Surprisingly, the present inventors found a dramatic overlap. For mRNA transcript expression, Poly (I:C) and RA induced and inhibited 13% and 18% identical gene transcripts respectively (FIG. 1E). The present inventors noted many of these gene transcripts were involved in keratinocyte differentiation; KERATIN19 (KRT19) is a marker of basal keratinocyte stem cells residing in the hair follicle bulge compartment. Conversely, KERATIN' (KRT1) is a marker of committed differentiated cells of the suprabasal layer and was inhibited by both stimuli. The overlap was even greater for protein expression, with an overlap of induced and inhibited 61% and 36% respectively (FIG. 1E). Among proteins, the present inventors found a similar pattern where genes like tumor protein p63 (TP63/p63) were induced; it is among the earliest transcription factors to define an epidermal fate during development. Similarly, FILAGGRIN (FLG)—a marker of highly differentiated keratinocytes—was inhibited by both stimuli. Unsupervised gene ontology analyses confirmed these findings and demonstrated a substantial enrichment of gene transcripts involved in epidermal development in both induced and inhibited transcripts, with a particular inhibition of keratinocyte differentiation by both stimuli (FIG. 1F). Finally, to begin to test for a functional link between TLR3 and RA signaling, the present inventors investigated if transcripts induced by Poly (I:C) require not only its receptor TLR3, but also the RA receptor gamma (RARγ) for induction. The present inventors verified this is the case for six transcripts including KRT19 (FIG. 1G). These findings suggest that dsRNA and RA stimulate highly overlapping cellular responses.

dsRNA and TLR3 signaling induces RA accumulation. Given the overlapping transcripts and proteins regulated by both Poly (I:C) and RA, and the ability for Poly (I:C) to induce WIHN (FIG. 2A), the present inventors hypothesized that dsRNA might induce RA synthesis to explain the shared response. To test this, the present inventors treated human keratinocytes with Poly (I:C) and collected cell lysates and culture media to measure RA levels. Poly (I:C) markedly increased RA abundance (FIG. 2B-2C). To determine the impact of Poly (I:C) on retinoid homeostasis, the present inventors also measured retinol (ROL; the substrate for the first step of RA biosynthesis) and retinyl ester (RE; the storage form of vitamin A) but their quantities were not modified as it was for RA (FIG. 6B-6C). In the case of RA, Poly (I:C)-induced accumulation is dependent on TLR3 (FIG. 2D), analogously to the requirement for TLR3 in WIHN in vivo (FIG. 2G). Consistent with this finding, the present inventors also found that TLR3 downstream factors including TIR-domain-containing adapter-inducing interferon β (TRIF/TICAM1), interferon regulatory factor 3 (IRF3), and NF-kB were required and Interleukin 6 (IL-6) sufficient to substantially stimulate RA accumulation (FIG. 2E-2F). These results suggest that dsRNA through TLR3 signaling induces intrinsic RA synthesis at its most distal step to promote the conversion from retinal to RA. These observations raised the questions of whether this occurs in vivo.

To study the in vivo interplay between dsRNA and RA, the present inventors focused on WIHN given the quantitative ability to count de novo follicles in a defined wound size as an index of regeneration. TLR3 is an important dsRNA receptor in wounding and WIHN[9,17,18]. After wounding, Poly (I:C) stimulates new hair follicle formation (WIHN) (FIG. 2A), whereas Tlr3$^{-/-}$ mice show limited regeneration capacity compared to wild-type (WT) mice (FIG. 2G). Given that Poly (I:C) induces intrinsic RA synthesis, the present inventors speculated that Tlr3$^{-/-}$ mice might have lower RA abundance. The present inventors first measured endogenous RA levels using non-wounded normal skin. As expected, WT mice had more RA at baseline than Tlr3$^{-/-}$ mice (FIG. 2H), while other metabolites were not substantially different (FIG. 1H-1I). Moreover, the amount of RA, but not other metabolites (FIG. 1J-1K), was substantially increased during wound healing by Poly (I:C) treatment in WT mice, but much less so in Tlr3$^{-/-}$ mice (FIG. 2I). As seen in vitro, these findings demonstrate in both unwounded basal tissue and in response to exogenous dsRNA, TLR3 is required for RA synthesis in vivo.

Figure 3A:
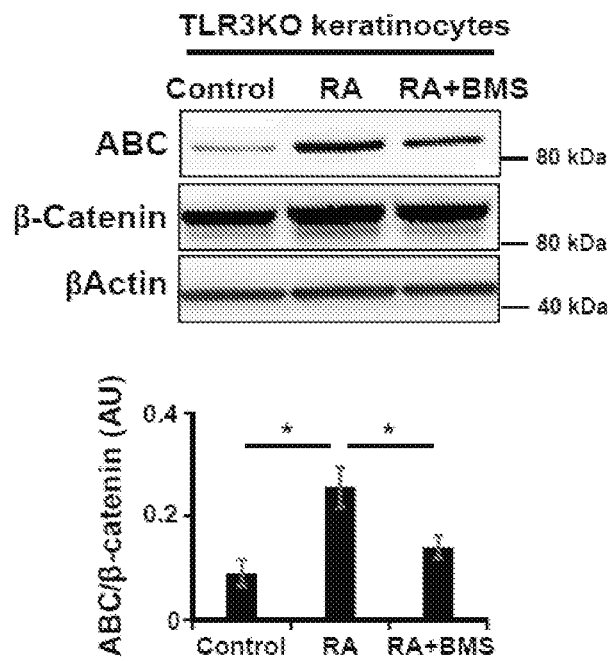
FIG. 3A-3F. RA induces keratinocyte stem cell markers and promotes WIHN in Tlr3$^{-/-}$ mice.
Figure 3B:
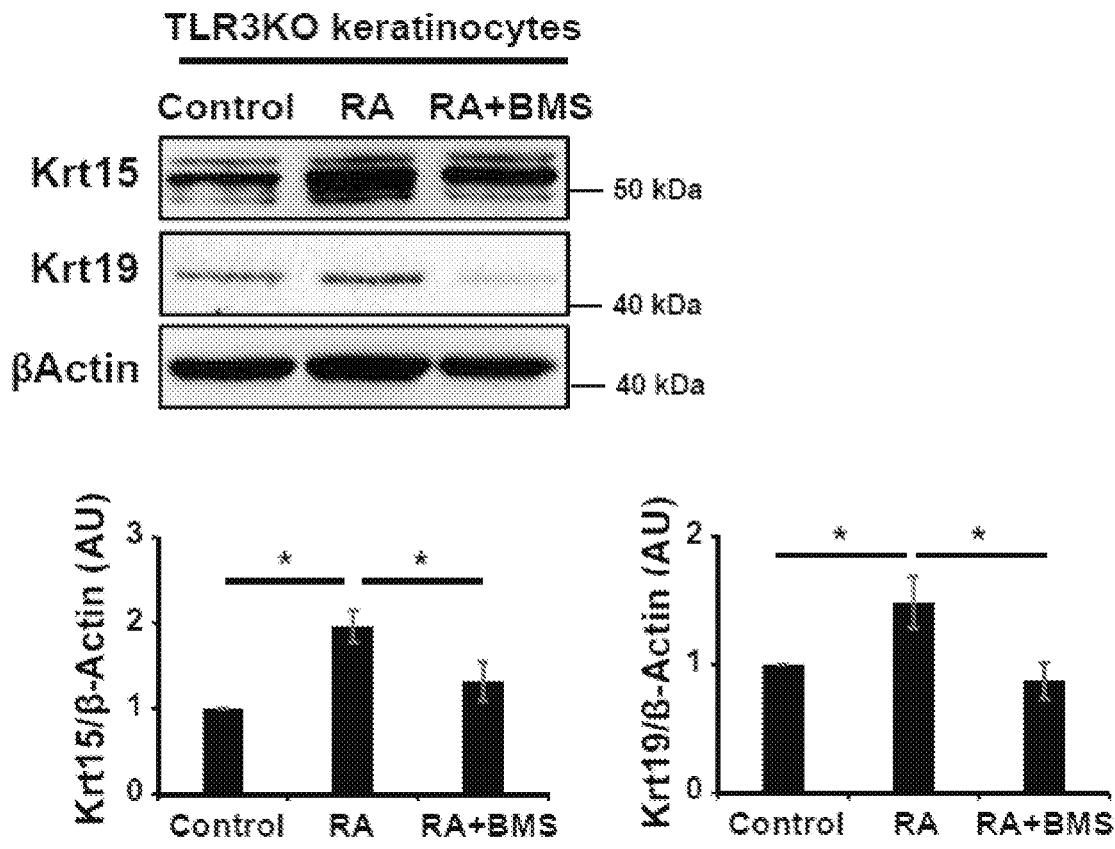
Figure 3C:
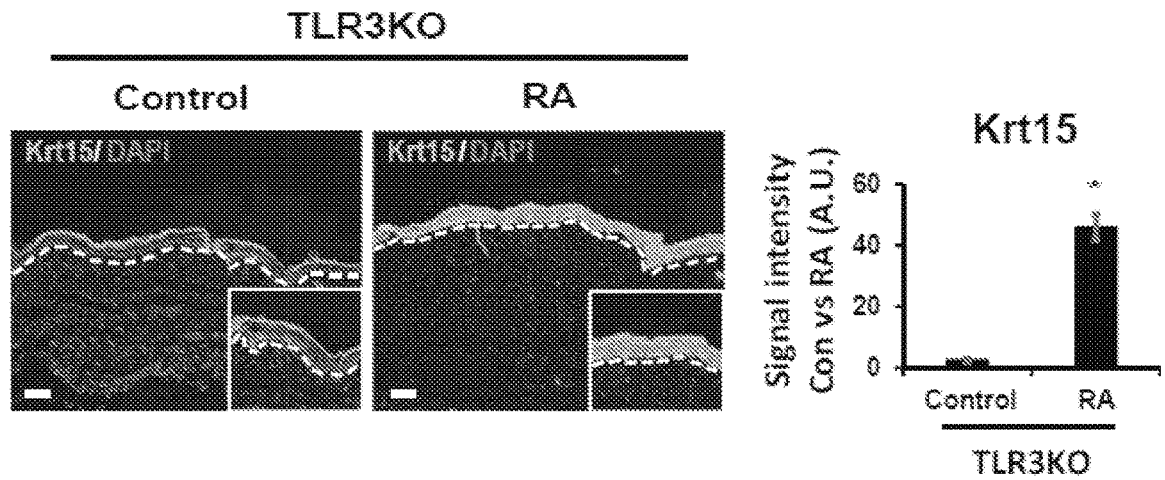
Figure 3D:
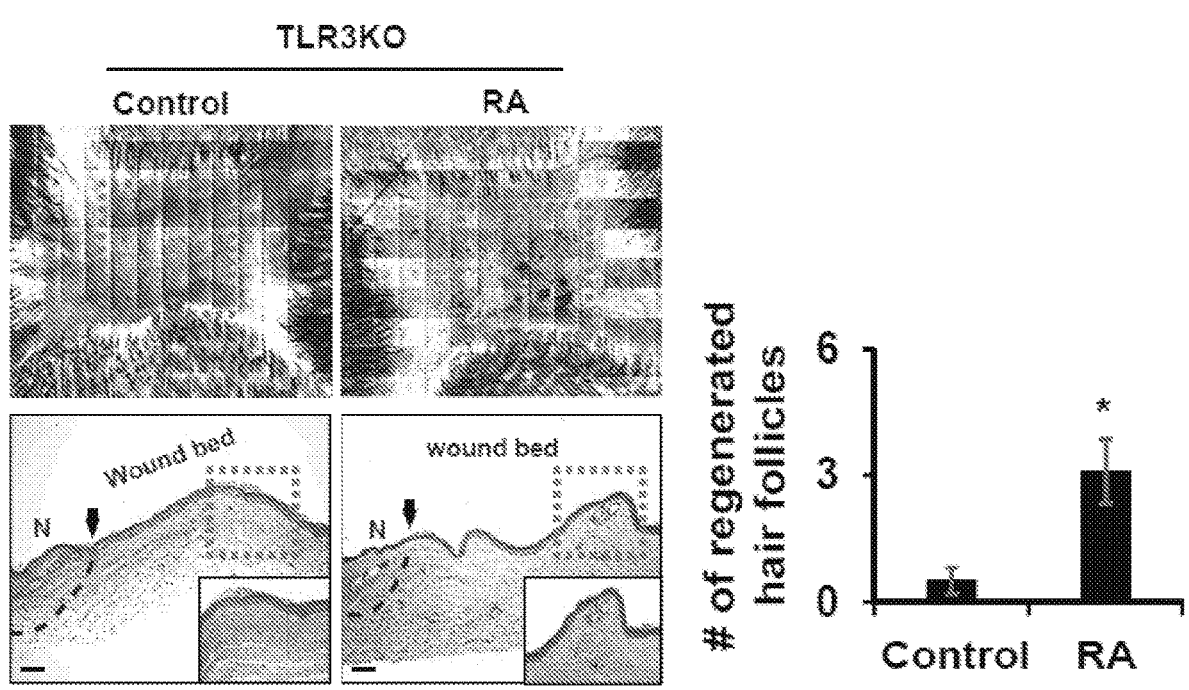
Figures 3E, 3F:
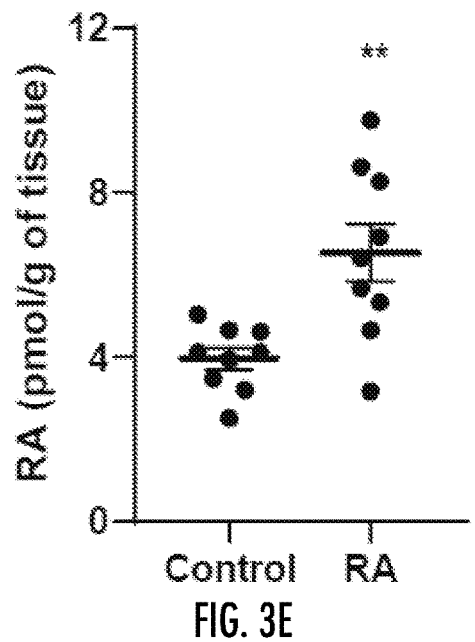

RA induces hair follicle regeneration in Tlr3 deleted mice. Given that Tlr3$^{-/-}$ mice have lower levels of endogenous RA and less WIHN compared to WT mice, the present inventors' next question was whether the impaired regeneration of Tlr3$^{-/-}$ mice could be improved with exogenous RA treatment. The present inventors first isolated keratinocytes or whole skin from Tlr3$^{-/-}$ mice and noted that RA increased the levels of Krt19, Krt15 and activated β-catenin protein, known to be necessary and sufficient for WIHN[1,19] (FIG. 3A-3C). Concomitantly, exogenous RA modestly increased hair follicle regeneration in Tlr3$^{-/-}$ mice (FIG. 3D), with measurable increases in tissue RA levels prior to morphogenesis (FIG. 3E). While the increase was significant (unpaired t-test), the background strain of these mice prohibits high levels of WIHN[9], and known induction of RA degradation pathways by RA might explain the modest increase. However, in microarray analysis of Tlr3$^{-/-}$ mice treated with RA, the present inventors identified a substantial enrichment of gene ontology categories pertaining to development and morphogenesis (FIG. 3F), as seen during regeneration[9]. Collectively, these results demonstrate that dsRNA and TLR3 are responsible in vivo for RA production and hair follicle regeneration.

Figure 4A:
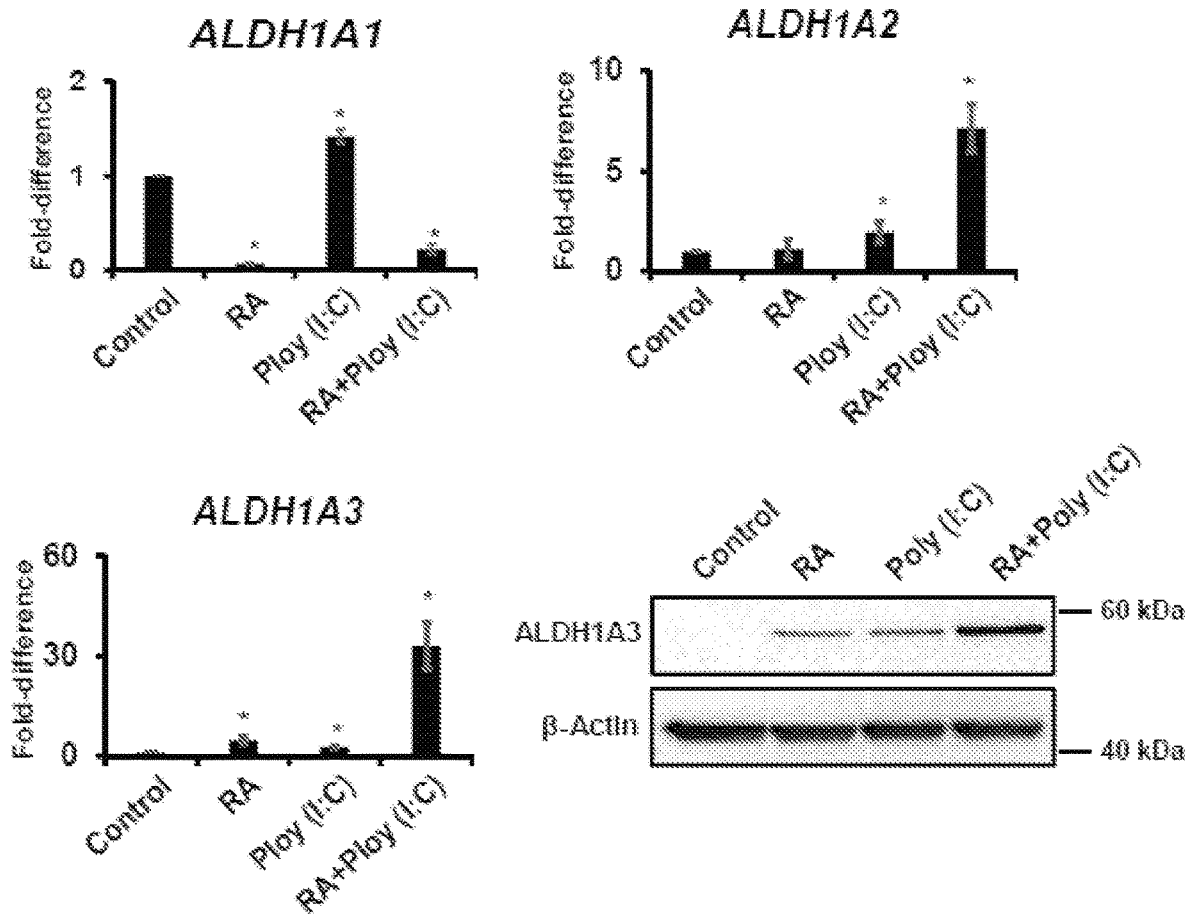
FIG. 4A-4I. dsRNA induces ALDH1A2/A3 for RA synthesis and accumulation.
Figure 4B:
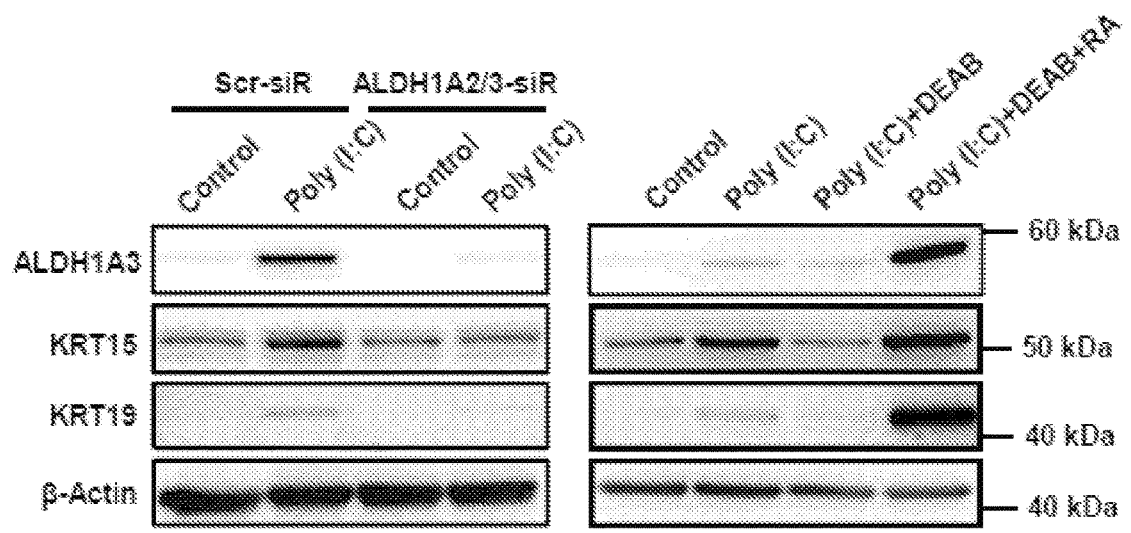
Figure 4C:
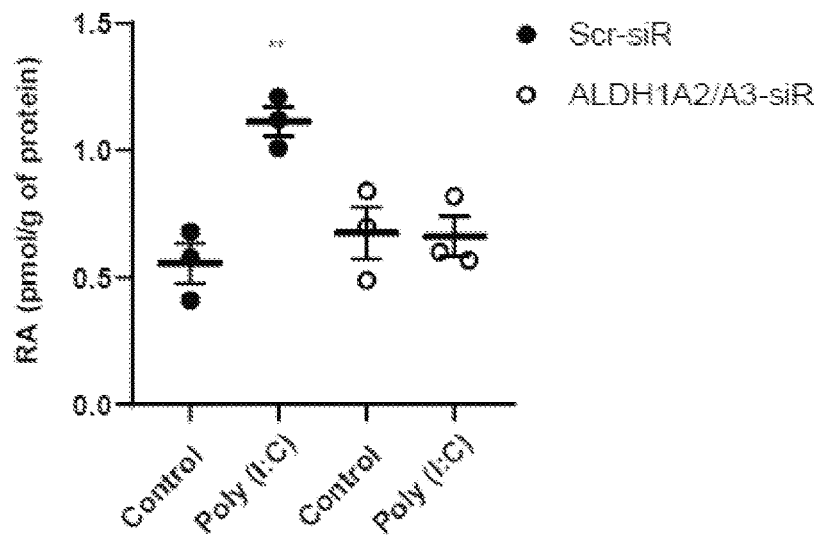
Figure 4D:
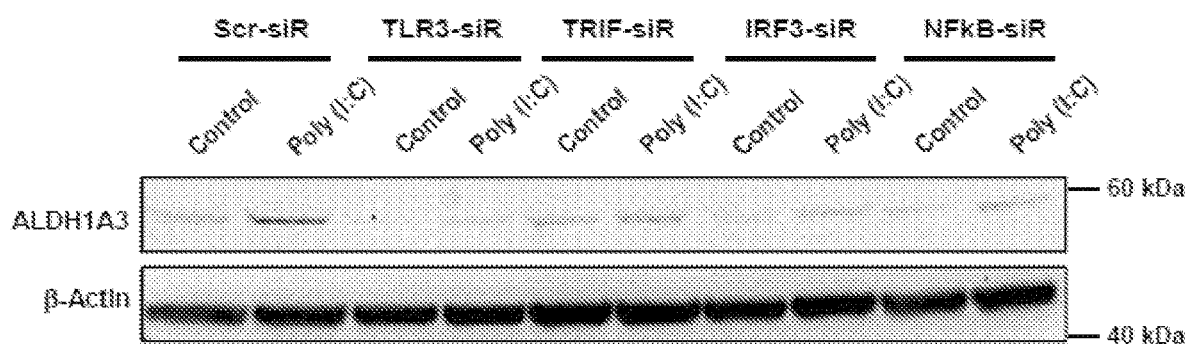
Figure 4E:
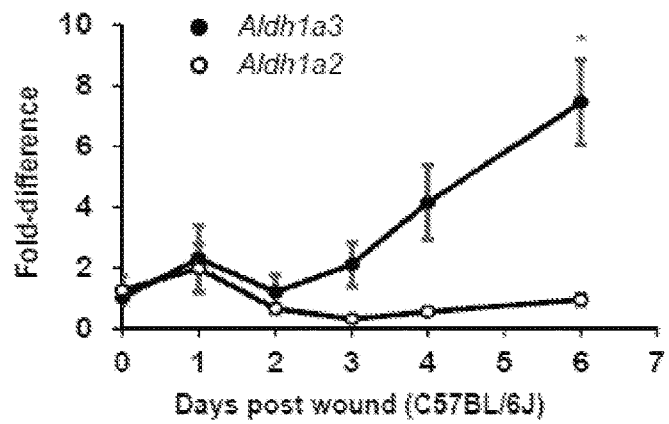
Figure 4F:
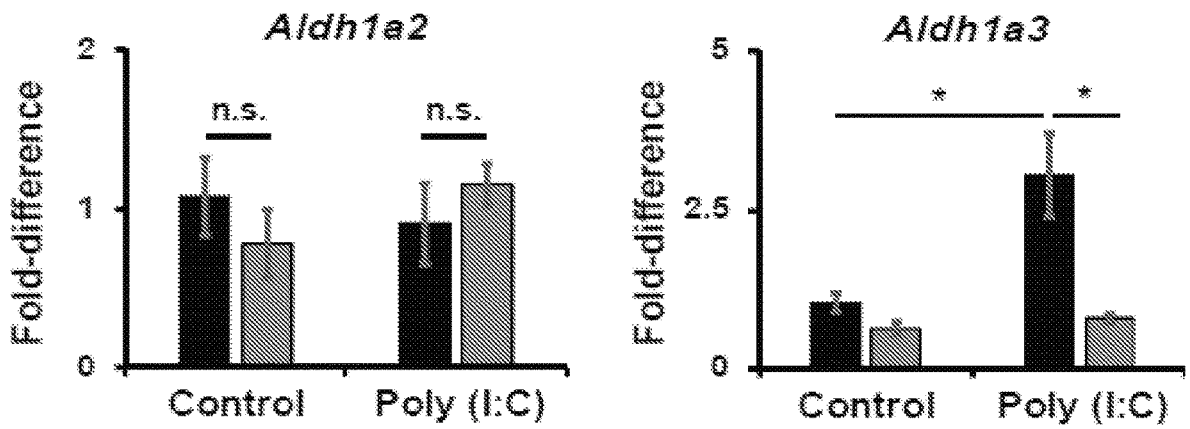
Figure 8A:
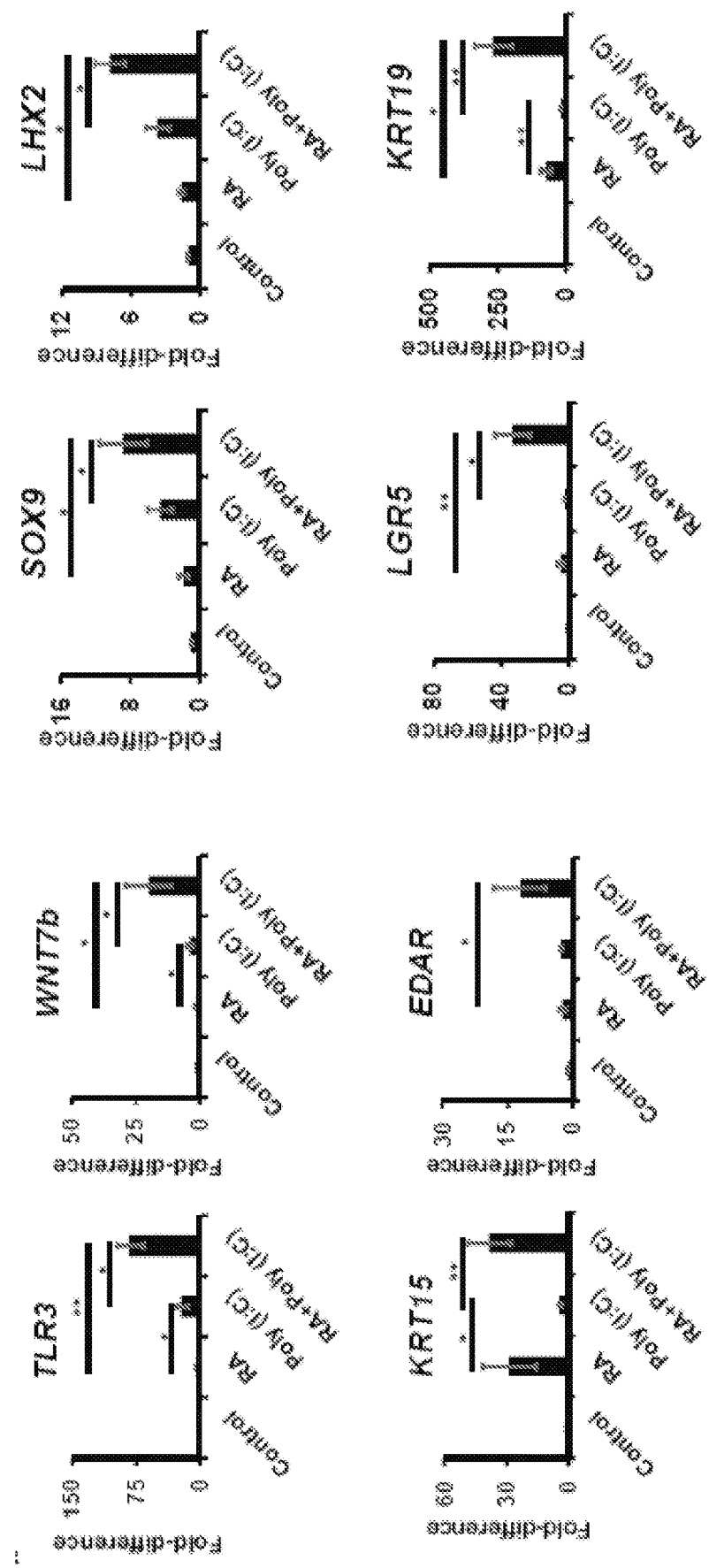
FIG. 8A-8D. Synergistic effects of RA and Poly (I:C).
Figure 8B:
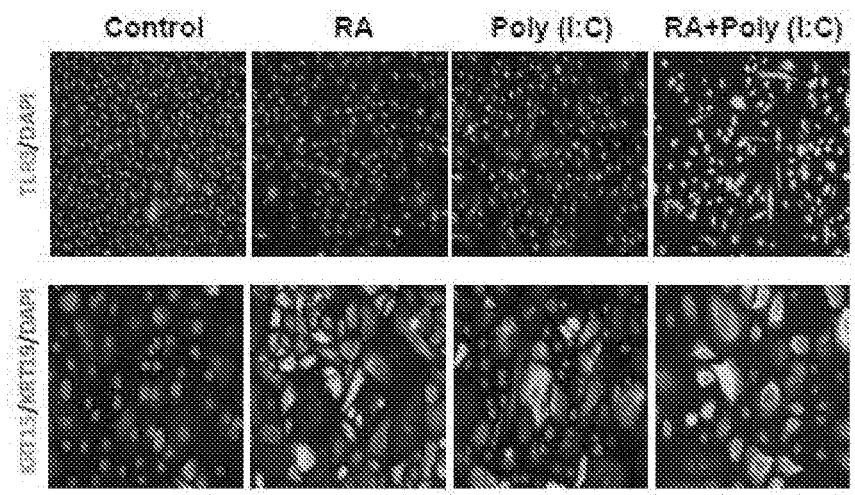
Figure 8C:
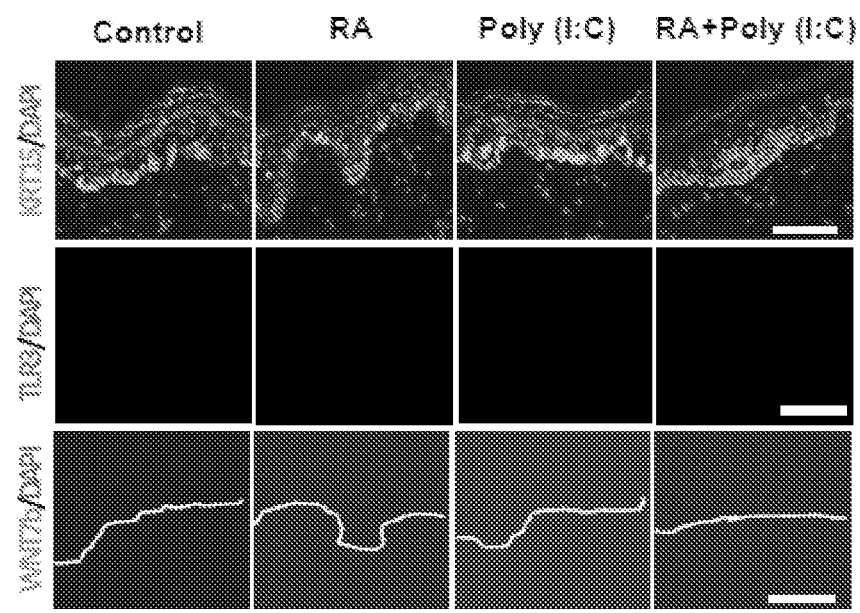
Figure 8D:
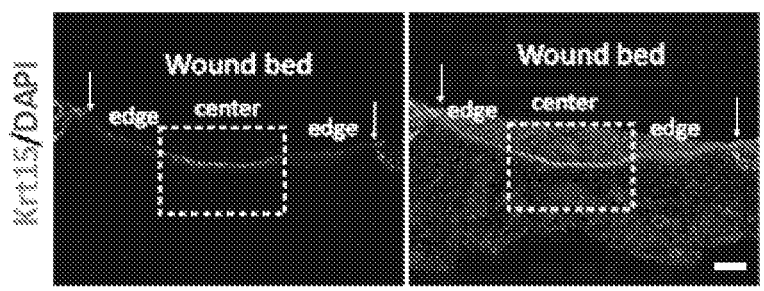
Figure 10:
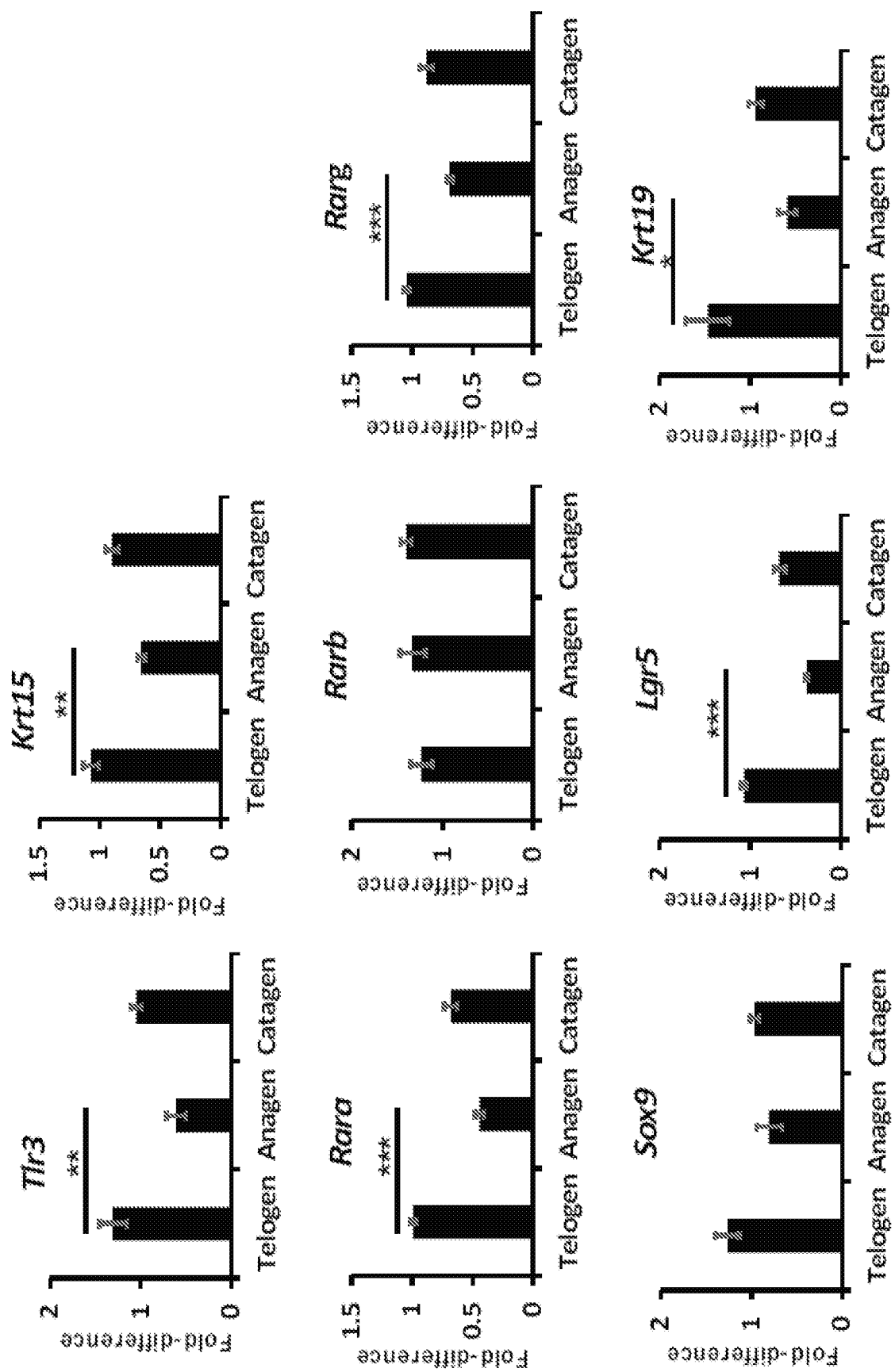
FIG. 10. Gene expression during the hair cycle. Relative mRNA expression of Tlr3, Krt15, Rara, Rarb, Rarg, Sox9, Lgr5, and Krt19 in Krt5-Cre mouse skin during the hair cycle. (n=4-7 independent animals, *P<0.05, P<0.01, *P<0.05, unpaired student t-test). Note coordinated expression of tested genes during the quiescent telogen phase. Data are means±SEM.

Our next aim was to define the mechanism of how dsRNA and TLR3 increase RA synthesis. To this end, the present inventors noted highly synergistic induction between Poly (I:C) and RA of transcription for key players thought to stimulate WIHN. Expression of KRT15, TLR3, Wingless and the name Int-1-7b (WNT7b) and Ectodysplasin A receptor (EDAR) were potently upregulated by a combination of RA and Poly (I:C) in cultured human keratinocytes and human skin explants (FIG. 8A-8C). Given the potency of combined RA and Poly (I:C), the present inventors hypothesized that an RA synthesis positive feedback loop enhances intrinsic RA synthesis and function. The present inventors therefore tested three enzymes known to convert retinal to RA (Aldehyde dehydrogenase 1 family, member A1-A3; ALDH1A1-A3) for synergistic response to RA and Poly (I:C) in human keratinocytes.

dsRNA induces RA synthesizing enzymes for RA accumulation. ALDH1A1 showed the least robust response and no synergistic activation to RA and Poly (I:C). However, ALDH1A3 and ALDH1A2 to a lesser extent were induced by RA and Poly (I:C) (FIG. 4A). ALDH1A3 protein was robustly increased by either RA or Poly (I:C), but particularly with both (FIG. 4A). To define the functional importance of ALDH1A2 and A3, the present inventors inhibited ALDH1A2/A3 in human keratinocytes with either siRNA or broad ALDH chemical inhibition (N,N-diethylaminobenzaldehyde; DEAB). Normally following Poly (I:C) stimulation, ALDH1A3 and the hair follicle stem cell markers KRT15 and KRT19 protein expression are upregulated, but this induction was disrupted with both methods of ALDH1A2/A3 inhibition (FIG. 4B). Moreover, Poly (I:C)-induced RA synthesis is dependent on ALDH1A2/A3 (FIG. 4C). Supporting this, TLR3 downstream genes are required for Poly (I:C) induction of ALDH1A3 in human keratinocytes (FIG. 4D). In wild type mice, ALDH1A3 is induced during late stage wounding, while ALDH1A2 is not (FIG. 4E). Indeed, in WT but not Tlr3$^{-/-}$ mice, Poly (I:C) induced Aldh1a3 transcription during wound healing, while Aldh1a2 did not show a similar pattern (FIG. 4E-4F). Taken together, these results demonstrate the functional importance of ALDH1A2/A3 in TLR3/dsRNA-induced stem cell marker induction and RA synthesis.

Figure 4G:
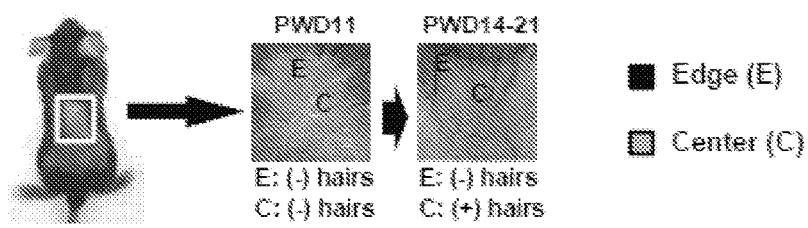
Figure 4G:
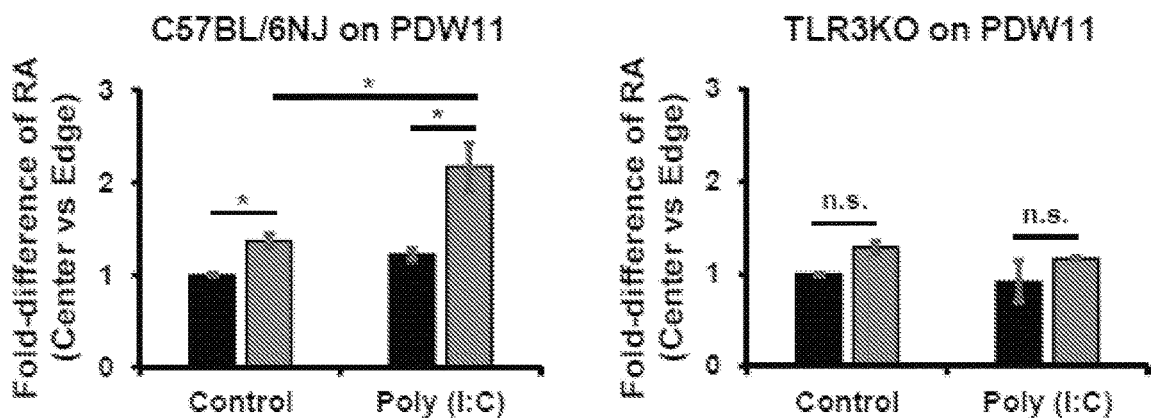
Figure 4H:
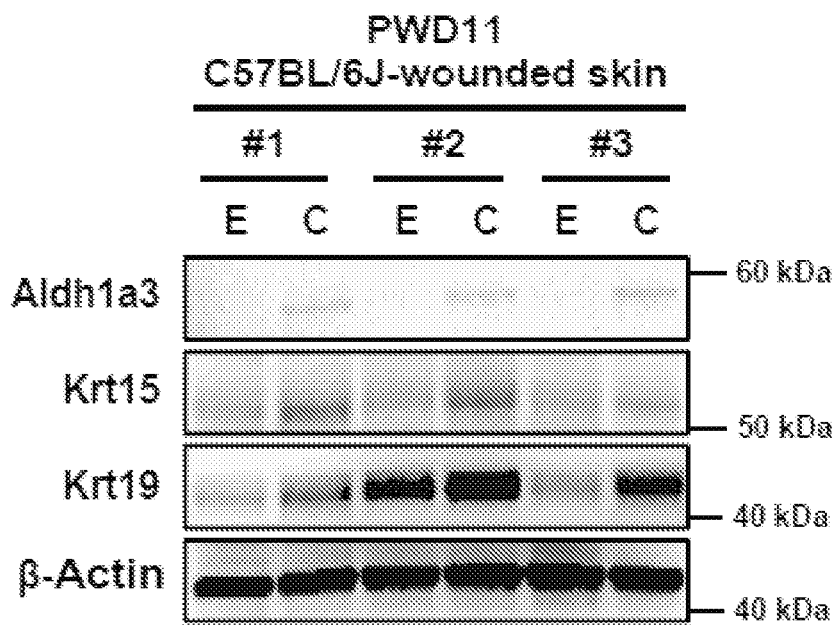
Figure 4I:
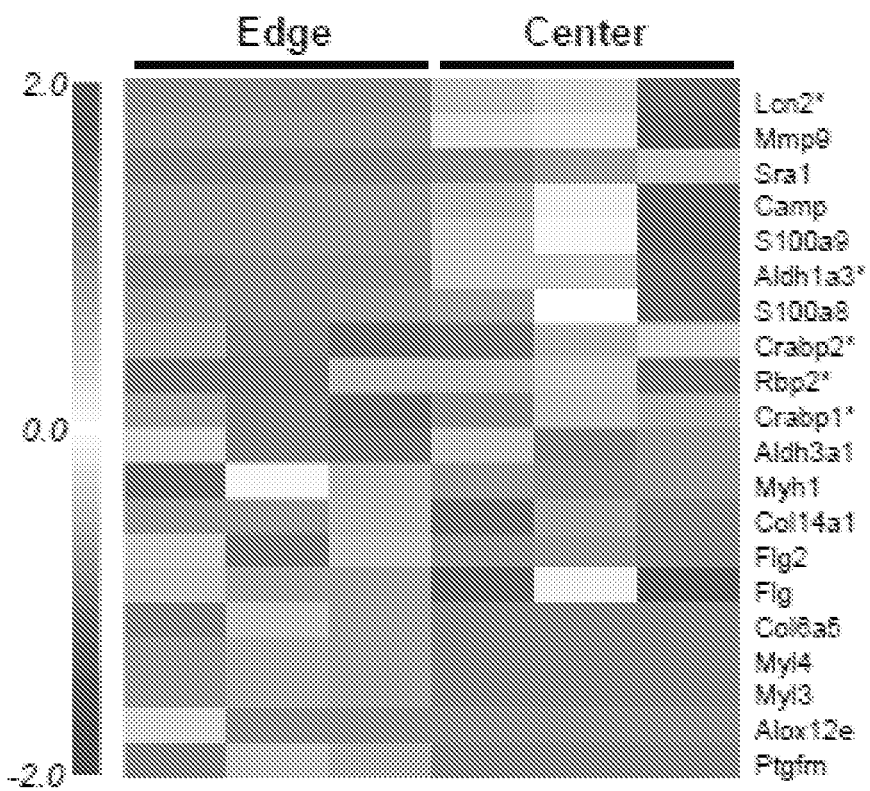

During WIHN, neogenic hair follicles form in the center of the wound and less so at the periphery. This patterning is reminiscent of developmental processes; RA defines the anterior/posterior axis by forming morphogen gradients during embryo development[10]. The present inventors therefore measured RA abundance in center versus edge skin areas after wound closure, but prior to the initiation of neogenic follicles (Post Wound Day 11; PWD11). Interestingly, RA levels were higher in the center and lower at the periphery (FIG. 4G), so that higher RA levels were detected in areas that later harbored more WIHN; conversely, lower RA levels were detected in areas that later harbored less WIHN. Consistent with this, at early pre-regeneration time-points, the center of wound expressed more Aldh1a3, Krt15, and Krt19 protein than the periphery (FIG. 4*h*H). Proteomics confirmed an abundance of RA-mediated signaling proteins in the center area of healed skin prior to regeneration (FIG.

4I). Therefore, dsRNA increased the abundance of RA, particularly in this center region, to establish an RA concentration differential for regeneration, suggesting that RA might directly enhance WIHN.

Figure 5A:
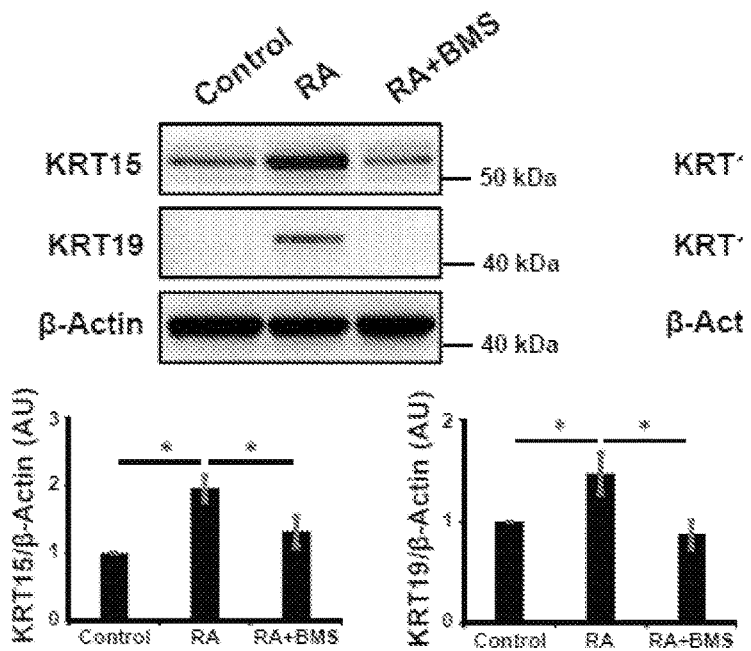
FIG. 5A-5I. Rarα is required for baseline and dsRNA augmented WIHN.
Figure 5B:
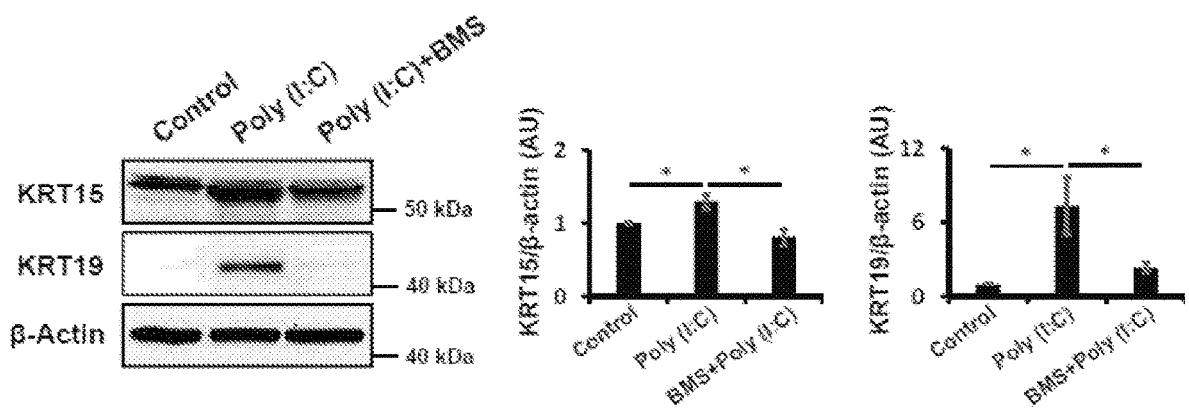
Figure 5C:
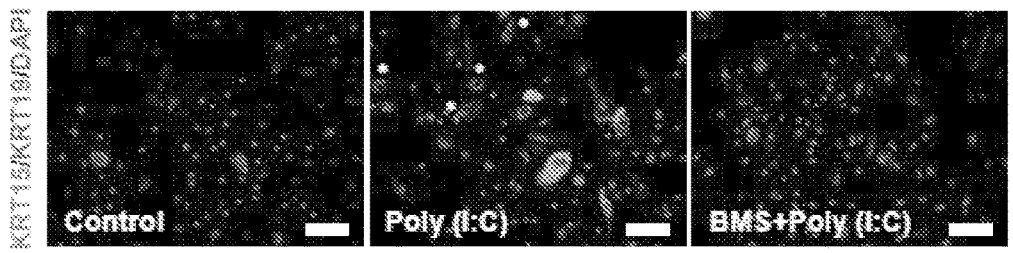
Figure 5D:
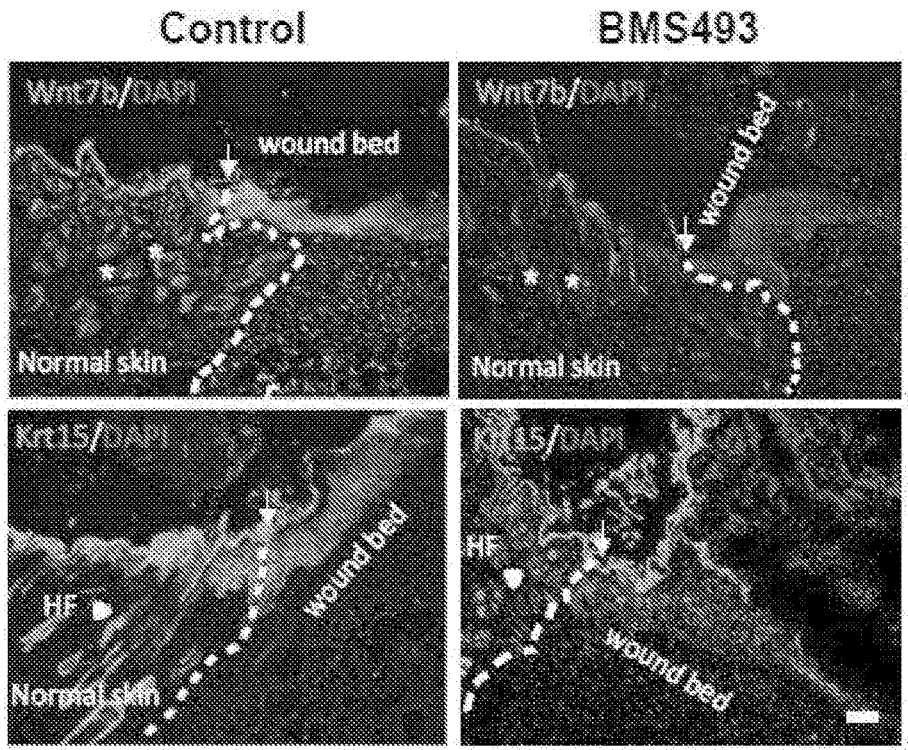
Figure 5E:
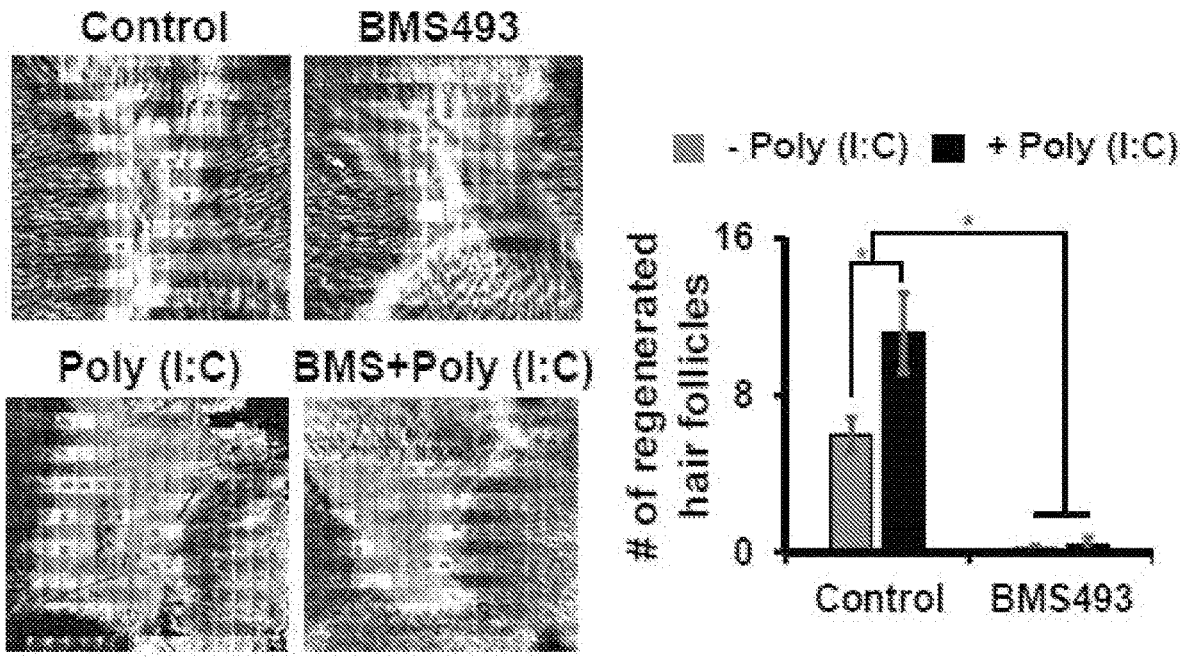

Rarα is necessary for baseline and dsRNA-augmented WIHN. Having defined the functional importance of dsRNA, TLR3, ALDH1A2/3 and RA, the present inventors next explored the mechanism by which RA controls regeneration. RA binds its receptors (RAR-alpha, beta, and gamma; RARα, RARβ, RARγ) to form heterodimers with retinoid X receptors (RXRs) and initiate gene transcription[20,21]. To investigate whether Poly (I:C)-induced RA signaling is required for hair follicle regeneration, the present inventors first inhibited RA signaling using a pharmacological pan-RAR antagonist (BMS493) in the presence of Poly (I:C). BMS493 substantially inhibited RA and Poly (I:C)-induced KRT15 and KRT19 expression in human keratinocytes (FIG. 5A-5C). The present inventors next investigated RAR inhibition in vivo. BMS493 treatment in WT mice decreased Wnt7b and Krt15 protein expression in wound beds prior to regeneration (FIG. 5D). Consistent with this, BMS493 treatment almost completely ablated all WIHN (FIG. 5E), with or without Poly (I:C). These results suggest that dsRNA-induced RA signaling after wounding is important to promote hair follicle neogenesis.

Figure 5F:
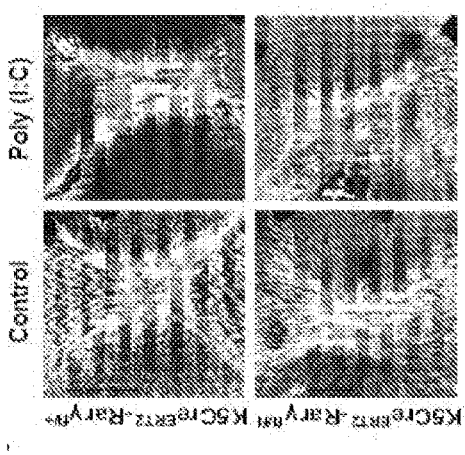
Figure 5F:
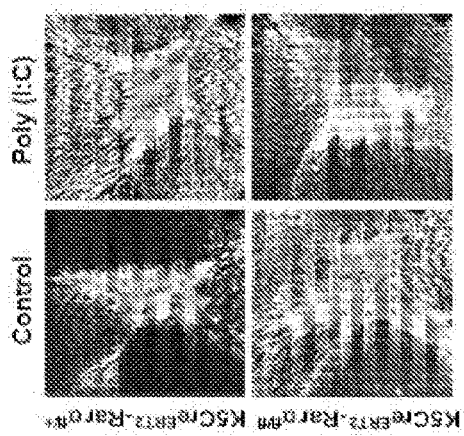
Figure 5F:
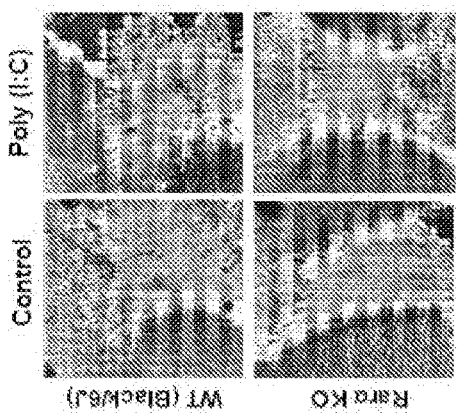
Figure 5F:
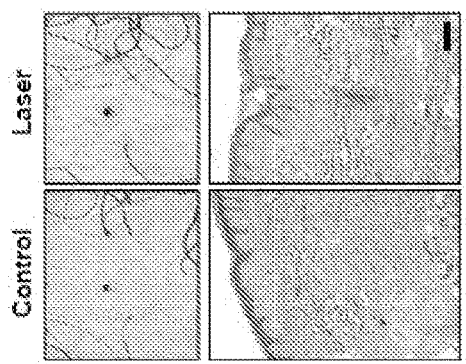
Figure 5F:
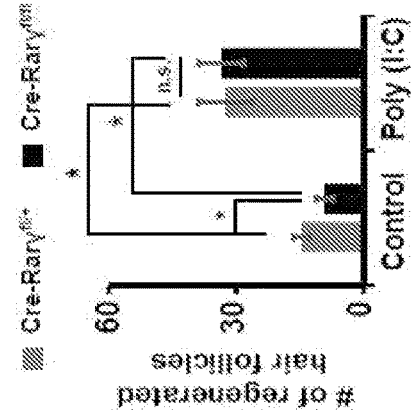
Figure 5G:
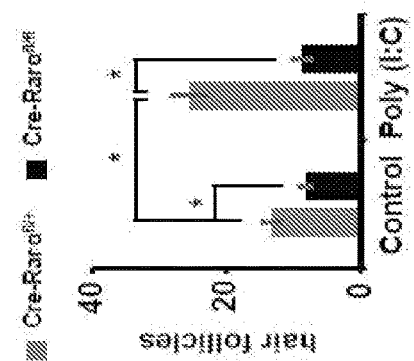
Figure 5H:
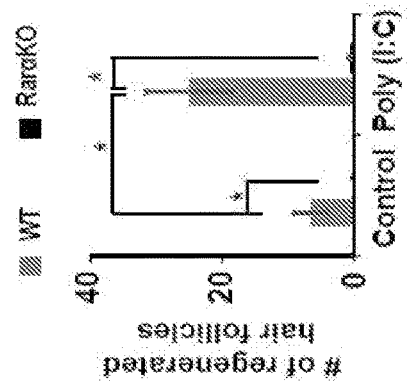

Given the potential off-target effects of pharmacologic inhibition the present inventors used genetic targeting to determine which specific RAR is important for regeneration. Since dsRNA/TLR3 signaling induces RA synthesis in human keratinocytes that express both RARα and RARγ, but not RARβ[22,23], the present inventors measured WIHN in keratinocyte-targeted Rarα and Rarγ null mice (Krt5-Cre-ERT2-Rarα$^{fl/fl}$ and Krt5-CreERT2-Rarγ$^{fl/fl}$). Keratinocyte-specific Rarγ deficient mice displayed mostly intact hair follicle regeneration (FIG. 5F) whereas the homozygous Rarα null mice (Krt5-CreERT2-Rarα$^{fl/fl}$) receiving vehicle or Poly (I:C) had a marked inhibition of hair follicle formation, compared to heterozygous mice (FIG. 5G). The effect of Rarα deletion on hair follicle regeneration was even more pronounced in in global Rarα null mice (FIG. 5H), possibly due to deletion in other contributing cell types, to more efficient gene deletion in keratinocytes, or both. Underscoring the possibility of cooperativity, combined RARα/γ deletion in keratinocytes also exhibited less WIHN (FIG. 9). These results demonstrate the importance of Retinoic Acid Receptors in responding to RA and enhancing regeneration.

Figure 5I:
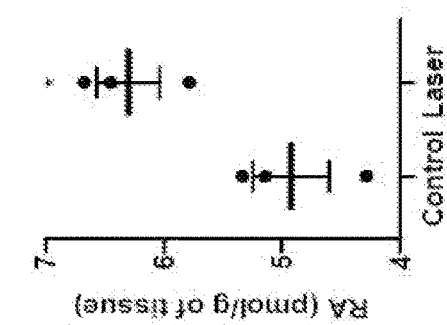

In human subjects, laser treatment induces RA accumulation. Finally, to assess the human relevance of these findings, the present inventors treated human subjects with a laser normally used for facial rejuvenation, and again discovered elevations in RA synthesis (FIG. 5I). These results demonstrate the importance of RA in the regulation of normal and dsRNA induced regeneration. Moreover, these data indicate that these conserved pathways despite highly distinct contexts are upregulated in common cosmetic procedures and highlight how dsRNA/damage induction of RA synthesis is central to rejuvenation therapies.

Discussion

Anti-viral inflammatory pathways are a conserved feature of multiple types of stem cells, but their non-immune function is unclear[8]. Also, RA has been demonstrated to be important for hematopoietic stem cell dormancy, limb development and even limb regeneration[10,11,24]. However, how these seemingly disparate features might be connected has not been clear. Based on TLR3 enhancement of healing after injury[9,25,26], the present inventors discovered that dsRNA/TLR3 stimulates a RA morphogen concentration differential to promote stem cell function in hair follicle neogenesis. These results suggest a broader and previously unrecognized connection of non-coding dsRNA sensing and RA signaling during development, regeneration, and likely normal functions.

The mechanistic link between damage induced dsRNA and RA synthesis that the present inventors demonstrate matches the clinical commonality of damage-based treatments and RA used in dermatology for skin rejuvenation. A wide variety of treatments such as dermabrasion, microneedling, peels, and lasers reverse fine wrinkling and pigmentary changes associated with photoaging. RA succeeds in this regard. Our current study implies that all of these therapies might work through the same final common pathway of activating RARs. Indeed, clinicians also have made the observation that RA pretreatment enhances outcomes in damage based treatments[27]. These clinical observations dovetail with the present inventors' findings of synergistic transcriptional responses in combined RA and dsRNA treated cells (FIG. 4 and FIG. 8). Therefore, the present findings provide a mechanistic explanation for these previous clinical observations and suggest future studies to examine whether controlled damage and RA can enhance tissue remodeling in organs other than skin.

RA has broad uses in medicine, for example in the treatment of acute promyelocytic leukemia. However, in all contexts, treatment can result in poor efficacy and significant side effects. This might partly be due to the artificial nature of exogenous RA delivery in these clinical settings; inducing endogenous synthesis might be far more effective, for example because of the simultaneous induction of chaperones. In support of this, the present inventors find that in conditions where ALDH1A3 is maximally induced, such as with RA plus Poly (I:C) (FIG. 4A), stem cell gene induction (FIG. 8) is also maximally induced—up to ~250 fold more than with exogenous RA treatment alone. This implies that methods of inducing nuclear steroid hormone ligand production will be more efficacious than simple ligand addition in their respective clinical indications.

Figure 11A:
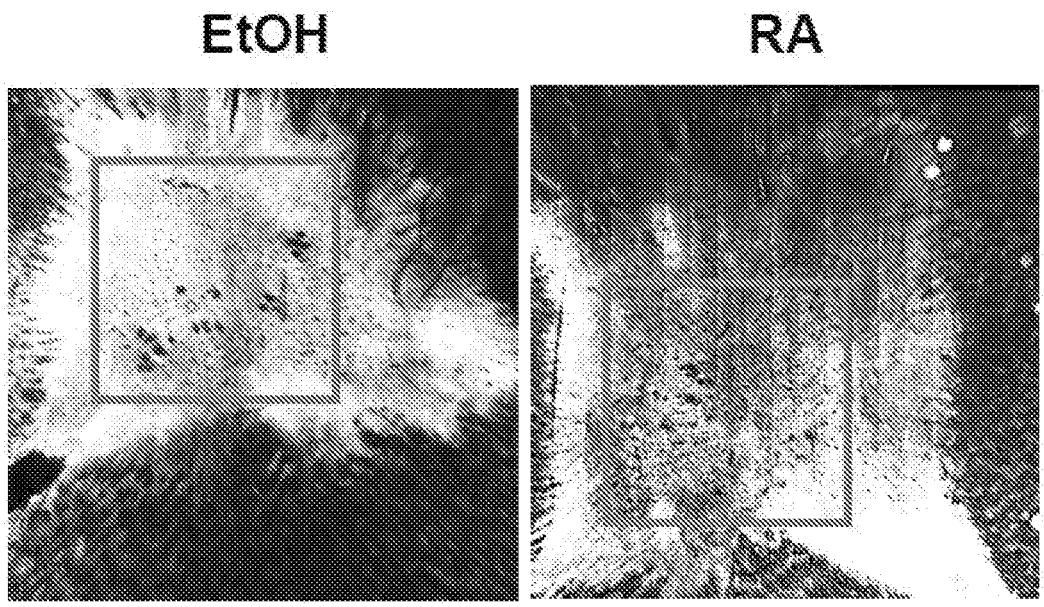
FIG. 11A-11B. Exogenous RA treatment in WT mice.
Figure 11B:
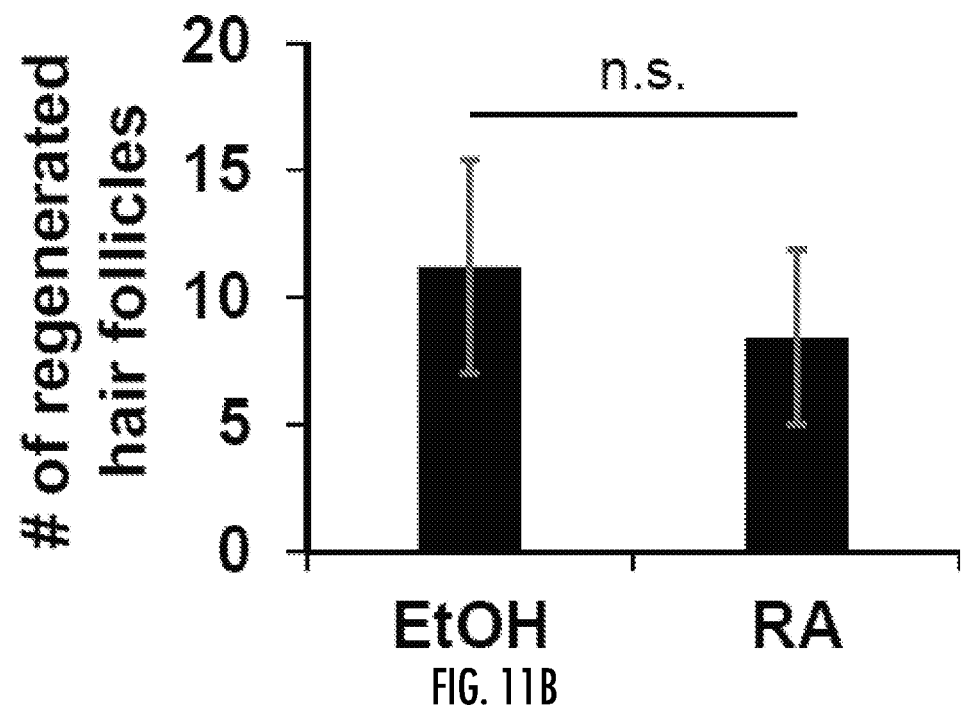
Figure 12A:
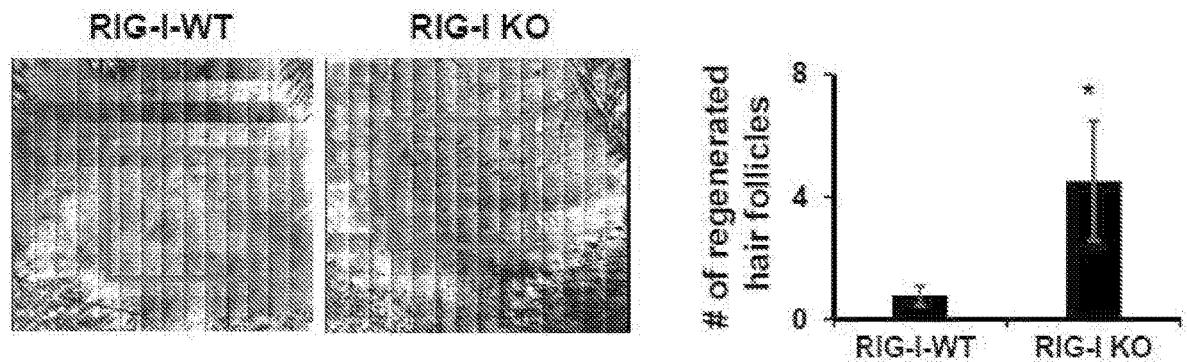
Figure 12B:
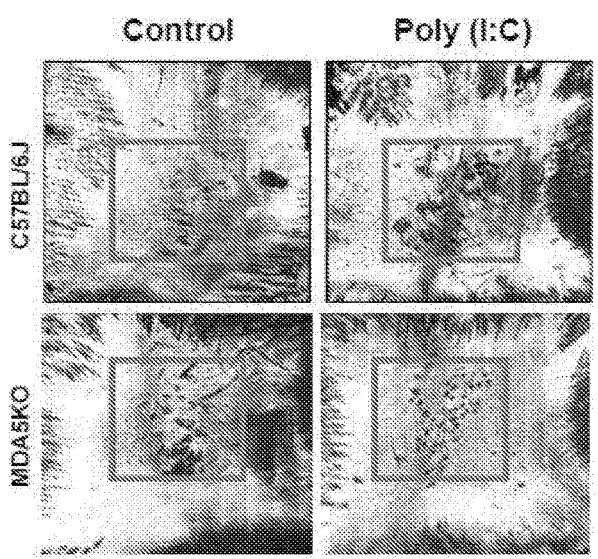
Figure 12B:
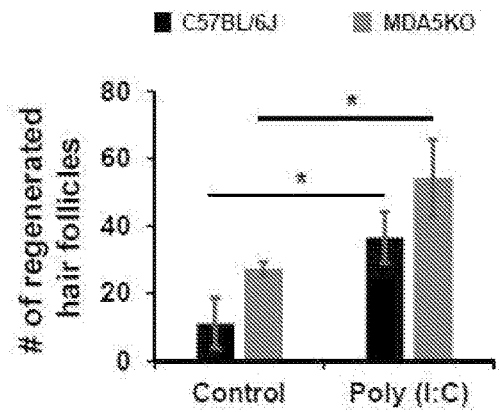
Figure 13A:
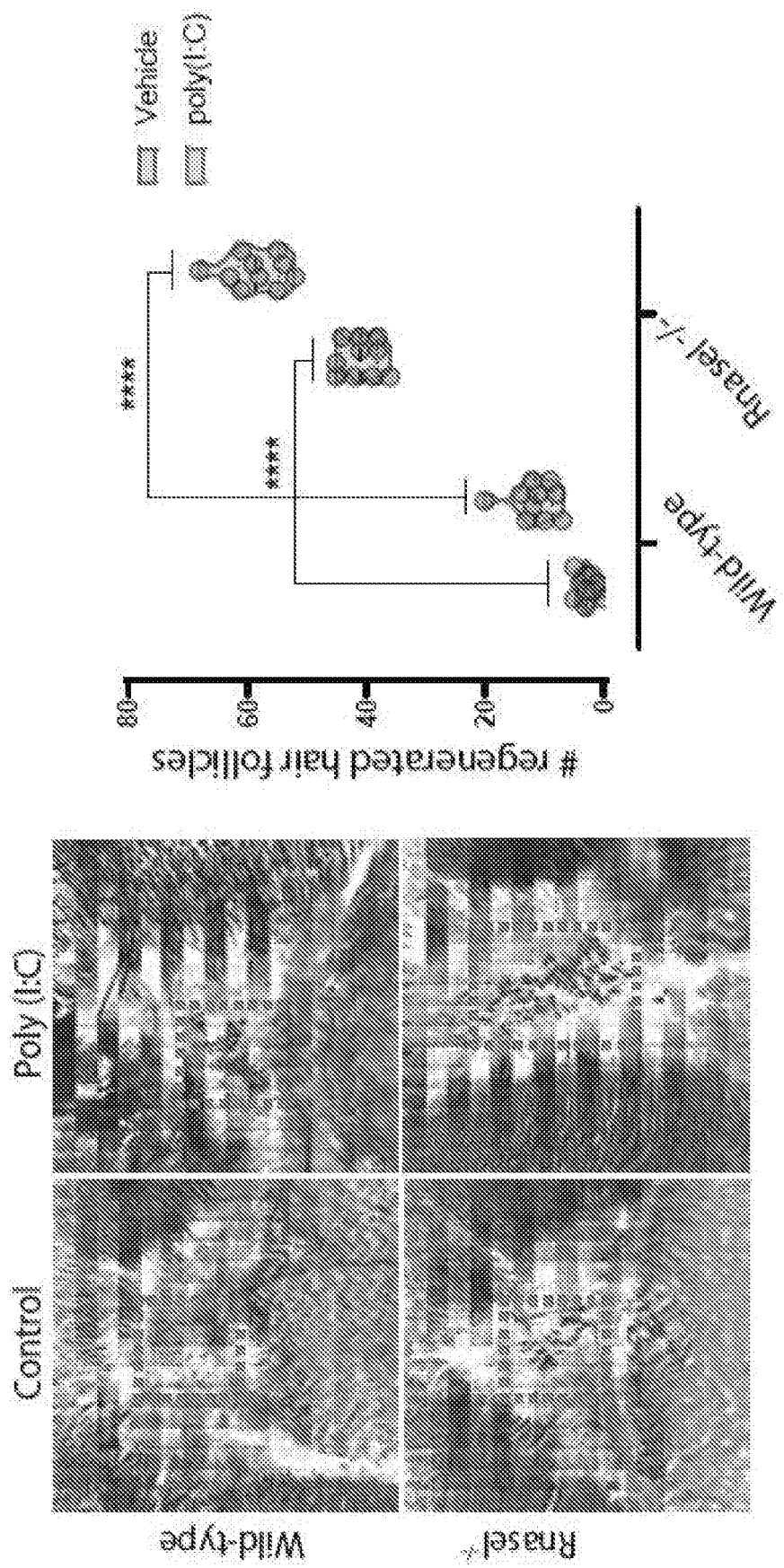
FIG. 13A-13C. RNase L loss enhances hair follicle regeneration (WIHN) and accelerates wound healing kinetics.
Figure 13B:
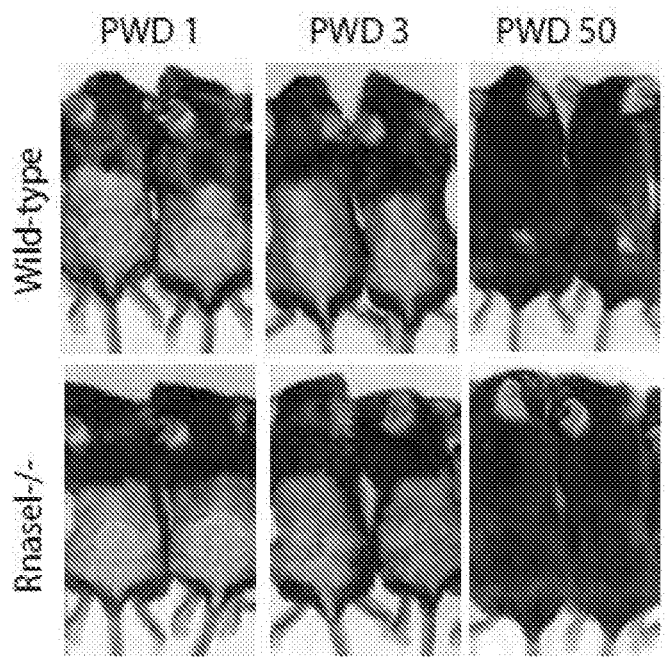
Figure 13C:
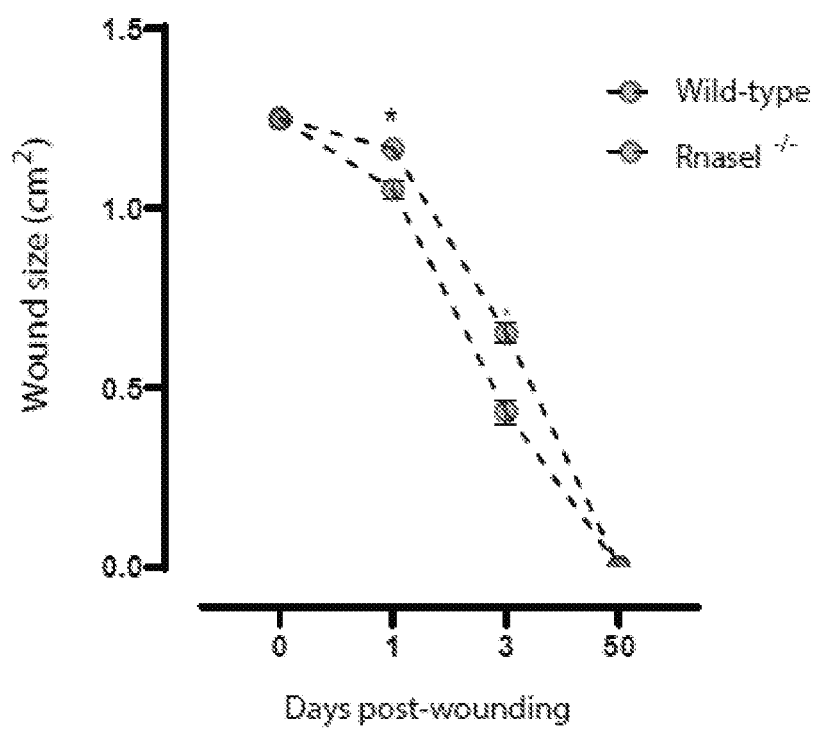
Figure 14A:
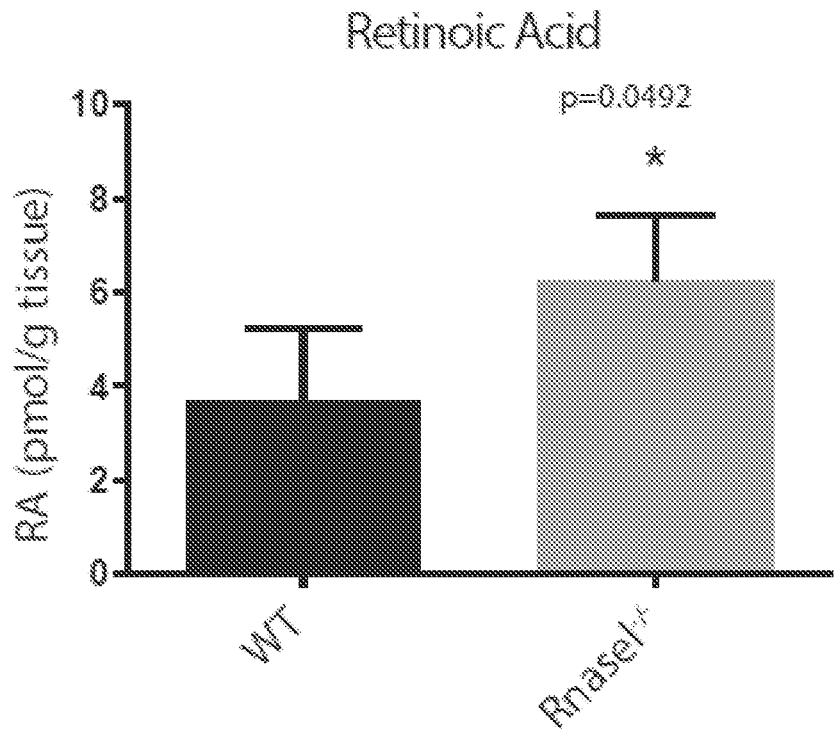
FIG. 14A-14C. Rnase1-/- mice have elevated levels of Retinoic Acid in skin.
Figure 14B:
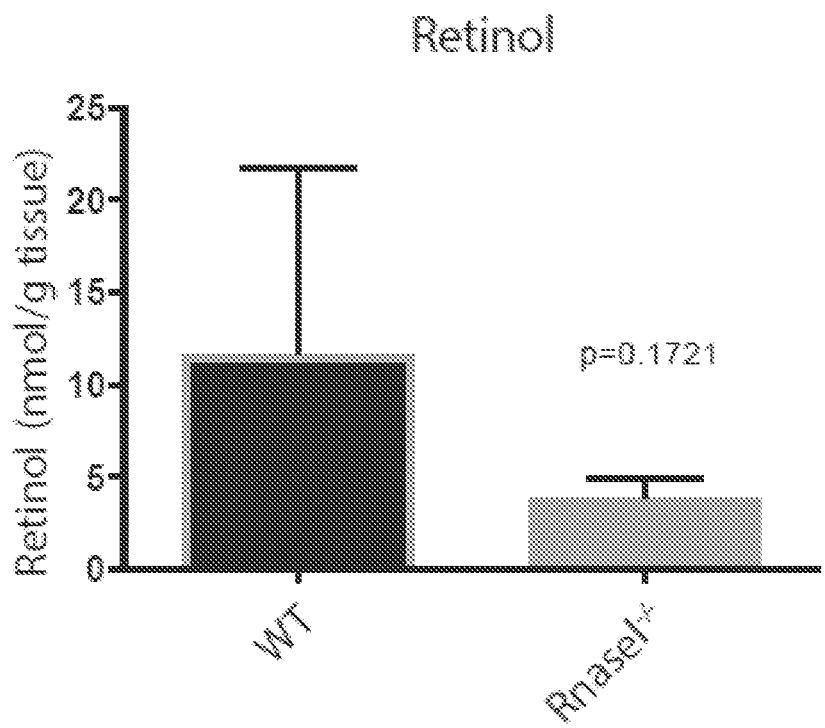
Figure 14C:
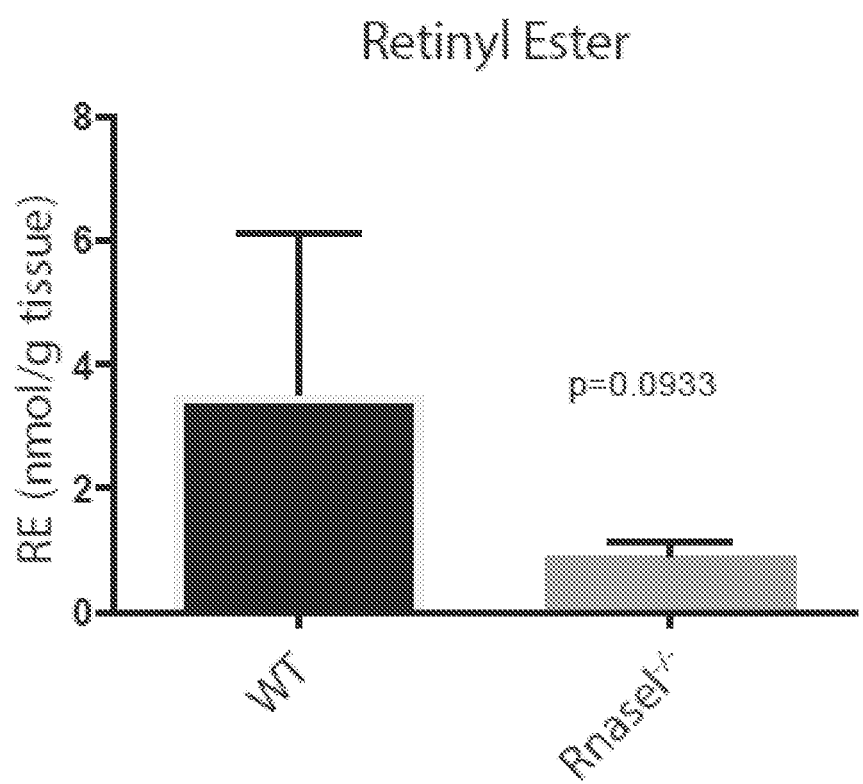

Our results raise other interesting questions. One is the potential role of non-TLR3 dsRNA sensors. For example, retinoic acid-inducible gene I (RIG-I/DDX58) and melanoma differentiation associated gene-5 (MDA5/IFIH1) recognize short and long dsRNAs, respectively[28]. The present inventors find that mice deficient in RIG-I or MDA5 are still capable of WIHN, though the background strain of RIG-I is unusually low (FIG. 12A-12B). Moreover, human keratinocytes deficient in these genes still induce RA synthesis after PIC treatment (FIG. 12C-12E), but this is not the case in TLR3 deficient cells (FIG. 2D, 2H-2I). Another question is related to the effect of supraphysiologic doses of RA in WIHN. Although RA is sufficient to increase WIHN in Tlr3$^{-/-}$ mice (FIG. 3D), and RA is required for WIHN in WT animals (FIG. 5), supraphysiologic doses of RA do not modify WIHN (FIG. 11). This occurs in other contexts of RA biology, and might be due to lack of chaperones or induction of degradation pathways that tightly regulate this potent biologic pathway. Biologic pathway differences might also relate to the differences the present inventors see in how RA abundance changes in different types of wounds; after human laser wounding, RA increases while the absolute level of RA appears lower in wounded mouse skin compared to unwounded skin. Perhaps the most likely explanation appears to be that hair follicles are rich in RA abundance, and their numbers are unchanged after human laser wounding, but dramatically decrease after full thickness skin excision in the present inventors' mouse model. Future work should investigate the contribution of adnexal structures to RA abundance, endogenous RA pathway regulation, the likely non-linear pathways regulating regeneration, and other non-TLR3 pathways in WIHN.

Altogether, the present inventors' results demonstrate that regeneration in adult organisms involves a recapitulation of a developmental morphogen gradient and signaling, which for example is consistent with the role of RA in salamander limb regeneration. Although there are differences between human facial rejuvenation and mouse WIHN, here the present inventors demonstrate how noncoding dsRNA activates TLR3 to trigger RA synthesis and signaling to promote regeneration. Our work implies that therapeutic combination of TLR3 agonists with RA might synergistically enhance regeneration in humans.

TABLE 1

Primer Sets for Genotyping

| Name | | Sequences (5'-3') | Product size (bp) |
|---|---|---|---|
| Cre | Forward | GAC CAG GTT CGT TCA CTC ATG G (SEQ ID NO: 2) | 200 |
| | Reverse | AGG CTA AGT GCC TTC TCT ACA C (SEQ ID NO: 3) | |
| Rarα flox | Forward | CAG GGA TGC TGT TTG TA (SEQ ID NO: 4) | WT; 156 Mut: 189 |
| | Reverse | CCT ATG ACC CAG GAC TCA GC (SEQ ID NO: 5) | |
| Rarγ flox | Forward | AGC TCA GTG GAA TGC TT (SEQ ID NO: 6) | WT; 240 Mut: 280 |
| | Reverse | TTT TCT GAA TGC GTC TG (SEQ ID NO: 7) | |
| Rarα KO | Forward | TTT GCC TGC TCT GAC TG (SEQ ID NO: 8) | |
| | Reverse (WT) | ACG GTG TGC TGT AAC CAC TG (SEQ ID NO: 9) | WT; 201 |
| | Reverse (Mut) | GCC AGA GGC CAC TTG TGT AG (SEQ ID NO: 10) | Mut; 165 |
| Tlr3 KO | Forward | AAT TCA GTG CCA TGA GTT T (SEQ ID NO: 11) | |
| | Reverse (WT) | GCA ACC CTT TCA AAA ACC AG (SEQ ID NO: 12) | WT; 341 |

TABLE 1-continued

Primer Sets for Genotyping

| Name | | Sequences (5'-3') | Product size (bp) |
|---|---|---|---|
| | Reverse (Mut) | GCC AGA GGC CAC TTG TGT AG (SEQ ID NO: 13) | Mut; 208 |

TABLE 2

Antibodies Used for Western Blot and Immunostaining

| Name | Host | Dilution Western blot | Immunostaining | Company/Cat No. |
|---|---|---|---|---|
| TLR3 | mouse | | 1:300 | Santa Cruz Biotechnology #sc-32232 |
| KRT19 | Mouse | 1:2,000 | 1:300 | Invitrogen, #MA5-12663 |
| KRT15 | Rabbit | 1:2,000 | 1:300 | Sigma, HPA023910 |
| ALDH1A3 | Rabbit | 1:1,000 | | Invitrogen, #PA5-61201 |
| β-Actin | Rabbit | 1:1,000 | | Cell Signaling Technology, #4967L |
| β-catenin | mouse | 1:1,000 | | Millipore, 610153 |
| Active β-catenin | mouse | 1:1,000 | | Millipore, #05-665/ clone 8E7 |
| WNT7b | Rabbit | | 1:200 | Abcam, #ab94915 |
| Alexa Fluor® 488 Anti-Rabbit IgG (H + L) | Goat | | 1:1,000 | Life Technologies, A-11034 |
| Alexa Fluor® 594 Anti-Rabbit IgG (H + L) | Goat | | 1:1,000 | Life Technologies, A-11037 |
| anti-mouse IgG-HRP | | 1:1,000 | | Cell Signaling Technology; #7076S |
| anti-rabbit IgG-HRP | | 1:1,000 | | Cell Signaling Technology; #7074S |

TABLE 3

Antibodies Used for Western Blot and Immunostaining
D15: 15th day after born, WD3: 3rd day after wounding

| Mouse | Mouse strain | Treatment | Vehicle | Day of treatment | Note |
|---|---|---|---|---|---|
| Wild type (WT) | C57BL/6J | Poly (I:C) BM5493 | PBS DMSO | WD3 WD1 | JAX stock #00664 |
| Wild type (WT) | C57BL/6NJ | Poly (I:C) RA | PBS Ethanol | WD3 WD1 | JAX stock #005304 Used for Tlr3-/- |
| Tlr3-/- | B6N.129S1-Tlr3$^{tm1Flv}$/J | Poly (I:C) RA | PBS Ethanol | WD3 WD1 | JAX stock #009675 |
| Mda5-/- | B6.Cg-Ifih1$^{tm1.1Cln}$/J | Poly (I:C) | PBS | WD3 | JAX stock #015812 |
| Rig-/- | 1295v/ C57BL/6-Ddx58 | | | | No treatment |
| Rigi-WT | 1295v/ C57BL/6 | | | | No treatment |
| Rarα-/- | Rara$^{tm1Rev}$/ HsvJ | Poly (I:C) | PBS | WD3 | JAX stock #023845 |

TABLE 3-continued

Antibodies Used for Western Blot and Immunostaining
D15: 15th day after born, WD3: 3rd day after wounding

| Mouse | Mouse strain | Treatment | Vehicle | Day of treatment | Note |
|---|---|---|---|---|---|
| Krt5-CreERT2 | C57BL/6J | Tamoxifen | Corn oil | D15 to WD3 | Crossed with floxed mice |
| Rarα$^{fl/fl}$ | C57BL/6J-Rarα foxed | Tamoxifen | Corn oil | D15 to WD3 | Crossed with Krt5-CreERT2 mice |
| Rarγ$^{fl/fl}$ | C57BL/6J-Rarγ foxed | Tamoxifen | Corn oil | D15 to WD3 | |
| Rarα-Rarγ$^{fl/fl}$ | C57BL/6J-Rarα-Rarγ foxed (double floxed) | Tamoxifen | Corn oil | D15 to WD3 | |

References

1. Ito, M. et al. Wnt-dependent de novo hair follicle regeneration in adult mouse skin after wounding. Nature 447, 316-320, doi:10.1038/nature05766 (2007).
2. Breedis, C. Regeneration of hair follicles and sebaceous glands from the epithelium of scars in the rabbit. Cancer Res 14, 575-579 (1954).
3. Wang, X. et al. Principles and mechanisms of regeneration in the mouse model for wound-induced hair follicle neogenesis. Regeneration (Oxford, England) 2, 169-181, doi:10.1002/reg2.38 (2015).
4. Takeo, M., Lee, W. & Ito, M. Wound Healing and Skin Regeneration. Cold Spring Harbor Perspectives in Medicine 5, a023267, doi:10.1101/cshperspect.a023267 (2015).
5. Lim, C. H. et al. Hedgehog stimulates hair follicle neogenesis by creating inductive dermis during murine skin wound healing. Nature communications 9, 4903, doi:10.1038/s41467-018-07142-9 (2018).
6. Gay, D. et al. Fgf9 from dermal gammadelta T cells induces hair follicle neogenesis after wounding. Nat Med 19, 916-923, doi:10.1038/nm.3181 (2013).
7. Plikus, M. V. et al. Regeneration of fat cells from myofibroblasts during wound healing. Science 355, 748-752, doi:10.1126/science.aai8792 (2017).
8. Wu, X. et al. Intrinsic Immunity Shapes Viral Resistance of Stem Cells. Cell 172, 423-438 e425, doi:10.1016/j.cell.2017.11.018 (2018).
9. Nelson, A. M. et al. dsRNA Released by Tissue Damage Activates TLR3 to Drive Skin Regeneration. Cell Stem Cell 17, 139-151, doi:10.1016/j.stem.2015.07.008 (2015).
10. Duester, G. Retinoic acid synthesis and signaling during early organogenesis. Cell 134, 921-931, doi:10.1016/j.cell.2008.09.002 (2008).
11. Stocum, D. L. Mechanisms of urodele limb regeneration. Regeneration (Oxford, England) 4, 159-200, doi:10.1002/reg2.92 (2017).
12. Li, M. et al. RXR-alpha ablation in skin keratinocytes results in alopecia and epidermal alterations. Development (Cambridge, England) 128, 675-688 (2001).
13. Okano, J. et al. Cutaneous retinoic acid levels determine hair follicle development and downgrowth. The Journal of biological chemistry 287, 39304-39315, doi:10.1074/jbc.M112.397273 (2012).
14. Fisher, G. J. et al. Molecular basis of sun-induced premature skin ageing and retinoid antagonism. Nature 379, 335-339, doi:10.1038/379335a0 (1996).
15. Canino, C. et al. A STAT3-NFkB/DDIT3/CEBPbeta axis modulates ALDH1A3 expression in chemoresistant cell subpopulations. Oncotarget 6, 12637-12653, doi: 10.18632/oncotarget.3703 (2015).
16. Cabezas-Wallscheid, N. et al. Vitamin A-Retinoic Acid Signaling Regulates Hematopoietic Stem Cell Dormancy. Cell 169, 807-823 e819, doi:10.1016/j.cell.2017.04.018 (2017).
17. Lai, Y. et al. Commensal bacteria regulate Toll-like receptor 3-dependent inflammation after skin injury. Nat Med 15, 1377-1382, doi:10.1038/nm.2062 nm.2062 [pii] (2009).
18. Bernard, J. J. et al. Ultraviolet radiation damages self noncoding RNA and is detected by TLR3. Nat Med, doi:10.1038/nm.2861 nm.2861 [pii] (2012).
19. Ito, M. et al. Stem cells in the hair follicle bulge contribute to wound repair but not to homeostasis of the epidermis. Nat Med 11, 1351-1354 (2005).
20. Rhinn, M. & Done, P. Retinoic acid signalling during development. Development 139, 843 (2012).
21. Cunningham, T. J. & Duester, G. Mechanisms of retinoic acid signalling and its roles in organ and limb development. Nature Reviews Molecular Cell Biology 16, 110, doi:10.1038/nrm3932 (2015).
22. Elder, J. T. et al. Retinoic acid receptor gene expression in human skin. The Journal of investigative dermatology 96, 425-433 (1991).
23. Viallet, J. P. & Dhouailly, D. Retinoic acid and mouse skin morphogenesis. I. Expression pattern of retinoic acid receptor genes during hair vibrissa follicle, plantar, and nasal gland development. The Journal of investigative dermatology 103, 116-121 (1994).
24. Cabezas-Wallscheid, N. et al. Vitamin A-Retinoic Acid Signaling Regulates Hematopoietic Stem Cell Dormancy. Cell 169, 807-823.e819, doi:10.1016/j.cell.2017.04.018 (2018).
25. Bernard, J. J. et al. Ultraviolet radiation damages self noncoding RNA and is detected by TLR3. Nature medicine 18, 1286-1290, doi:10.1038/nm.2861 (2012).
26. Zhang, L. J. et al. Antimicrobial Peptide LL37 and MAVS Signaling Drive Interferon-beta Production by Epidermal Keratinocytes during Skin Injury. Immunity 45, 119-130, doi:10.1016/j.immuni.2016.06.021 (2016).
27. Mandy, S. H. Tretinoin in the preoperative and postoperative management of dermabrasion. J Am Acad Dermatol 15, 878-879, 888-879 (1986).
28. Kato, H. et al. Length-dependent recognition of double-stranded ribonucleic acids by retinoic acid-inducible gene-I and melanoma differentiation-associated gene 5. The Journal of experimental medicine 205, 1601-1610, doi:10.1084/jem.20080091 (2008).
29. Normand, J. & Karasek, M. A. A method for the isolation and serial propagation of keratinocytes, endothelial cells, and fibroblasts from a single punch biopsy of human skin. In Vitro Cell Dev Biol Anim 31, 447-455, doi:10.1007/BF02634257 (1995).
30. Garza, L. A. et al. Bald scalp in men with androgenetic alopecia retains hair follicle stem cells but lacks CD200-rich and CD34-positive hair follicle progenitor cells. The Journal of clinical investigation 121, 613-622, doi: 10.1172/jci44478 (2011).
31. Aasen, T. & Izpisua Belmonte, J. C. Isolation and cultivation of human keratinocytes from skin or plucked hair for the generation of induced pluripotent stem cells. Nature protocols 5, 371-382, doi:10.1038/nprot.2009.241 (2010).

32. Chapman, S., Liu, X., Meyers, C., Schlegel, R. & McBride, A. A. Human keratinocytes are efficiently immortalized by a Rho kinase inhibitor. The Journal of clinical investigation 120, 2619-2626, doi:10.1172/jci42297 (2010).
33. Myung, P. S., Takeo, M., Ito, M. & Atit, R. P. Epithelial Wnt ligand secretion is required for adult hair follicle growth and regeneration. The Journal of investigative dermatology 133, 31-41, doi:10.1038/jid.2012.230 (2013).
34. Zhu, A. S., Li, A., Ratliff, T. S., Melsom, M. & Garza, L. A. After Skin Wounding, Noncoding dsRNA Coordinates Prostaglandins and Wnts to Promote Regeneration. The Journal of investigative dermatology 137, 1562-1568, doi:10.1016/j.jid.2017.03.023 (2017).
35. Wisniewski, J. R., Zougman, A., Nagaraj, N. & Mann, M. Universal sample preparation method for proteome analysis. Nature methods 6, 359-362, doi:10.1038/nmeth.1322 (2009).
36. Erde, J., Loo, R. R. O. & Loo, J. A. Enhanced FASP (eFASP) to Increase Proteome Coverage and Sample Recovery for Quantitative Proteomic Experiments. Journal of Proteome Research 13, 1885-1895, doi:10.1021/pr4010019 (2014).
37. Williamson, J. C. et al. High-performance hybrid Orbitrap mass spectrometers for quantitative proteome analysis: Observations and implications. Proteomics 16, 907-914, doi:10.1002/pmic.201400545 (2016).
38. Dorfer, V. et al. M S Amanda, a universal identification algorithm optimized for high accuracy tandem mass spectra. J Proteome Res 13, 3679-3684, doi:10.1021/pr500202e (2014).
39. Kall, L., Canterbury, J. D., Weston, J., Noble, W. S. & MacCoss, M. J. Semi-supervised learning for peptide identification from shotgun proteomics datasets. Nature methods 4, 923-925, doi:10.1038/nmeth1113 (2007).
40. Kramer, A., Green, J., Pollard, J., Jr. & Tugendreich, S. Causal analysis approaches in Ingenuity Pathway Analysis. Bioinformatics (Oxford, England) 30, 523-530, doi: 10.1093/bioinformatics/btt703 (2014).
41. Mi, H. et al. PANTHER version 11: expanded annotation data from Gene Ontology and Reactome pathways, and data analysis tool enhancements. Nucleic acids research 45, D183-D189, doi:10.1093/nar/gkw1138 (2017).
42. Huang da, W., Sherman, B. T. & Lempicki, R. A. Systematic and integrative analysis of large gene lists using DAVID bioinformatics resources. Nature protocols 4, 44-57, doi:10.1038/nprot.2008.211 (2009).
43. Jones, J. W., Pierzchalski, K., Yu, J. & Kane, M. A. Use of fast HPLC multiple reaction monitoring cubed for endogenous retinoic acid quantification in complex matrices. Anal Chem 87, 3222-3230, doi:10.1021/ac504597q (2015).
44. Kane, M. A., Chen, N., Sparks, S. & Napoli, J. L. Quantification of endogenous retinoic acid in limited biological samples by LC/MS/MS. Biochem J 388, 363-369, doi:10.1042/BJ20041867 (2005).
45. Kane, M. A., Folias, A. E., Wang, C. & Napoli, J. L. Quantitative profiling of endogenous retinoic acid in vivo and in vitro by tandem mass spectrometry. Anal Chem 80, 1702-1708, doi:10.1021/ac702030f (2008).
46. Kane, M. A. & Napoli, J. L. Quantification of endogenous retinoids. Methods Mol Biol 652, 1-54, doi: 10.1007/978-1-60327-325-1_1 (2010).
47. Kane, M. A., Folias, A. E. & Napoli, J. L. HPLC/UV quantitation of retinal, retinol, and retinyl esters in serum and tissues. Anal Biochem 378, 71-79, doi:10.1016/j.ab.2008.03.038 (2008).
48. Livak, K. J. & Schmittgen, T. D. Analysis of relative gene expression data using real-time quantitative PCR and the 2(−Delta Delta C(T)) Method. Methods (San Diego, Calif.) 25, 402-408, doi:10.1006/meth.2001.1262 (2001).

Example 2: A Combination Sequential Use Product Comprising Topical Retinoic Acid (0.001% to 1%) Followed by a Topical or Injected dsRNA to Combat Fine Skin Wrinkles Retinoic acid is commonly used as a topical drug to decrease fine wrinkles associated with aging. The present inventors have discovered that retinoic works synergistically with dsRNA to promote rejuvenation. In particular embodiments, the combination works well in the sequential order of retinoic first and then dsRNA, in particular, for combating skin aging.

Figure 15:
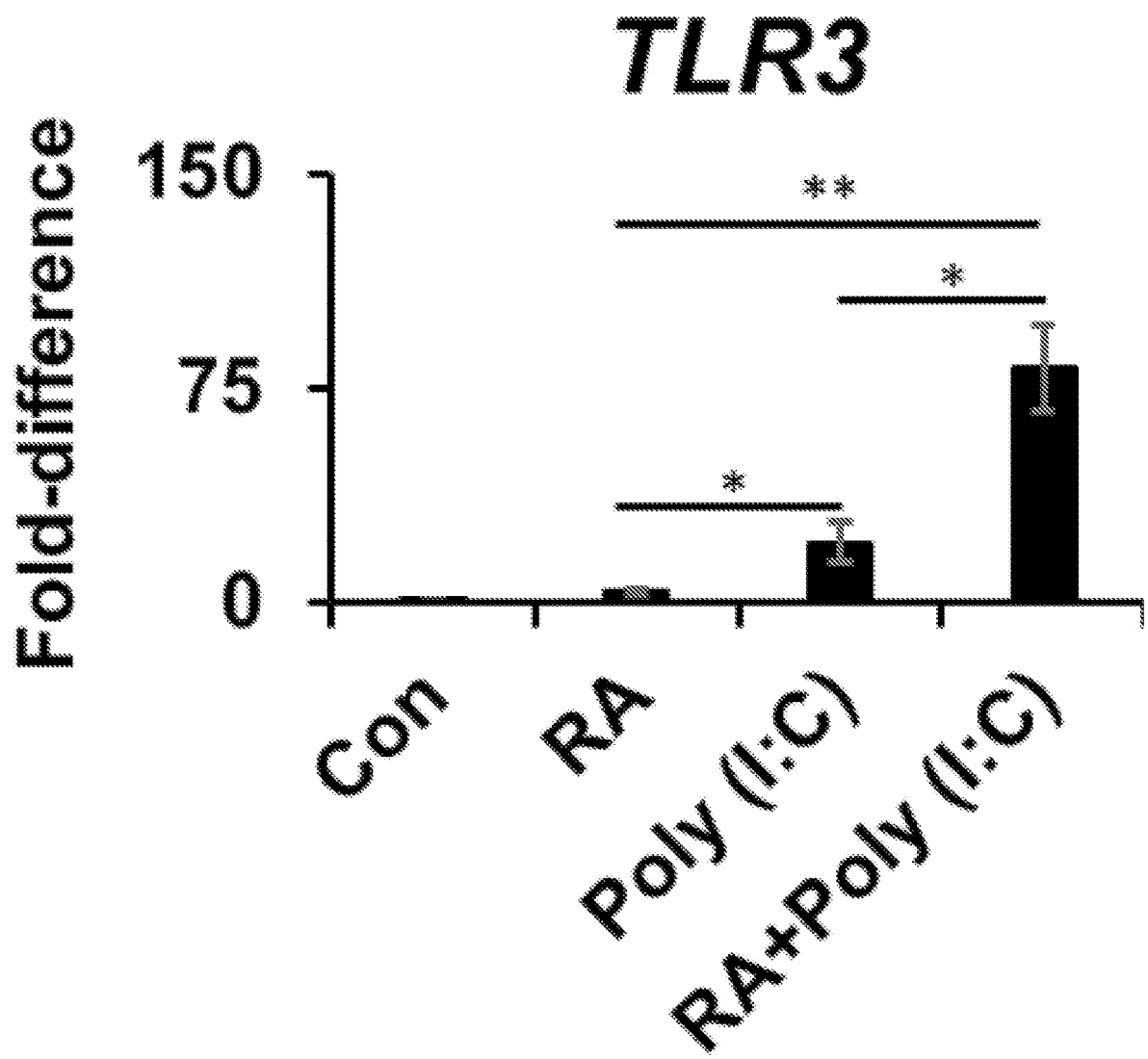
FIG. 15. TLR3 is a marker of rejuvenation in the skin and increases synergistically with both dsRNA and RA.
Figure 16:
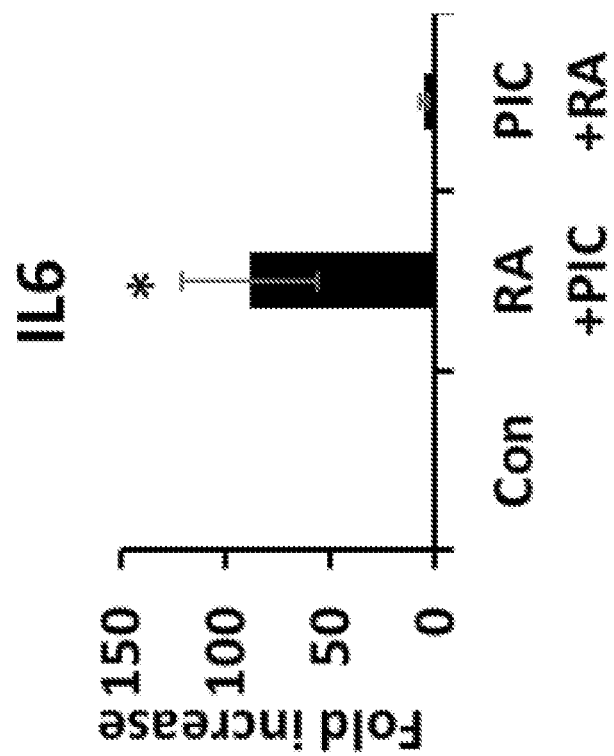
FIG. 16. TLR3 and IL-6 respond well in embodiments in which RA is used first and then dsRNA (PIC). Like TLR3, IL-6 is a rejuvenation marker.
Figure 16:
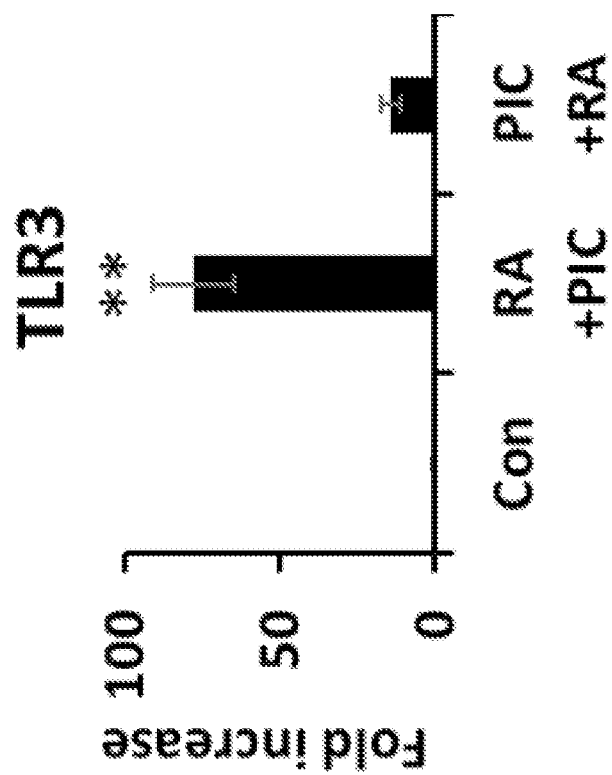

As shown in FIG. 15, TLR3 is a marker of rejuvenation in the skin and increases synergistically with both compounds. As shown in FIG. 16, TLR3 and IL-6 respond well in embodiments in which RA is used first and then dsRNA (PIC). Like TLR3, IL-6 is a rejuvenation marker.

Figure 17:
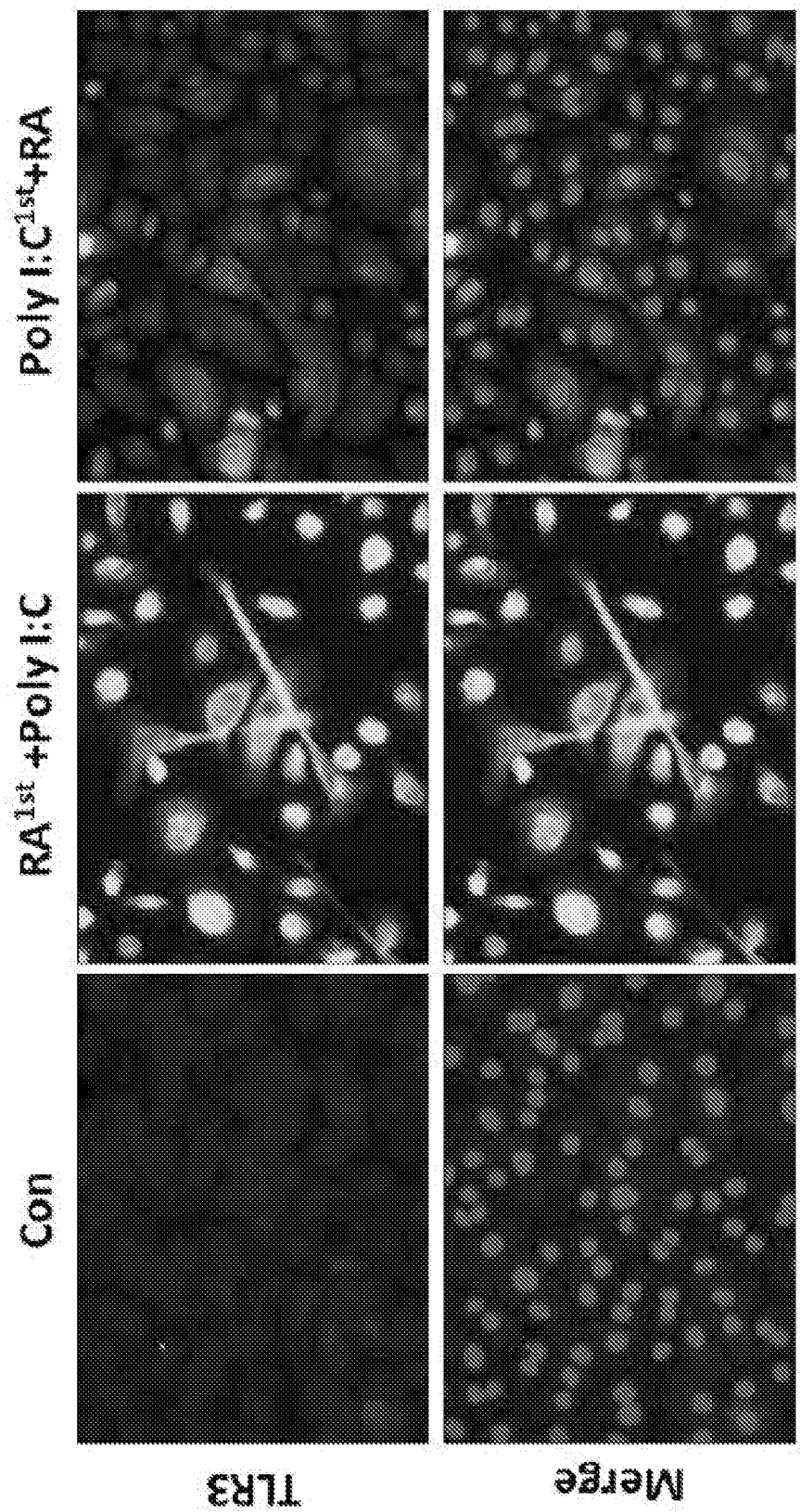
FIG. 17. qRT-PCR show how the order is very important for optimal induction. Green is TLR3 protein.
Figure 18:
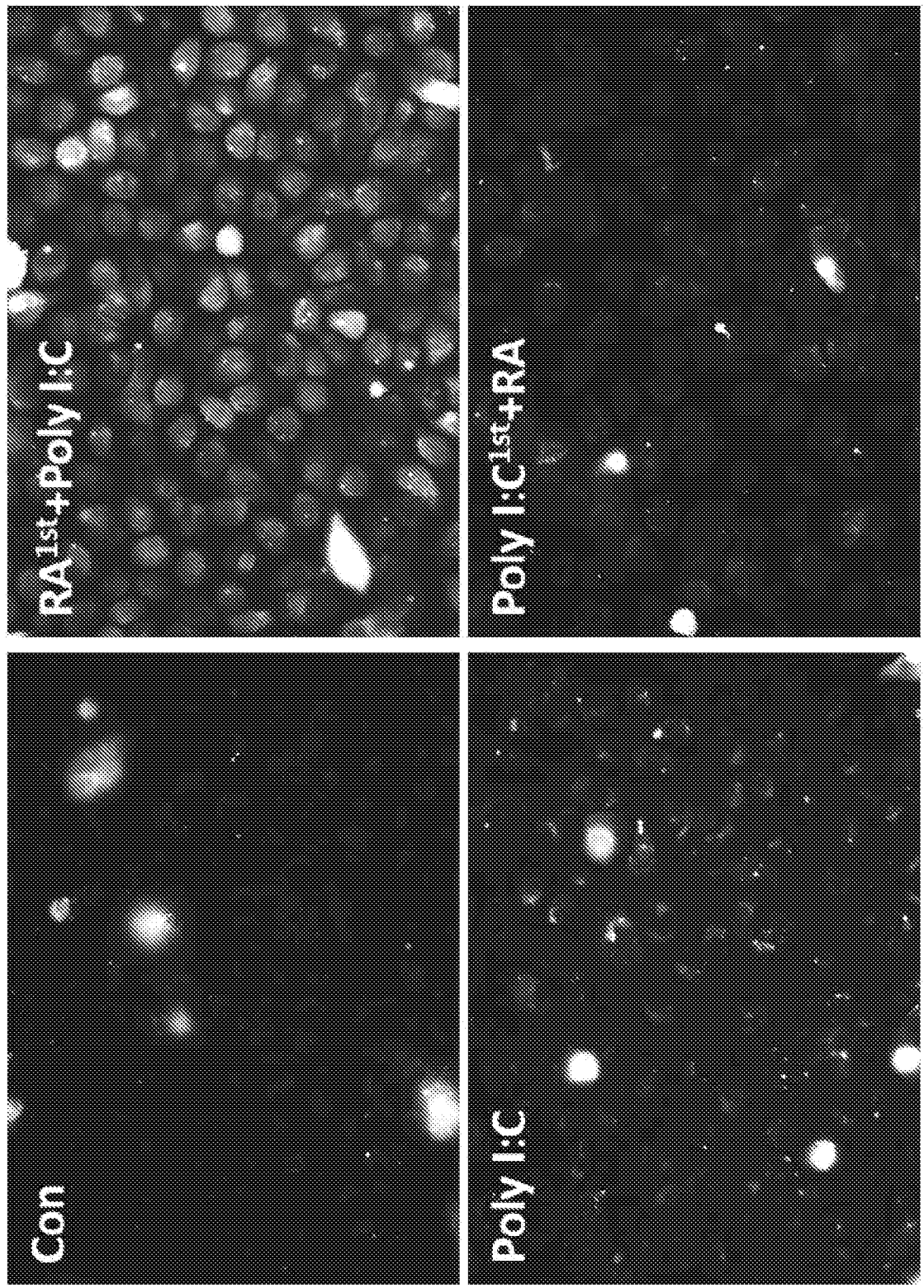
FIG. 18. Without being limited by any theory, the order of administration of dsRNA/RA can be important because RA enhances the entry of dsRNA (PIC). Here, PIC is white and accumulates in cells much more effectively after pre-treatment with RA.

In FIG. 17, qRT-PCR show how the order is very important for optimal induction. Green is TLR3 protein. Without being limited to any particular theory, the stain in FIG. 18 suggests that the reason the order is important is that RA enhances the entry of dsRNA (PIC). Here, PIC is white and accumulates in cells much more effectively after pre-treatment with RA.

We claim:

1. A method for treating wrinkles in a subject comprising the steps of:
   (a) administering to the area of the subject comprising a wrinkle a composition comprising an effective amount of retinoic acid or a derivative thereof; and
   (b) administering to the area of the subject comprising a wrinkle a composition comprising an effective amount of a toll-like receptor 3 (TLR3) agonist.

2. The method of claim 1, wherein the retinoic acid or derivative thereof comprises all-trans retinoic acid.

3. The method of claim 1, wherein the TLR3 agonist comprises double-stranded ribonucleic acid (dsRNA).

4. The method of claim 3, wherein the dsRNA comprises polyinosinic:polycytidylic acid (Poly I:C).

5. The method of claim 1, wherein the compositions are administered topically.

6. The method of claim 1, wherein the compositions are administered by injection.

7. A method for stimulating hair follicle neogenesis in a subject comprising the steps of:
  (a) administering to the subject a composition comprising an effective amount of retinoic acid or a derivative thereof; and
  (b) administering to the subject a composition comprising an effective amount of a TLR3 agonist.

8. The method of claim 7, wherein the subject has alopecia.

9. The method of claim 7, wherein the subject is bald.

10. The method of claim 7, wherein the subject has a wound.

11. The method of claim 7, wherein the subject has photoaging.

12. The method of claim 7, wherein the retinoic acid or derivative thereof comprises all-trans retinoic acid.

13. The method of claim 7, wherein the TLR3 agonist comprises double-stranded ribonucleic acid (dsRNA).

14. The method of claim 13, wherein the dsRNA comprises polyinosinic:polycytidylic acid (Poly I:C).

15. The method of claim 7, wherein the compositions are administered directly to a site on the subject that requires hair follicle neogenesis.

16. The method of claim 15, wherein the retinoic acid or a derivative thereof and the TLR3 agonist are administered topically.

17. The method of claim 15, wherein the compositions are administered by injection.

18. The method of claim 7, further comprising administering a composition comprising an effective amount of LL-37.

* * * * *

SEQUENCE LISTING

<160> NUMBER OF SEQ ID NOS: 13

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser

<210> SEQ ID NO 2
<211> LENGTH: 22
<212> TYPE: DNA
<213> ORGANISM: Artificial Sequence
<220> FEATURE:
<223> OTHER INFORMATION: Cre forward primer

<400> SEQUENCE: 2
gaccaggttc gttcactcat gg                                              22

<210> SEQ ID NO 3
<211> LENGTH: 22
<212> TYPE: DNA
<213> ORGANISM: Artificial Sequence
<220> FEATURE:
<223> OTHER INFORMATION: Cre reverse primer

<400> SEQUENCE: 3
aggctaagtg ccttctctac ac                                              22

<210> SEQ ID NO 4
<211> LENGTH: 20
<212> TYPE: DNA
<213> ORGANISM: Artificial Sequence
<220> FEATURE:
<223> OTHER INFORMATION: Rar alpha flox forward primer

<400> SEQUENCE: 4
cagggaggat gctgtttgta                                                 20

<210> SEQ ID NO 5
<211> LENGTH: 20
<212> TYPE: DNA
<213> ORGANISM: Artificial Sequence
<220> FEATURE:
<223> OTHER INFORMATION: Rar alpha flox reverse primer

<400> SEQUENCE: 5
cctatgaccc aggactcagc                                                 20

<210> SEQ ID NO 6
<211> LENGTH: 20
<212> TYPE: DNA
<213> ORGANISM: Artificial Sequence
<220> FEATURE:
<223> OTHER INFORMATION: Rar gamma flox forward primer

<400> SEQUENCE: 6
agctcagtgg tggaatgctt                                                 20

<210> SEQ ID NO 7
<211> LENGTH: 20
<212> TYPE: DNA
<213> ORGANISM: Artificial Sequence
<220> FEATURE:
<223> OTHER INFORMATION: Rar gamme flox reverse primer

<400> SEQUENCE: 7
ttttctgaat gctgcgtctg                                                 20

<210> SEQ ID NO 8
<211> LENGTH: 20
<212> TYPE: DNA
<213> ORGANISM: Artificial Sequence

```
<220> FEATURE:
<223> OTHER INFORMATION: Rar alpha KO forward primer

<400> SEQUENCE: 8
tttgcctgct cttctgactg                                              20

<210> SEQ ID NO 9
<211> LENGTH: 20
<212> TYPE: DNA
<213> ORGANISM: Artificial Sequence
<220> FEATURE:
<223> OTHER INFORMATION: Rar alpha KO reverse primer (WT)

<400> SEQUENCE: 9
acggtgtgct gtaaccactg                                              20

<210> SEQ ID NO 10
<211> LENGTH: 20
<212> TYPE: DNA
<213> ORGANISM: Artificial Sequence
<220> FEATURE:
<223> OTHER INFORMATION: Rar alpha KO reverse primer (Mut)

<400> SEQUENCE: 10
gccagaggcc acttgtgtag                                              20

<210> SEQ ID NO 11
<211> LENGTH: 22
<212> TYPE: DNA
<213> ORGANISM: Artificial Sequence
<220> FEATURE:
<223> OTHER INFORMATION: Tlr3 KO forward primer

<400> SEQUENCE: 11
aattcatcag tgccatgagt tt                                           22

<210> SEQ ID NO 12
<211> LENGTH: 20
<212> TYPE: DNA
<213> ORGANISM: Artificial Sequence
<220> FEATURE:
<223> OTHER INFORMATION: Tlr3 KO reverse primer (WT)

<400> SEQUENCE: 12
gcaacccttt caaaaaccag                                              20

<210> SEQ ID NO 13
<211> LENGTH: 20
<212> TYPE: DNA
<213> ORGANISM: Artificial Sequence
<220> FEATURE:
<223> OTHER INFORMATION: Tlr3 KO reverse primer (Mut)

<400> SEQUENCE: 13
gccagaggcc acttgtgtag                                              20
```